United States Patent
Liu et al.

(10) Patent No.: US 8,669,257 B2
(45) Date of Patent: Mar. 11, 2014

(54) PHENAZINE DERIVATIVES AND USES THEREOF AS POTASSIUM CHANNEL MODULATORS

(75) Inventors: Jun O. Liu, Clarksville, MD (US); Yunzhao Ren, Timonium, MD (US); Fan Pan, Baltimore, MD (US); Curtis R. Chong, Honolulu, HI (US); Reinhold Penner, Honolulu, HI (US); Jonathan R. Behr, Cambridge, MA (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 12/729,083

(22) Filed: Mar. 22, 2010

(65) Prior Publication Data

US 2010/0330156 A1 Dec. 30, 2010

Related U.S. Application Data

(63) Continuation of application No. PCT/US2008/011009, filed on Sep. 22, 2008.

(60) Provisional application No. 60/994,826, filed on Sep. 21, 2007, provisional application No. 61/084,041, filed on Aug. 22, 2008.

(51) Int. Cl.
*A61K 31/495* (2006.01)
*C07D 241/46* (2006.01)

(52) U.S. Cl.
USPC ........... 514/250; 544/347; 546/244; 546/304; 548/335.1; 548/579

(58) Field of Classification Search
USPC .................. 514/250; 544/347; 546/244, 304; 548/335.1, 579
See application file for complete search history.

(56) References Cited

U.S. PATENT DOCUMENTS

| | | | |
|---|---|---|---|
| 2,948,726 A | 8/1960 | Barry et al. | |
| 5,763,443 A | 6/1998 | Medlen et al. | |
| 2002/0006403 A1* | 1/2002 | Yu et al. | 424/142.1 |

OTHER PUBLICATIONS

Jordan, V. C. Nature Reviews: Drug Discovery, 2, 2003, 205.*
Hackam, et al. JAMA, 296(14), 2006, 1731-1732.*
Anderson R, et al. "Clofazimine and B669 inhibit the proliferative responses and Na+, K(+)-adenosine triphosphatase activity of human lymphocytes by a lysophospholipid-dependent mechanism." Biochem Pharmacol. Dec. 3, 1993;46(11):2029-2038.
Lee SJ, et al. "Treatment of chronic graft-versus-host disease with clofazimine." Blood. Apr. 1, 1997;89(7):2298-2302.
Bezerra EL, et al. "Double-blind, randomized, controlled clinical trial of clofazimine compared with chloroquine in patients with systemic lupus erythematosus." Arthritis Rheum. Oct. 2005;52(10):3073-3078.
Arbiser JL, et al. "Clofazimine: A Review of Its Medical Uses and Mechanisms of Action". J Am Acad Dermatol. Feb. 1995;32(2 Pt 1):241-247.
Reddy VM, et al. "Antimycobacterial activities of riminophenazines" J Antimicrobial Chem. May 1999; 43(5):615-623.
O'Sullivan JF, et al. "Clofazimine analogues active against a clofazimine-resistant organism" J Med Chem. Mar. 1988;31(3):567-72.
Twomey D, et al. "Some novel halogenated phenazine derivatives" J Heterocyclic Chem. 1986 US; 23(2):615-620.
Ren YR, et al. "Clofazimine Inhibits Human Kv1.3 Potassium Channel by Perturbing Calcium Oscillation in T Lymphocytes" PloS One. Dec. 2008;3(12).

* cited by examiner

*Primary Examiner* — Douglas M Willis
(74) *Attorney, Agent, or Firm* — Edwards Wildman Palmer LLP; Peter F. Corless

(57) ABSTRACT

The present invention provides compounds of Formula I:

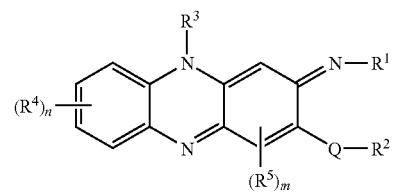

or a pharmaceutically acceptable salt thereof, wherein each of W, Q, $R^1$, $R^2$, $R^3$, $R^4$, $R^5$, m, and n is as defined herein, pharmaceutically acceptable compositions thereof, and methods of using the same.

8 Claims, 14 Drawing Sheets

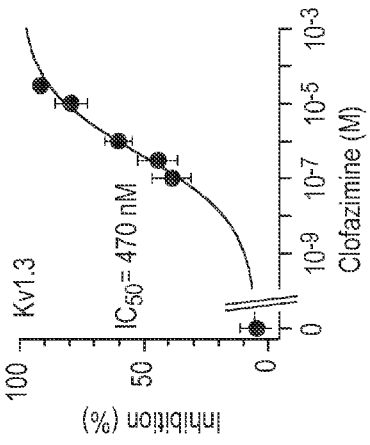
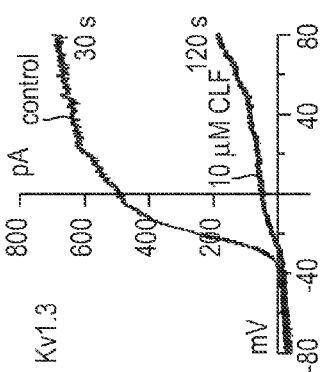
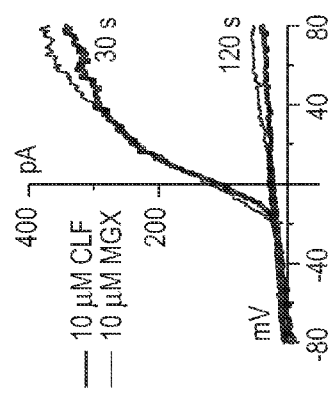
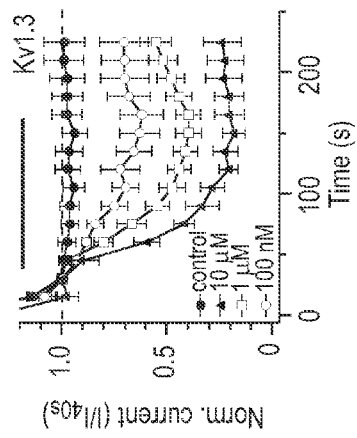
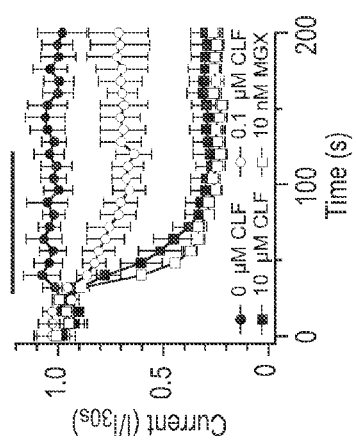

*Days after skin transplantation/cell injection

- ◇ Background
- □ 1mM Ca2+
- △ 5mM EGTA
- × 50uM clof + Ca2+

FIG. 7C

IP | in vitro dephosporylation

| | | | | |
|---|---|---|---|---|
| 1mM Ca$^{2+}$ | + | - | + | + |
| 5mM EGTA | - | + | - | - |
| 50µM Clof | - | + | + | - |
| 50µM TFP | - | - | - | - |

FIG. 7D

| | | | | | | | |
|---|---|---|---|---|---|---|---|
| Ga14-Luc | + | + | + | + | + | + | + |
| CNΔC / NFAT-N | - | + | + | + | + | + | + |
| 1µM Ion | - | - | - | + | + | + | + |
| 50nM clof | - | - | - | - | + | - | - |
| 0.5µM clof | - | - | + | - | - | + | - |
| 5µM clof | - | - | - | - | - | - | + |

Y-axis: RLA (%)

5µM Clof pre-incubation

DMSO    5 Min    30 Min    1 Hr    2 Hr

PHENAZINE DERIVATIVES AND USES THEREOF AS POTASSIUM CHANNEL MODULATORS

The present application is a continuation of International Application No. PCT/US2008/011009 (WO2009/042114) filed Sep. 22, 2008, which claims the benefit of U.S. Provisional Application number 60/994,826, filed Sep. 21, 2007 and U.S. Provisional Application number 61/084,041, filed Aug. 22, 2008, each of which applications are incorporated herein by reference in their entirety.

SEQUENCE LISTING

The instant application contains a Sequence Listing which has been submitted via EFS-Web and is hereby incorporated by reference in its entirety. Said ASCII copy, created on May 6, 2010, is named 82662716.txt and is 691 bytes in size.

BACKGROUND OF THE INVENTION

Autoimmune disease occurs when a component of the immune system causes damage to the body (Harvey & Champe. *Immunology.* 2008. Williams & Wilkins, Philadelphia, Pa.). A number of autoimmune diseases exist which cause physical damage and greatly impact the quality of life of the sufferer. Several autoimmune diseases such as lupus may result in death if left unchecked. Current therapies for treatment of autoimmune disease have produced varying degrees of efficacy and in many cases unacceptable adverse event profiles. A clear unmet need exists for better treatments of autoimmune diseases.

Better therapeutics could result from treating the underlying pathologies of autoimmune diseases. The etiology of the various diseases is complex and differs from disease to disease. However, a number of autoimmune diseases can be partly attributed to the pathological actions of T-cells that either release substances which damage tissue or which activate other immune cells which cause damage. Psoriasis (Sabet et al. *Experimental Dermatology.* 2007. 16: 779-798), rheumatoid arthritis (Cope et al. *Clin Exp Rheumatol.* 2007. 25(5 Suppl 46):54-1), multiple sclerosis (MS) (Winquist et al. *Biochemical Pharmacology.* 2007. 74: 1321-1329) and type I diabetes (Mallone et al. *Curr Diab Rep.* 2008. 2:101-6) are examples of diseases in which T-cells are believed to play a contributory role to disease pathology. Several therapeutics including alefacept (Lev-Tov et al., *Rev Recent Clin. Trials.* 2006. 1:163-164), FK-506 and cyclosporine exert therapeutic actions by suppressing the activity of T-cells. The use of such T-cells suppressive drugs has been greatly limited to due to the global immunosuppressive nature of the agents. A need exists for a therapy which has the ability to suppress the pathological actions of T-cells without causing general immunosupression which leads to an increased risk of infection.

One potential strategy for selective T-cell suppression is to target activated effector memory T-cells while leaving central naïve T-cells untouched. One such strategy would be to target a component of T-cells which is upregulated in pathological effector memory cells and which is also critical for the activation of the T-cell. The potassium channel Kv1.3 has been hypothesized to be such a target (Chandy et al. *TIPS.* 2004. 25: 280-289). Kv1.3 is a critical component of the Calcium Release Activated Channel (CRAC) signaling pathway. In a simplified summary, upon activation of the CD3/T-cell receptor complex (e.g., by an antigen presenting cell), phospholipase C is activated which in turn causes release of calcium from the endoplasmic reticulum. The intracellular stores of calcium activate the CRAC channel which causes the influx of calcium and subsequent downstream signaling to the critical components of T-cell activation including calcineurin and nuclear factor of activated T-cells (NFAT).

In order for the continued influx of calcium through CRAC to continue, efflux of positively charged potassium is necessary to maintain the membrane potential. This potassium efflux can occur through either Kv1.3 or through the IKCa1 channel. The specific role of T-cells expressing high levels of Kv1.3 has been explored in several autoimmune diseases which are thought to be T-cell mediated. In MS patients, the number of Kv1.3 channels is upregulated in myelin-reactive T-cells and a specific Kv1.3 inhibitor decreased the activity of isolated pathogenic T-cells (Wulff et al. *J. Clin. Invest.* 2003. 111: 1703-1713). Furthermore, a Kv1.3 inhibitor was shown to be effective in prevention of death and in treatment of experimental autoimmune encephalitis (EAE) in rats, which is considered a standard animal model for MS (Beeton et al. *Proc. Natl. Acad. Sci. USA.* 2001. 98: 13942-13947). Likewise, Kv1.3 was shown to be upregulated in T-cells isolated from the synovial fluid of rheumatoid arthritis patients and a Kv1.3 inhibitor had the ability to decrease the activity of the isolated pathological cells (Beeton et al. *Proc. Natl. Acad. Sci. USA.* 2006. 98: 13942-13947). Beeton et al. further showed that a Kv1.3 inhibitor had the ability to decrease the amount of joint damage associated with pristane injection in a standard animal model of rheumatoid arthritis. Kv1.3 was also upregulated in islet reactive T-cells isolated from Type I Diabetes patients and Kv1.3 inhibitors decreased the activity of the pathogenic T-cells (Beeton et al. *Proc. Nall. Acad. Sci. USA.* 2006. 98: 13942-13947). Beeton et al. also showed that a Kv1.3 inhibitor could reduce the incidence of diabetes in a standard animal model. Azam et al. showed that Kv1.3 inhibitors have the ability to reduce ear swelling in rats following the animals' sensitization and subsequent exposure to oxazolone which is considered a model for both psoriasis and allergic contact dermatitis (Azam et al. *J. Investigative Dermatology.* 2007. 127: 1419-1429).

Kv1.3 has also been suggested as a target for type 2 diabeties, as Kv1.3 knockout mice had increased peripheral insulin sensivity and inhibition of Kv1.3 results in translocation of the glucose transporter GLUT4 to the plasma membrane (Xu et al. *Proc. Natl. Acad. Sci. USA.* 2004. 101: 3112-3117). The effects of Kv1.3 inhibition appeared to be additive to insulin in promoting GLUT4 transport (Li et al. *Am J Physiol Cell Physiol.* 2006. 290: C345-C351). A variant in the promoter of the Kv1.3 gene is also associated with impaired glucose tolerance and lower insulin sensitivity (Tschritter et al. *The Journal of Clinical Endocrinology & Metabolism.* 2006. 91: 654-658).

Accordingly, Kv1.3 is a promising target for several autoimmune diseases as well as type 2 diabetes and there exists a need for an inhibitor of Kv1.3 which has an adverse event and pharmacokinetic profile such that the inhibitor is therapeutically viable.

SUMMARY OF THE INVENTION

It has now been found that compounds of this invention are effective as modulators of Kv1.3. Such compounds have the general formula I:

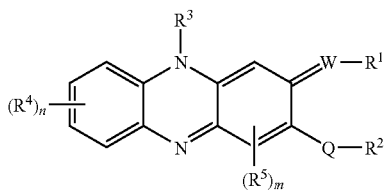

or a pharmaceutically acceptable salt thereof, wherein each of W, Q, $R^2$, $R^3$, $R^4$, $R^5$, m, and n is as defined herein.

Compounds of the present invention and pharmaceutically acceptable compositions thereof, are useful for treating a variety of diseases, disorders or conditions, mediated by Kv1.3 and, in some embodiments, T-cell activation such as activation of effector memory T-cells. Such diseases, disorders, or conditions include those described herein.

Compounds provided by this invention are also useful for the study of Kv1.3 in biological and pathological phenomena, the study of intracellular signal transduction pathways mediated by Kv1.3, and the comparative evaluation of new Kv1.3 inhibitors.

BRIEF DESCRIPTION OF THE DRAWINGS

FIG. 3. Clofazimine inhibits the Kv1.3 channel. (A) Averaged time course of Kv1.3 currents measured in Jurkat T-cells in the absence and the presence of clofazimine (CLF) or margatoxin (MGX). Various concentrations of CLF (n=5 each) or 10 nM MGX (open squares, n=5) were applied as indicated by the black bar. Currents were elicited by applying a ramp protocol from −100 mV to +100 mV over a span of 50 ms and acquired every 2 s. Holding potential was −80 mV. Current amplitudes were extracted at +80 mV and plotted versus the time of the experiment. Currents were normalized to cell size and plotted as pA/pF. Error bars indicate S.E.M. (B) Current-voltage relationship of Kv1.3 currents taken from example cells and extracted before (30 s) or after application (120 s) of either 10 µM CLF (thick trace) or 10 nM MGX (thin trace). (C) Dose-response curve of the inhibitory effect of CLF (closed circles, n=5 each). Data were normalized to the current measured before application at 30 s as $I/I_{30s}$. The inhibition was measured at the end of application at 120s. A dose-response fit to the data resulted in an $IC_{50}$ of 300 nM and a Hill coefficient of 0.75. The maximum inhibitory effect of CLF was compared to the inhibitory effect of 10 nM MGX (open circle, n=5), a saturating concentration to assure Kv1.3 inhibition. The dashed line indicates the maximum inhibitory effect of MGX. (D) Current behavior of heterologous mouse Kv1.3 expressed in L929 cells plotted over time in response to increasing concentrations of clofazimine, applied through a wide-mouth glass pipette at the time indicated by the black bar (control, closed circles, no application, n=7; 10 µM, closed triangles, n=4; 1 µM, open square, n=6; 100 nM, open circles, n=5). Currents were measured by application of a ramp protocol from −100 mV to +100 mV over 500 ms and given at 5 s intervals. Current amplitudes were assessed at +80 mV, normalized to the current amplitude at 40 s, averaged and plotted versus time. Error bars indicate S.E.M. (E) IN curve of a representative cell expressing mouse Kv1.3 with control IN (black) extracted at 40 s after whole-cell establishment and the IN for 10 µM clofazimine extracted at the end of application (red, 160 s). (F) Concentration-response behavior of mouse Kv1.3 expressed in L929 cells to increasing concentrations of clofazimine (n=4-7). A fit to the data gave an $IC_{50}$ of 470 nM with a Hill coefficient of 0.5.

DETAILED DESCRIPTION OF CERTAIN EMBODIMENTS

Figure 1A:
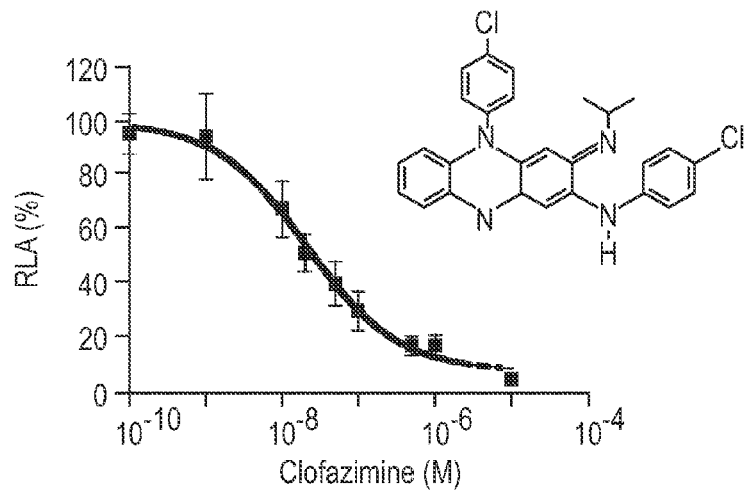
FIG. 1. Clofazimine inhibits IL-2 production and NFAT activation in Jurkat T-cells. (A) Clofazimine inhibits IL-2 proximal promoter driven-luciferase stimulated by PMA/ionomycin in Jurkat T-cells (n=6). The $IC_{50}$ for reporter assay is 21.8±4.4 nM. (B) Clofazimine inhibits IL-2 production in PMA/thapsigargin-stimulated Jurkat T-cells ($IC_{50}$=1.10±0.26 µM) and human mixed lymphocyte reaction (MLR) ($IC_{50}$=0.90±0.17 µM) (n=6 each). (C) Clofazimine inhibits NFAT pathway in Jurkat T-cells. The $IC_{50}$s of clofazimine in the IL-2, NFAT, NF-κB luciferase reporter assays are 56.0±14.8 nM, 113±30 nM and 2.43±1.25 µM, respectively (n=6 each). Both reporters were stimulated with PMA/ionomycin. (D) Clofazimine significantly enhances AP-1 luciferase reporter at high concentrations (>1 µM, n=6). The reporter was also stimulated by PMA/ionomycin. (E) Clofazimine inhibits dephosphorylation of endogenous NFATc2 in response to ionomycin treatment. NFATc2 and α-tubulin were detected by Western blot using specific antibodies.

Immunosuppressive agents constitute a major class of drugs for the treatment of undesirable or abnormal activation of T lymphocytes and the immune system associated with organ transplantation and autoimmune diseases. Among the most widely used immunosuppressive drugs in the clinic are cyclosporin A (CsA) and FK506, natural products of microbial origin that work through inhibition of the intracellular calcium signaling cascade downstream of the T-cell receptor (TCR). By recruiting abundant cytosolic immunophilin receptors, each of these immunosuppressive drugs induces the formation of a ternary complex with the calcium, calmodulin-dependent protein phosphatase calcineurin, thereby blocking access to the active site of calcineurin by its substrate, nuclear factor of activated T-cells (NFAT), preventing the dephosphorylation and subsequent nuclear translocation of NFAT. Despite its widespread use among organ transplantation patients, CsA and FK506 exhibit significant side effects, particularly nephrotoxicity, as well as an increased risk of infection, which prevents their widespread use for the treatment of autoimmune diseases. Since the nephrotoxicity of CsA and FK506 was found to share the same molecular basis as their immunosuppressive effect, attention has been turned to other signal transducers downstream of the TCR as potential therapeutic targets in recent years.

The Kv1.3 potassium channel has emerged as one of the most promising targets for novel immunosuppressants. Although no clear T-cell phenotype was observed in Kv1.3 knockout mice, several lines of evidence exist in support of a critical role of the Kv1.3 channel in the activation and function of human T-cells. In particular, Kv1.3 has been shown to play a unique role in effector memory T-cellactivation and in the pathogenesis of a myriad of important autoimmune diseases. Notably, Kv1.3 has been shown to be highly expressed in auto-reactive effector memory T-cells from MS patients. As a result, extensive efforts have been made to discover and develop small molecule inhibitors of Kv1.3 as novel immunosuppressants and immunomodulators. Structurally distinct inhibitors of Kv1.3, none of which are phenazines, have been reported, including UK-78282, W1N17317-3, correolide, verapamil, and 5-phenylalkoxypsoralens (Psora), among others. Several of the inhibitors have been shown to be effective in animal models of autoimmunity. However, none has reached the clinic due to lack of potency, specificity, bioavailability or easy access due to structural complexity.

1. General Description of Compounds of the Invention:

As described generally above, provided compounds are useful as inhibitors of Kv1.3. In certain embodiments, the present invention provides a compound of formula I:

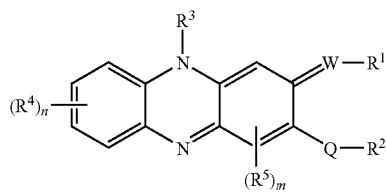

I or a pharmaceutically acceptable salt thereof, wherein:

W is =O, =N—, or =C(R)—;

$R^1$ is an optionally substituted group selected from $C_{1-6}$ aliphatic, $C_{3-7}$ cycloaliphatic, a 6-10 membered monocyclic or bicyclic aromatic carbocyclic ring, or a 5-10 membered monocyclic or bicyclic saturated, partially unsaturated, or aromatic ring having 1-4 heteroatoms independently selected from nitrogen, oxygen, or sulfur;

Q is —O—, —S—, —C(R)$_2$—, or —N(R)—;

each R is independently hydrogen or an optionally substituted $C_{1-6}$ aliphatic group, or:
  two R groups on the same nitrogen are taken together with the nitrogen atom to form a 4-7 membered saturated, partially unsaturated, or aromatic ring having 1-4 heteroatoms independently selected from nitrogen, oxygen, or sulfur;

$R^2$ is an optionally substituted group selected from $C_{3-7}$ cycloaliphatic, a 6-10 membered monocyclic or bicyclic aromatic carbocyclic ring, or a 5-10 membered monocyclic or bicyclic saturated, partially unsaturated, or aromatic ring having 1-4 heteroatoms independently selected from nitrogen, oxygen, or sulfur;

$R^3$ is an optionally substituted group selected from $C_{3-7}$ cycloaliphatic, a 6-10 membered monocyclic or bicyclic aromatic carbocyclic ring, or a 5-10 membered monocyclic or bicyclic saturated, partially unsaturated, or aromatic ring having 1-4 heteroatoms independently selected from nitrogen, oxygen, or sulfur;

n is 0-4;

each $R^4$ is independently selected from halogen, CN, R, OR, SR, N(R)$_2$, C(O)R, C(O)OR, C(O)N(R)$_2$, N(R)C(O)R, OC(O)R, SO$_2$R, SO$_2$N(R)$_2$, N(R)SO$_2$R, or N(R)C(O)N(R)$_2$;

m is 0-2; and each $R^5$ is independently selected from halogen, CN, R, OR, SR, or N(R)$_2$.

2. Compounds and Definitions:

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Smith, M. B. and March, J., John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments aliphatic groups contain 1-2 aliphatic carbon atoms.

As used herein, the term "cycloaliphatic" (or "carbocycle" or "cycloalkyl") refers to a hydrocarbon that is completely saturated or that contains one or more units of unsaturation, but which is not aromatic, that has a single point of attachment to the rest of the molecule wherein any individual ring in said bicyclic ring system has 3-7 members. Suitable aliphatic groups include, but are not limited to, linear or branched, substituted or unsubstituted alkyl, alkenyl, alkynyl groups and hybrids thereof such as (cycloalkyl)alkyl, (cycloalkenyl) alkyl or (cycloalkyl)alkenyl.

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR+ (as in N-substituted pyrrolidinyl)).

The term "unsaturated", as used herein, means that a moiety has one or more units of unsaturation.

The term "halogen" means F, Cl, Br, or I.

The term "aryl" used alone or as part of a larger moiety as in "aralkyl," "aralkoxy," or "aryloxyalkyl," refers to monocyclic and bicyclic ring systems having a total of five to 10 ring members, wherein at least one ring in the system is aromatic and wherein each ring in the system contains three to seven ring members. The term "aryl" may be used interchangeably with the term "aryl ring". In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic". The term "heteroaralkyl" refers to an alkyl group substituted by a heteroaryl.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above.

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —$(CH_2)_{0-4}R°$; —$(CH_2)_{0-4}OR°$; —$O(CH_2)_{0-4}R°$, —$O$—$(CH_2)_{0-4}C(O)OR°$; —$(CH_2)_{0-4}CH(OR°)_2$; —$(CH_2)_{0-4}$ $SR°$; —$(CH_2)_{0-4}Ph$, which may be substituted with $R°$; —$(CH_2)_{0-4}O(CH_2)_{0-1}Ph$ which may be substituted with $R°$; —$CH$=$CHPh$, which may be substituted with $R°$; —$(CH_2)_{0-4}$ $O(CH_2)_{0-1}$-pyridyl which may be substituted with $R°$; —$NO_2$; —$CN$; —$N_3$; —$(CH_2)_{0-4}N(R°)_2$; —$(CH_2)_{0-4}$ $N(R°)C(O)R°$; —$N(R°)C(S)R°$; —$(CH_2)_{0-4}N$ $(R°)C(O)NR°_2$; —$N(R°)C(S)NR°_2$; —$(CH_2)_{0-4}N(R°)C(O)$ $OR°$; —$N(R°)N(R°)C(O)R°$; —$N(R°)N(R°)C(O)NR°_2$; —$N(R°)N(R°)C(O)OR°$; —$(CH_2)_{0-4}C(O)R°$; —$C(S)R°$; —$(CH_2)_{0-4}C(O)OR°$; —$(CH_2)_{0-4}C(O)SR°$; —$(CH_2)_{0-4}C(O)$ $OSiR°_3$; —$(CH_2)_{0-4}OC(O)R°$; —$OC(O)(CH_2)_{0-4}SR$—, $SC(S)SR°$; —$(CH_2)_{0-4}SC(O)R°$; —$(CH_2)_{0-4}C(O)NR°_2$; —$C(S)NR°_2$; —$C(S)SR°$; —$SC(S)SR°$, —$(CH_2)_{0-4}OC(O)$ $NR°_2$; —$C(O)N(OR°)R°$; —$C(O)C(O)R°$; —$C(O)CH_2C(O)$ $R°$; —$C(NOR°)R°$; —$(CH_2)_{0-4}SSR°$; —$(CH_2)_{0-4}S(O)_2R°$; —$(CH_2)_{0-4}S(O)_2OR°$; —$(CH_2)_{0-4}OS(O)_2R°$; —$S(O)_2NR°_2$; —$(CH_2)_{0-4}S(O)R°$; —$N(R°)S(O)_2NR°_2$; —$N(R°)S(O)_2R°$; —$N(OR°)R°$; —$C(NH)NR°_2$; —$P(O)_2R°$; —$P(O)R°_2$; —$OP(O)R°_2$; —$OP(O)(OR°)_2$; $SiR°_3$; —$(C_{1-4}$ straight or branched alkylene)$O$—$N(R°)_2$; or —$(C_{1-4}$ straight or branched alkylene)$C(O)O$—$N(R°)_2$, wherein each $R°$ may be substituted as defined below and is independently hydrogen, $C_{1-6}$ aliphatic, —$CH_2Ph$, —$O(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R°$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$)$_2$; —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet$$_2$, —NO$_2$, —SiR$^\bullet$$_3$, —OSiR$^\bullet$$_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_1$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_1$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger$$_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger$$_2$, —C(S)NR$^\dagger$$_2$, —C(NH)NR$^\dagger$$_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_1$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower-alkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C— or $^{14}$C-enriched carbon are within the scope of this invention. Such compounds are useful, for example, as analytical tools, as probes in biological assays, or as therapeutic agents in accordance with the present invention.

As used herein, the term "inhibitor" is defined as a compound that binds to and for inhibits Kv1.3 with measurable affinity. In certain embodiments, an inhibitor has an IC$_{50}$ and/or binding constant of less about 50 μM, less than about 1 less than about 500 nM, less than about 100 nM, or less than about 10 nM.

The terms "measurable affinity" and "measurably inhibit," as used herein, means a measurable change in Kv1.3 activity between a sample comprising a compound of the present invention, or composition thereof, and an equivalent sample in the absence of said compound, or composition thereof.

3. Description of Exemplary Compounds:

As described generally above, the present invention provides a compound of formula I:

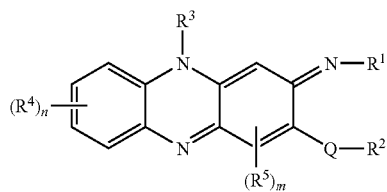

I or a pharmaceutically acceptable salt thereof, wherein each of W, Q, $R^1$, $R^2$, $R^3$, $R^4$, $R^5$, m, and n is as defined herein.

As defined above, W is =O, =N—, or =C(R)—. In certain embodiments, W is =O. In other embodiments, W is =N—. In still other embodiments, W is =C(R)—.

As defined above, the $R^1$ group of formula I is an optionally substituted group selected from $C_{1-6}$ aliphatic, $C_{3-7}$ cycloaliphatic, a 6-10 membered monocyclic or bicyclic aromatic carbocyclic ring, or a 5-10 membered monocyclic or bicyclic saturated, partially unsaturated, or aromatic ring having 1-4 heteroatoms independently selected from nitrogen, oxygen, or sulfur.

In certain embodiments, $R^1$ is optionally substituted $C_{1-6}$ aliphatic. In some embodiments, $R^1$ is substituted $C_{1-6}$ aliphatic. In other embodiments, $R^1$ is an optionally substituted group selected from $C_{3-7}$ cycloaliphatic, a 6-10 membered monocyclic or bicyclic aromatic carbocyclic ring, or a 5-10 membered monocyclic or bicyclic saturated, partially unsaturated, or aromatic ring having 1-4 heteroatoms independently selected from nitrogen, oxygen, or sulfur.

In certain embodiments, $R^1$ is optionally substituted $C_{1-6}$ alkenyl or alkynyl.

In some embodiments, $R^1$ is optionally substituted naphthyl or indanyl.

In some embodiments, $R^1$ is an optionally substituted 5-10 membered monocyclic or bicyclic saturated, partially unsaturated, or aromatic ring having 1-4 heteroatoms independently selected from nitrogen, oxygen, or sulfur. In certain embodiments, $R^1$ is a 5-10 membered heteroaryl ring having 1-4 heteroatoms independently selected from nitrogen, oxygen, or sulfur. In some embodiments, $R^1$ is a 5-6 membered heteroaryl ring having 1-4 heteroatoms independently selected from nitrogen, oxygen, or sulfur. In other embodiments $R^1$ is an 8-10 membered bicyclic heteroaryl ring having 1-4 heteroatoms independently selected from nitrogen, oxygen, or sulfur. Exemplary $R^1$ heteroaryl rings include optionally substituted thienyl, furanyl, pyrrolyl, imidazolyl, pyrazolyl, triazolyl, tetrazolyl, oxazolyl, isoxazolyl, thiazolyl, pyridyl, pyrimidinyl, indolyl, isoindolyl, benzothienyl, benzofuranyl, dibenzofuranyl, indazolyl, benzimidazolyl, benzthiazolyl, quinolyl, isoquinolyl, or quinazolinyl.

In certain embodiments, $R^1$ is an optionally substituted 5-10 membered monocyclic or bicyclic saturated or partially unsaturated heterocyclic ring having 1-3 heteroatoms independently selected from nitrogen, oxygen, or sulfur. In certain embodiments, $R^1$ is an optionally substituted 5-6 membered saturated or partially unsaturated heterocyclic ring having 1-3 heteroatoms independently selected from nitrogen, oxygen, or sulfur. Exemplary $R^1$ heterocyclic rings include tetrahydrofuranyl, tetrahydrothiophenyl pyrrolidinyl, piperidinyl, pyrrolinyl, tetrahydroquinolinyl, tetrahydroisoquinolinyl, piperazinyl, dioxanyl, dioxolanyl, diazepinyl, oxazepinyl, thiazepinyl, morpholinyl, and thiomorpholinyl.

As defined generally above, $R^2$ is an optionally substituted group selected from $C_{3-7}$ cycloaliphatic, a 6-10 membered monocyclic or bicyclic aromatic carbocyclic ring, or a 5-10 membered monocyclic or bicyclic saturated, partially unsaturated, or aromatic ring having 1-4 heteroatoms independently selected from nitrogen, oxygen, or sulfur. In certain embodiments, $R^2$ is optionally substituted $C_{3-7}$ cycloaliphatic. In some embodiments, $R^2$ is cyclopropyl, cyclobutyl, cyclopentyl, or cyclohexyl. In some embodiments, $R^2$ is an optionally substituted a 6-10 membered monocyclic or bicyclic aromatic carbocyclic ring. In other embodiments, $R^2$ is an optionally substituted 5-10 membered monocyclic or bicyclic saturated, partially unsaturated, or aromatic ring having 1-4 heteroatoms independently selected from nitrogen, oxygen, or sulfur.

In some embodiments, $R^2$ is optionally substituted naphthyl or indanyl.

In some embodiments, $R^2$ is an optionally substituted 5-10 membered monocyclic or bicyclic saturated, partially unsaturated, or aromatic ring having 1-4 heteroatoms independently selected from nitrogen, oxygen, or sulfur. In certain embodiments, $R^2$ is a 5-10 membered heteroaryl ring having 1-4 heteroatoms independently selected from nitrogen, oxygen, or sulfur. In some embodiments, $R^2$ is a 5-6 membered heteroaryl ring having 1-4 heteroatoms independently selected from nitrogen, oxygen, or sulfur. In other embodiments $R^2$ is an 8-10 membered bicyclic heteroaryl ring having 1-4 heteroatoms independently selected from nitrogen, oxygen, or sulfur. Exemplary $R^2$ heteroaryl rings include optionally substituted thienyl, furanyl, pyrrolyl, imidazolyl, pyrazolyl, triazolyl, tetrazolyl, oxazolyl, isoxazolyl, thiazolyl, pyridyl, pyrimidinyl, indolyl, isoindolyl, benzothienyl, benzofuranyl, dibenzofuranyl, indazolyl, benzimidazolyl, benzthiazolyl, quinolyl, isoquinolyl, or quinazolinyl.

In certain embodiments, $R^2$ is an optionally substituted 5-10 membered monocyclic or bicyclic saturated or partially unsaturated heterocyclic ring having 1-3 heteroatoms independently selected from nitrogen, oxygen, or sulfur. In certain embodiments, $R^2$ is an optionally substituted 5-6 membered saturated or partially unsaturated heterocyclic ring having 1-3 heteroatoms independently selected from nitrogen, oxygen, or sulfur. Exemplary $R^2$ heterocyclic rings include tetrahydrofuranyl, tetrahydrothiophenyl pyrrolidinyl, piperidinyl, pyrrolinyl, tetrahydroquinolinyl, tetrahydroisoquinolinyl, piperazinyl, dioxanyl, dioxolanyl, diazepinyl, oxazepinyl, thiazepinyl, morpholinyl, and thiomorpholinyl.

As defined generally above, $R^3$ is an optionally substituted group selected from $C_{3-7}$ cycloaliphatic, a 6-10 membered monocyclic or bicyclic aromatic carbocyclic ring, or a 5-10 membered monocyclic or bicyclic saturated, partially unsaturated, or aromatic ring having 1-4 heteroatoms independently selected from nitrogen, oxygen, or sulfur. In certain embodiments, $R^3$ is optionally substituted $C_{3-7}$ aliphatic. In some embodiments, $R^3$ is an optionally substituted a 6-10 membered monocyclic or bicyclic aromatic carbocyclic ring. In other embodiments, $R^3$ is an optionally substituted 5-10 membered monocyclic or bicyclic saturated, partially unsaturated, or aromatic ring having 1-4 heteroatoms independently selected from nitrogen, oxygen, or sulfur.

In some embodiments, $R^3$ is optionally substituted naphthyl or indanyl.

In some embodiments, $R^3$ is an optionally substituted 5-10 membered monocyclic or bicyclic saturated, partially unsaturated, or aromatic ring having 1-4 heteroatoms independently selected from nitrogen, oxygen, or sulfur. In certain embodiments, $R^3$ is a 5-10 membered heteroaryl ring having 1-4 heteroatoms independently selected from nitrogen, oxygen, or sulfur. In some embodiments, $R^3$ is a 5-6 membered heteroaryl ring having 1-4 heteroatoms independently selected from nitrogen, oxygen, or sulfur. In other embodiments $R^3$ is an 8-10 membered bicyclic heteroaryl ring having 1-4 heteroatoms independently selected from nitrogen, oxygen, or sulfur. Exemplary $R^3$ heteroaryl rings include optionally substituted thienyl, furanyl, pyrrolyl, imidazolyl, pyrazolyl, triazolyl, tetrazolyl, oxazolyl, isoxazolyl, thiazolyl, pyridyl, pyrimidinyl, indolyl, isoindolyl, benzothienyl, benzofuranyl, dibenzofuranyl, indazolyl, benzimidazolyl, benzthiazolyl, quinolyl, isoquinolyl, or quinazolinyl.

In certain embodiments, $R^3$ is an optionally substituted 5-10 membered monocyclic or bicyclic saturated or partially unsaturated heterocyclic ring having 1-3 heteroatoms independently selected from nitrogen, oxygen, or sulfur. In certain embodiments, $R^3$ is an optionally substituted 5-6 membered saturated or partially unsaturated heterocyclic ring having 1-3 heteroatoms independently selected from nitrogen, oxygen, or sulfur. Exemplary $R^3$ heterocyclic rings include tetrahydrofuranyl, tetrahydrothiophenyl pyrrolidinyl, piperidinyl, pyrrolinyl, tetrahydroquinolinyl, tetrahydroisoquinolinyl, piperazinyl, dioxanyl, dioxolanyl, diazepinyl, oxazepinyl, thiazepinyl, morpholinyl, and thiomorpholinyl.

As defined generally above, the Q group of formula I is Q is —O—, —S—, —C(R)$_2$—, or —N(R)—. In certain embodiments, Q is —N(R)—. In other embodiments, Q is selected from —O—, —S—, or —C(R)$_2$—.

According to one aspect, the present invention provides a compound of any of formulae I-a, I-b, I-c, or I-d:

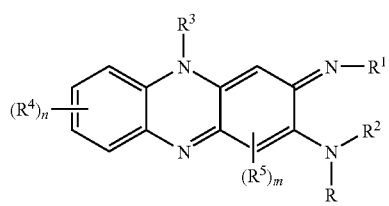

I-a

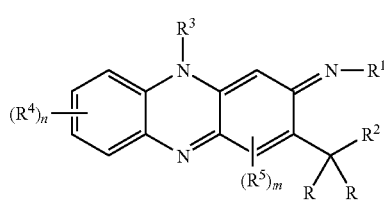

I-b

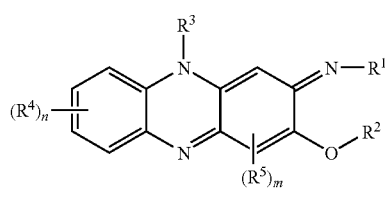

I-c

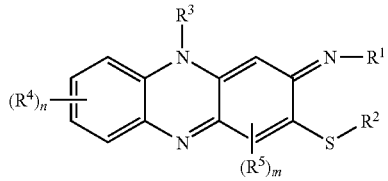

I-d or a pharmaceutically acceptable salt thereof, wherein each of R, $R^1$, $R^2$, $R^3$, $R^4$, $R^5$, m, and n is as defined herein and described in classes and subclasses both singly and in combination.

In certain embodiments, the R group of formula I-a is hydrogen. In other embodiments, the R group of formula I-a is optionally substituted $C_{1-6}$ aliphatic.

In certain embodiments, each R group of formula I-b is hydrogen. In other embodiments, one R group of formula I-b is hydrogen and the other is optionally substituted $C_{1-6}$ aliphatic. In other embodiments, each R group of formula I-b is optionally substituted $C_{1-6}$ aliphatic.

As defined generally above, n is 0-4 and each $R^4$ is independently selected from halogen, CN, R, OR, SR, N(R)$_2$, C(O)R, C(O)OR, C(O)N(R)$_2$, N(R)C(O)R, OC(O)R, SO$_2$R, SO$_2$N(R)$_2$, N(R)SO$_2$R, or N(R)C(O)N(R)$_2$. In certain embodiments, n is 0. In other embodiments, n is 1-4. In some embodiments, n is 1-2. In certain embodiments, n is 1.

In certain embodiments, $R^4$ is halogen, CN, optionally substituted $C_{1-6}$ aliphatic, OR, SR, or N(R)$_2$. In certain embodiments, $R^4$ is fluoro, chloro, methyl, ethyl, propyl, isopropyl, OCH$_3$, OCH$_2$CH$_3$, NH$_2$, NHCH$_3$, or N(CH$_3$)$_2$.

As defined generally above, m is 0-2; and each $R^5$ is independently selected from halogen, CN, R, OR, SR, or N(R)$_2$. In certain embodiments, m is 0. In other embodiments, m is 1. In some embodiments, m is 2. In certain embodiments, $R^5$ is fluoro, chloro, methyl, ethyl, propyl, isopropyl, OCH$_3$, OCH$_2$CH$_3$, NH$_2$, NHCH$_3$, or N(CH$_3$)$_2$.

In certain embodiments, both of m and n are 0. In other embodiments, m is 0 and n is 1. In some embodiments, m is 1 and n is 0.

In certain embodiments, the present invention provides a compound of formula I-a:

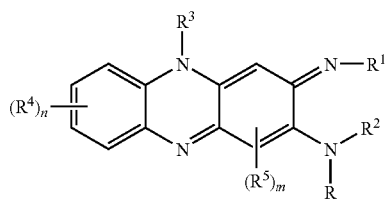

I-a or a pharmaceutically acceptable salt thereof, wherein:
$R^1$ is an optionally, substituted group selected from $C_{2-6}$ alkenyl, $C_{2-6}$ alkynyl, $C_{3-7}$ cycloaliphatic, a 6-10 membered monocyclic or bicyclic aromatic carbocyclic ring, or a 5-10 membered monocyclic or bicyclic saturated, partially unsaturated, or aromatic ring having 1-4 heteroatoms independently selected from nitrogen, oxygen, or sulfur;
each R is independently hydrogen or an optionally substituted $C_{1-6}$ aliphatic group, or:
two R groups on the same nitrogen are taken together with the nitrogen atom to form a 4-7 membered saturated, partially unsaturated, or aromatic ring having 1-4 heteroatoms independently selected from nitrogen, oxygen, or sulfur;

$R^2$ is an optionally substituted group selected from $C_{3-7}$ cycloaliphatic, a 6-10 membered monocyclic or bicyclic aromatic carbocyclic ring, or a 5-10 membered monocyclic or bicyclic saturated, partially unsaturated, or aromatic ring having 1-4 heteroatoms independently selected from nitrogen, oxygen, or sulfur;

$R^3$ is an optionally substituted group selected from $C_{3-7}$ cycloaliphatic, a 6-10 membered monocyclic or bicyclic aromatic carbocyclic ring, or a 5-10 membered monocyclic or bicyclic saturated, partially unsaturated, or aromatic ring having 1-4 heteroatoms independently selected from nitrogen, oxygen, or sulfur;

n is 0-4;

each $R^4$ is independently selected from halogen, CN, R, OR, SR, $N(R)_2$, C(O)R, C(O)OR, $C(O)N(R)_2$, N(R)C(O)R, OC(O)R, $SO_2R$, $SO_2N(R)_2$, $N(R)SO_2R$, or $N(R)C(O)N(R)_2$;

m is 0-2; and each $R^5$ is independently selected from halogen, CN, R, OR, SR, or $N(R)_2$;

or:

$R^1$ is an optionally substituted group selected from $C_{1-6}$ aliphatic, $C_{3-7}$ cycloaliphatic, a 6-10 membered monocyclic or bicyclic aromatic carbocyclic ring, or a 5-10 membered monocyclic or bicyclic saturated, partially unsaturated, or aromatic ring having 1-4 heteroatoms independently selected from nitrogen, oxygen, or sulfur;

each R is independently hydrogen or an optionally substituted $C_{1-6}$ aliphatic group, or:

two R groups on the same nitrogen are taken together with the nitrogen atom to form a 4-7 membered saturated, partially unsaturated, or aromatic ring having 1-4 heteroatoms independently selected from nitrogen, oxygen, or sulfur;

$R^2$ is an optionally substituted group selected from $C_{3-7}$ cycloaliphatic, a 6-10 membered monocyclic or bicyclic aromatic carbocyclic ring, or a 5-10 membered monocyclic or bicyclic saturated, partially unsaturated, or aromatic ring having 1-4 heteroatoms independently selected from nitrogen, oxygen, or sulfur;

$R^3$ is an optionally substituted group selected from $C_{3-7}$ cycloaliphatic, a 6-10 membered monocyclic or bicyclic aromatic carbocyclic ring, or a 5-10 membered monocyclic or bicyclic saturated, partially unsaturated, or aromatic ring having 1-4 heteroatoms independently selected from nitrogen, oxygen, or sulfur;

n is 1-4;

each $R^4$ is independently selected from halogen, CN, optionally substituted $C_{1-6}$ aliphatic, OR, SR, $N(R)_2$, C(O)R, C(O)OR, $C(O)N(R)_2$, N(R)C(O)R, OC(O)R, $SO_2R$, $SO_2N(R)_2$, $N(R)SO_2R$, or $N(R)C(O)N(R)_2$;

m is 0-2; and each $R^5$ is independently selected from halogen, CN, R, OR, SR, or $N(R)_2$;

or:

$R^1$ is an optionally substituted group selected from $C_{1-6}$ aliphatic, $C_{3-7}$ cycloaliphatic, a 6-10 membered monocyclic or bicyclic aromatic carbocyclic ring, or a 5-10 membered monocyclic or bicyclic saturated, partially unsaturated, or aromatic ring having 1-4 heteroatoms independently selected from nitrogen, oxygen, or sulfur;

each R is independently hydrogen or an optionally substituted $C_{1-6}$ aliphatic group, or:

two R groups on the same nitrogen are taken together with the nitrogen atom to form a 4-7 membered saturated, partially unsaturated, or aromatic ring having 1-4 heteroatoms independently selected from nitrogen, oxygen, or sulfur;

$R^2$ is an optionally substituted group selected from $C_{3-7}$ cycloaliphatic, a 6-10 membered monocyclic or bicyclic aromatic carbocyclic ring, or a 5-10 membered monocyclic or bicyclic saturated, partially unsaturated, or aromatic ring having 1-4 heteroatoms independently selected from nitrogen, oxygen, or sulfur;

$R^3$ is an optionally substituted group selected from $C_{3-7}$ cycloaliphatic, a 6-10 membered monocyclic or bicyclic aromatic carbocyclic ring, or a 5-10 membered monocyclic or bicyclic saturated, partially unsaturated, or aromatic ring having 1-4 heteroatoms independently selected from nitrogen, oxygen, or sulfur;

n is 0-4;

each $R^4$ is independently selected from halogen, CN, R, OR, SR, $N(R)_2$, C(O)R, C(O)OR, $C(O)N(R)_2$, N(R)C(O)R, OC(O)R, $SO_2R$, $SO_2N(R)_2$, $N(R)SO_2R$, or $N(R)C(O)N(R)_2$;

m is 1-2; and each $R^5$ is independently selected from halogen, CN, optionally substituted $C_{1-6}$ aliphatic, OR, SR, or $N(R)_2$, or:

$R^1$ is an optionally substituted group selected from $C_{1-6}$ aliphatic, $C_{3-7}$ cycloaliphatic, a 6-10 membered monocyclic or bicyclic aromatic carbocyclic ring, or a 5-10 membered monocyclic or bicyclic saturated, partially unsaturated, or aromatic ring having 1-4 heteroatoms independently selected from nitrogen, oxygen, or sulfur;

each R is independently hydrogen or an optionally substituted $C_{1-6}$ aliphatic group, or:

two R groups on the same nitrogen are taken together with the nitrogen atom to form a 4-7 membered saturated, partially unsaturated, or aromatic ring having 1-4 heteroatoms independently selected from nitrogen, oxygen, or sulfur;

$R^2$ is an optionally substituted group selected from $C_{3-7}$ cycloaliphatic, a 6-10 membered monocyclic or bicyclic aromatic carbocyclic ring, or a 5-10 membered monocyclic or bicyclic saturated, partially unsaturated, or aromatic ring having 1-4 heteroatoms independently selected from nitrogen, oxygen, or sulfur;

$R^3$ is an optionally substituted 5-10 membered monocyclic or bicyclic saturated, partially unsaturated, or aromatic ring having 1-4 heteroatoms independently selected from nitrogen, oxygen, or sulfur;

n is 0-4;

each $R^4$ is independently selected from halogen, CN, R, OR, SR, $N(R)_2$, C(O)R, C(O)OR, $C(O)N(R)_2$, N(R)C(O)R, OC(O)R, $SO_2R$, $SO_2N(R)_2$, $N(R)SO_2R$, or $N(R)C(O)N(R)_2$;

m is 0-2; and each $R^5$ is independently selected from halogen, CN, R, OR, SR, or $N(R)_2$, or:

$R^1$ is an optionally substituted group selected from $C_{1-6}$ aliphatic, $C_{3-7}$ cycloaliphatic, a 6-10 membered monocyclic or bicyclic aromatic carbocyclic ring, or a 5-10 membered monocyclic or bicyclic saturated, partially unsaturated, or aromatic ring having 1-4 heteroatoms independently selected from nitrogen, oxygen, or sulfur;

each R is independently hydrogen or an optionally substituted $C_{1-6}$ aliphatic group, or:

two R groups on the same nitrogen are taken together with the nitrogen atom to form a 4-7 membered saturated, partially unsaturated, or aromatic ring having 1-4 heteroatoms independently selected from nitrogen, oxygen, or sulfur;

$R^2$ is an optionally substituted 5-10 membered monocyclic or bicyclic aromatic ring having 1-4 heteroatoms independently selected from nitrogen, oxygen, or sulfur;

$R^3$ is an optionally substituted group selected from $C_{3-7}$ cycloaliphatic, a 6-10 membered monocyclic or bicyclic aromatic carbocyclic ring, or a 5-10 membered monocyclic or bicyclic saturated, partially unsaturated, or aromatic ring having 1-4 heteroatoms independently selected from nitrogen, oxygen, or sulfur;

n is 0-4;

each $R^4$ is independently selected from halogen, CN, R, OR, SR, $N(R)_2$, C(O)R, C(O)OR, $C(O)N(R)_2$, N(R)C(O)R, OC(O)R, $SO_2R$, $SO_2N(R)_2$, $N(R)SO_2R$, or $N(R)C(O)N(R)_2$;

m is 0-2; and each $R^5$ is independently selected from halogen, CN, R, OR, SR, or $N(R)_2$.

Exemplary compounds are set forth in Table 1, below.

TABLE 1

Exemplary Compounds

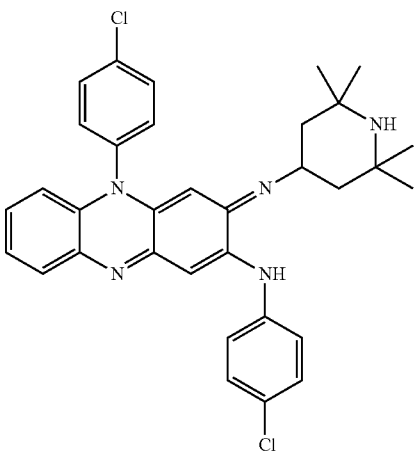 [SMILES: CC1(C)CC(N=c2cc3n(-c4ccc(Cl)cc4)c4ccccc4nc-3cc2Nc2ccc(Cl)cc2)CC(C)(C)N1]

TABLE 1-continued

Exemplary Compounds

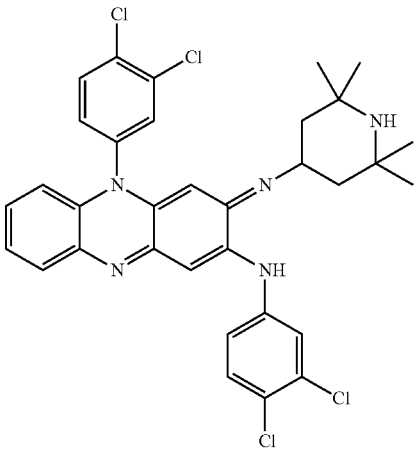 [SMILES: CC1(C)CC(N=c2cc3n(-c4ccc(Cl)c(Cl)c4)c4ccccc4nc-3cc2Nc2ccc(Cl)c(Cl)c2)CC(C)(C)N1]

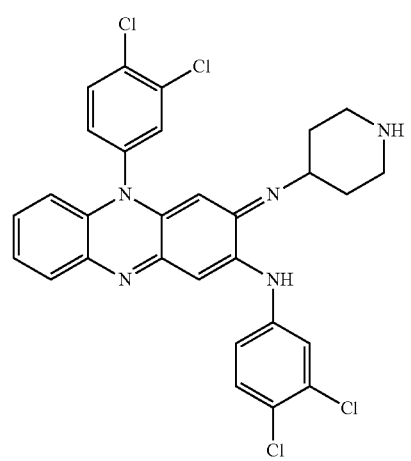 [SMILES: Clc1ccc(Nc2cc3nc4ccccc4n(-c4ccc(Cl)c(Cl)c4)c-3cc2=NC2CCNCC2)cc1Cl]

TABLE 1-continued
Exemplary Compounds
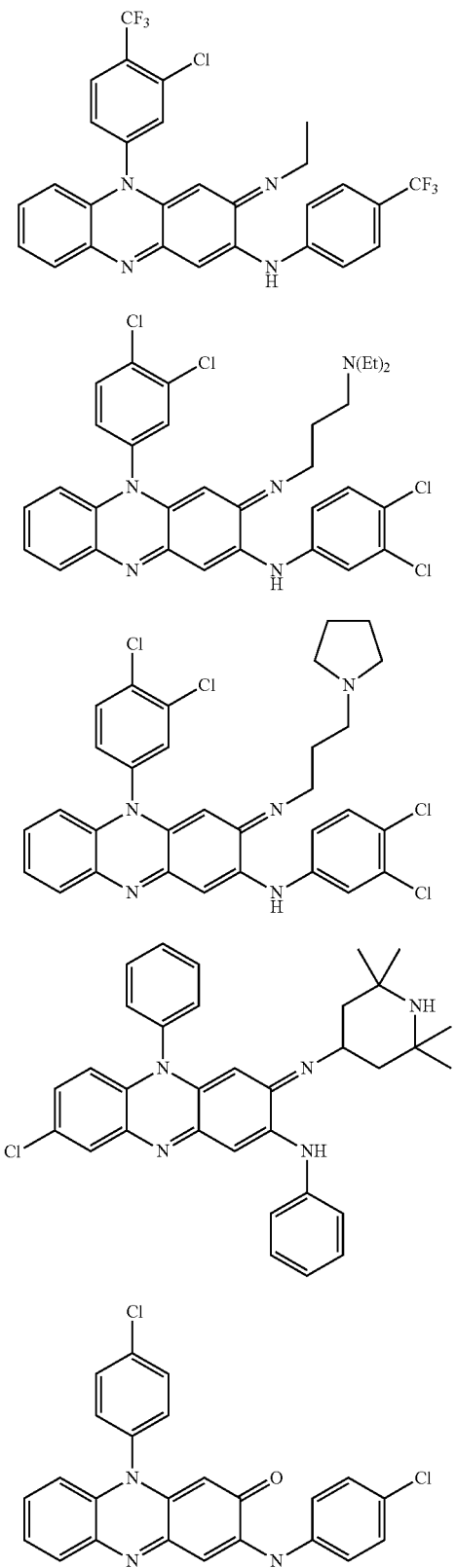
Additional exemplary compounds are set forth in Table 2, below.
TABLE 2
Exemplary Compounds
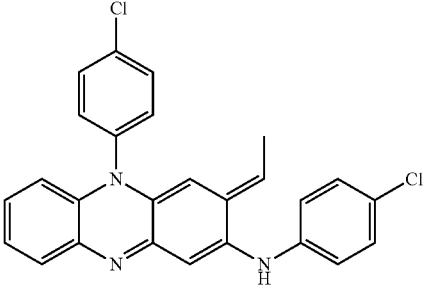 [SMILES: C/C=c1\cc2c(cc1Nc1ccc(Cl)cc1)=Nc1ccccc1N2c1ccc(Cl)cc1]

TABLE 2-continued
Exemplary Compounds
I-16
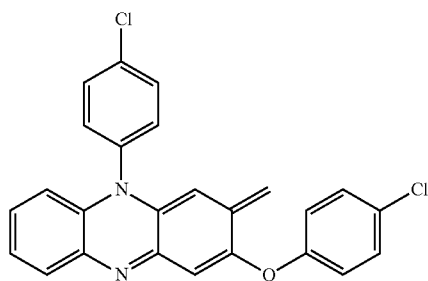 [SMILES: C=c1cc2c(cc1Oc1ccc(Cl)cc1)=Nc1ccccc1N2c1ccc(Cl)cc1]
I-17
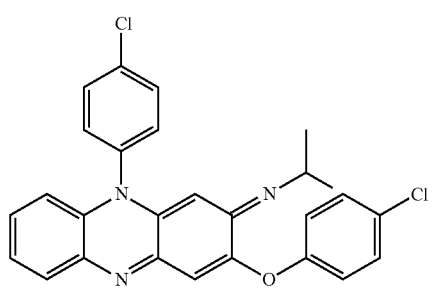 [SMILES: CC(C)N=c1cc2n(-c3ccc(Cl)cc3)c3ccccc3nc-2cc1Oc1ccc(Cl)cc1]
I-18
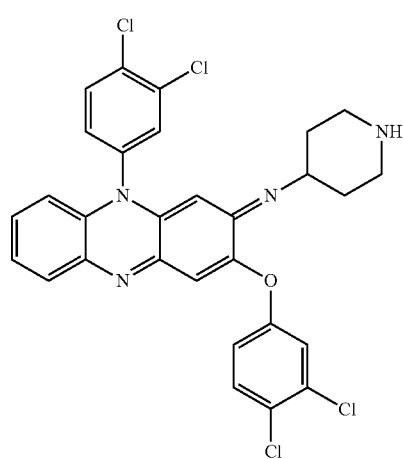 [SMILES: Clc1ccc(Oc2cc3nc4ccccc4n(-c4ccc(Cl)c(Cl)c4)c-3cc2=NC2CCNCC2)cc1Cl]
I-19
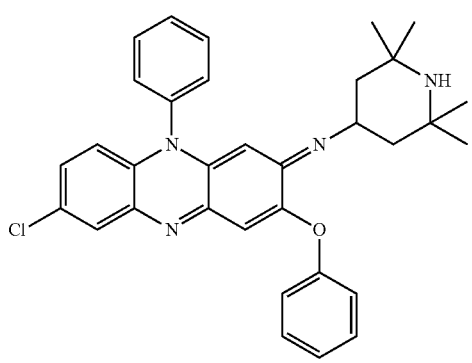 [SMILES: CC1(C)CC(N=c2cc3n(-c4ccccc4)c4ccc(Cl)cc4nc-3cc2Oc2ccccc2)CC(C)(C)N1]
TABLE 2-continued
Exemplary Compounds
I-20
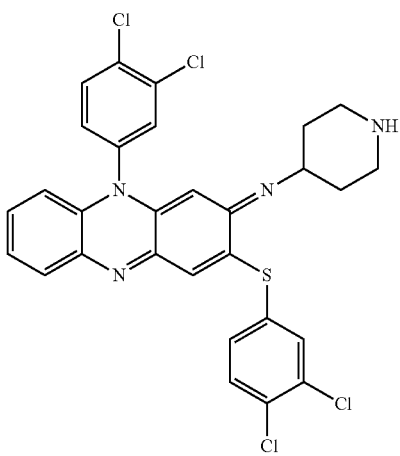
I-21
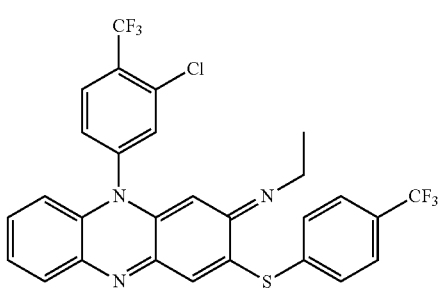 [SMILES: CCN=c1cc2n(-c3ccc(C(F)(F)F)c(Cl)c3)c3ccccc3nc-2cc1Sc1ccc(C(F)(F)F)cc1]
I-22
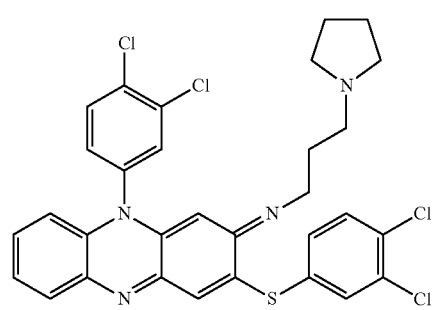 [SMILES: Clc1ccc(Sc2cc3nc4ccccc4n(-c4ccc(Cl)c(Cl)c4)c-3cc2=NCCCN2CCCC2)cc1Cl]
I-23
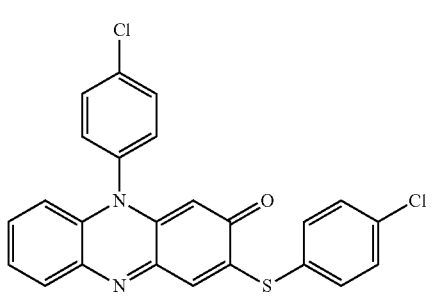 [SMILES: O=c1cc2n(-c3ccc(Cl)cc3)c3ccccc3nc-2cc1Sc1ccc(Cl)cc1]

TABLE 2-continued
Exemplary Compounds
I-24
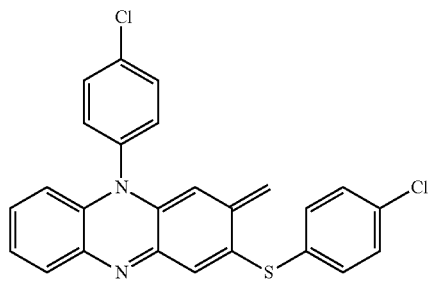 [SMILES: C=c1cc2c(cc1Sc1ccc(Cl)cc1)=Nc1ccccc1N2c1ccc(Cl)cc1]
I-25
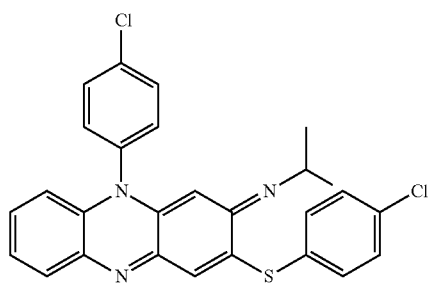 [SMILES: CC(C)N=c1cc2n(-c3ccc(Cl)cc3)c3ccccc3nc-2cc1Sc1ccc(Cl)cc1]
I-26
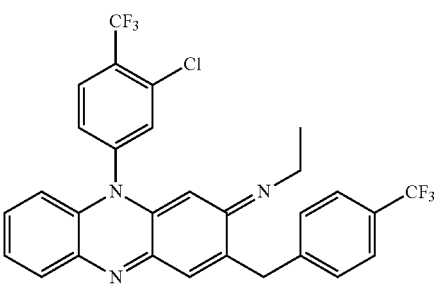 [SMILES: CCN=c1cc2n(-c3ccc(C(F)(F)F)c(Cl)c3)c3ccccc3nc-2cc1Cc1ccc(C(F)(F)F)cc1]
I-27
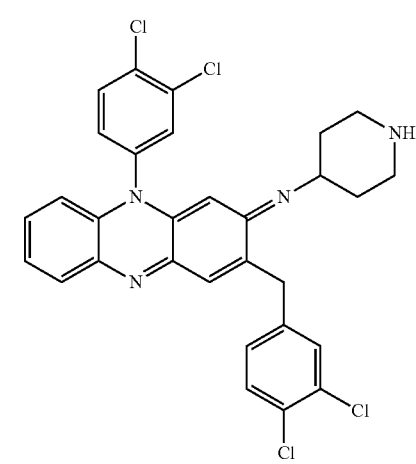 [SMILES: Clc1ccc(Cc2cc3nc4ccccc4n(-c4ccc(Cl)c(Cl)c4)c-3cc2=NC2CCNCC2)cc1Cl]
TABLE 2-continued
Exemplary Compounds
I-28
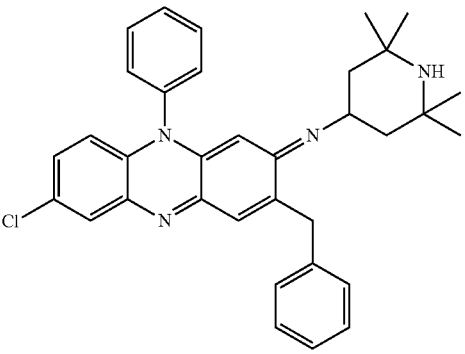 [SMILES: CC1(C)CC(N=c2cc3n(-c4ccccc4)c4ccc(Cl)cc4nc-3cc2Cc2ccccc2)CC(C)(C)N1]
I-29
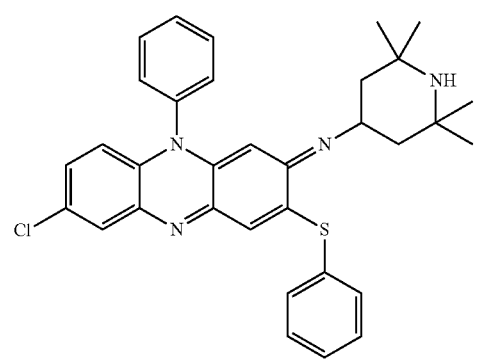 [SMILES: CC1(C)CC(N=c2cc3n(-c4ccccc4)c4ccc(Cl)cc4nc-3cc2Sc2ccccc2)CC(C)(C)N1]
I-30
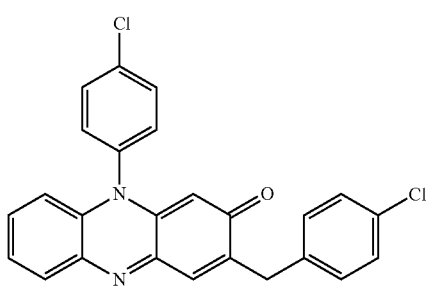 [SMILES: O=c1cc2n(-c3ccc(Cl)cc3)c3ccccc3nc-2cc1Cc1ccc(Cl)cc1]
I-31
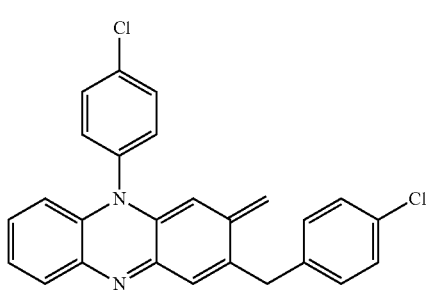

TABLE 2-continued

Exemplary Compounds

I-32

I-33

I-34

I-35

In certain embodiments, the present invention provides a compound depicted in Table 1, or a pharmaceutically acceptable salt thereof. In certain embodiments, the present invention provides a compound depicted in Table 2, or a pharmaceutically acceptable salt thereof 4. Clofazimine Clofazimine (CLF), also referred to herein as compound I-1:

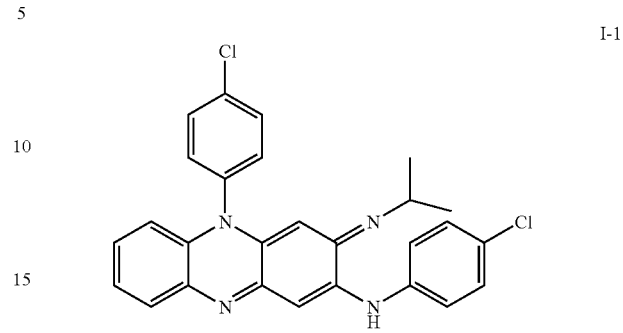

is a drug which has been shown to be effective for treatment of leprosy (also known as Hansen's disease) (Arbiser et al. *J. Am. Acad. Dermatol.* 1995. 32: 241-247). The standard dosing of CLF for leprosy is a 300 mg loading dose once a month followed by 100 mg daily as part of a mult-drug regimen ("Chemotherapy of leprosy" WHO Study Group. Word Health Organization, Geneva. 1993). Clofazimine is known to have three metabolites which account for only a small amount of the excreted drug: 3-(p-hydroxyanilino)-10-(p-chlorophenyl)-2,10-dihydro-2-isopropylimino-phenazine, 3-(β-D-glucopyransiduronic acid)-10-(p-chlorophenyl)-2,10-dihyrdo-2-isopropylimino-phenzine) and 3-(p-chloroanilino)-10-(p-chlorophenyl)-4,10-dihyrdo-4-(β-D-glucopyranosiduronic acid)-2-isopropyliminiophenzine (Holdiness. *Clinical Pharmacokinetics.* 1989. 16: 74-85). In some embodiments, the present invention provides an active metabolite of clofazimine, or another provided compound. In certain embodiments, such an active metabolite is also useful for treating a disorder associated with Kv1.3 activation, as described herein.

Several groups have synthesized compounds chemically related to clofazimine (Zeis, B. M., et al., *Antimicrobial Agents and Chemotherapy* 1987. 31:789-793; Fransblau, S. G. and O'Sullivan, J. F., *Antimicrobial Agents and Chemotherapy* 1988. 32:1583-1585; O'Sullivan, J. F., et al., *Journal of Medicinal Chemistry* 1988. 31:567-572; Fransblau, S. G., et al., *Antimicrobial Agents and Chemotherapy* 1989. 33:2004-2005; O'Conner, R., et al., *Drug Metabolism Reviews* 1995. 27:591-614; Reddy, V. M., et al., *Journal of Antimicrobial Chemotherapy* 1999. 43:615-623; van Rensburg, C. E. J., et al., *Chemotherapy* 2000. 46:43-48; Huygens F., et al., *Chemotherapy* 2005. 51:263-267; U.S. Pat. Nos. 2,891,062; 2,943,089; 2,946,792; 2,948,726; 3,080,283; 3,375,251; 3,455,926; 3,499,899; 3,592,814; 3,822,265; 5,763,442; 5,763,443; WO2003007957).

There have been a number of competing hypotheses about the mechanisms by which CLF acts on mycobacteria. Clofazimine was first hypothesized to exhibit its antimicrobial activity by binding to high G+C content DNA (Morrison, N. E., et al. *Int. J. Lepr.* 1976. 44:133-134; Morrison, N. E., et al. *Int. J. Lepr.* 1976. 44:475-481). Another proposed mechanism was through a redox cycle where CLF is reduced by the mitochondria of cells (inhibiting respiration), and then oxidized to produce hydrogen peroxide (Delhanty J. D. A., et al. *Br. J. Exp. Path.* 1974. 55:13-19; Rhodes, P. M. and Wilkie, D. *Biochem. Pharmacol.* 1973. 22:1047-1056). More recent observations demonstrating inhibition of potassium influx in mycobacteria showed that calcium influx was unaffected, and the explanation for this observation was suggested to be the inhibition of Na$^+$, K$^+$-ATPase or the KDP system (Steel, H. C., et al. *Journal of Antimicrobial Therapy.* 1999. 44:209-216; Cholo, M. C. et al. *Journal of Antimicrobial Chemotherapy.* 2006. 57:79-84).

Clofazimine has also been observed to have both pro- and anti-inflammatory effects on the immune system, with competing hypothesized mechanisms (Arbiser, J. L. and Moschella S. L., *J Am Acad Dermatol.* 1995. 32:241-247; O'Connor, R., et al. *Drug Metabolism Reviews.* 1995. 27:591-614). Anti-inflammatory effects which have been observed include a dose-dependent inhibition of neutrophil migration and activated lymphocyte proliferation (van Rensburg, C. E. J., et al. *Antimicrobial Agents and Chemotherapy.* 1982. 21:693-697; Anderson, R., et al. *Int. J. Immunopharmac.* 1986. 8:605-620). Pro-inflammatory effects include stimulation of myeloperoxidase-mediated iodination, phagocytosis, release of lysosomal enzymes, and generation of more superoxide radicals (Zeis, B. M., et al. *Antimicrobial Agents and Chemotherapy* 1987. 31:789-793, Sahu, A., et al. *Int. J. Immunopharmac.* 1992. 4:721-730). One more theory of CLF's anti-inflammatory effects on the immune system involved CLF causing the production of lysophospholipids in lymphocytes. These lysophospholipids were posited to be formed after indirect stimulation of phospholipase A$_2$ (PLA2), and those lipids were hypothesized to then inhibit the Na$^+$, K$^+$-ATPase and therefore inhibit activated lymphocyte proliferation (Anderson, R., et al. *Biochemical Pharmacology.* 1993. 11:2029-2038; Van Rensburg, C. E. J., et al. *Cancer Research.* 1993. 53: 318-323).

The mechanisms hypothesized in the previous paragraphs do not suggest and are potentially at odds with the hypothesis that clofazimine inhibits the potassium channel Kv1.3 and diseases mediated by Kv1.3. The hypothesis that CLF mediates its anti-inflammatory effects by activation of PLA2 and lysophospholipids is at odds with research showing that lysophospholipids produced by lymphocytes are proinflammatory and that blocking PLA2 is effective in treating an animal model of multiple sclerosis (Asaoka, Y., et al. *PNAS.* 1992. 89:6447-6451; Kalyvas, A. and David, S, *Neuron.* 2004. 41:323-35). In addition, calcium influx has been shown to activate forms of PLA2 (Chang, W. et al. *FASEB J.* 2006. 20:E1681-E1693), while a Kv1.3 inhibitor would prevent calcium influx. Finally, inhibitors of PLA2 suppress calcium ionophore and mitogen induced expression of IL-2 (Burgermeister et al. *European Journal of Pharmacology* 2003. 466: 169-180), which contradicts the theory that CLF as an activator of PLA2 would be anti-inflammatory. Taken as a whole, the myriad of competing mechanism hypothesis and potentially conflicting data would make the hypothesis and any observations of CLF as a Kv1.3 inhibitor a novel finding.

In addition to being used to treat leprosy, CLF has been reported to have been used both in single patient case studies as well as multi-patient clinical trials. CLF has been used as a treatment for several infectious conditions including *M. uclerans* (Katoch et al. *Indian Journal of Medical Research.* 2004. 120:290-304), Psittacosis (Macheta et al. *Journal of Infection.* 1994. 28: 69-71), Lobo Disease (Silvad et al. *Bulletin De La Societe De Pathologie Exotique.* 1978. 71: 409-412), tuberculosis (Senaratne W V. *Ceylon Med J.* 2004. 49:86-87; Van Deun et al. *Int J Tuberc Lung Dis.* 2004. 8:560-7), rhinoscleroma (Sehta et al. *J Laryngol Otol.* 1989. 103:856-860), leishmaniasis (Evans et al. *Ann. Trop. Med. Parasitol.* 1989. 103:856-860) and cutaneous malacoplakia which is a rare disease that is hypothesized to be the result of bacterial death (Herror et al. *J Am Acad Dermatol.* 1990: 947-948). In addition, clofazimine was tried unsuccessfully to prevent *Mycobacterium avium* complex disease in HIV infected individuals (Abrams et al. *Journal of Infectious Disease.* 1993. 167:1459-1463).

Groups have hypothesized that mycobacteria infection could be the cause of Crohn's disease and therefore have used clofazimine either as a single agent or as part of a multi-drug regimen with mixed results. In a placebo controlled study with 20 subjects over the course of six months, clofazimine appeared to prevent disease relapse (Kelleher D. et al. *Gut.* 1982. 23:A449-A450). However, in a placebo controlled trial with 213 patients over a 36 month period in which patients received clofazimine as part of a multi-drug regiment against *mycobacterium avium* paratuberculosis, the intervention failed to produce sustained benefit (Selby et al. *Gastroenterology.* 2007. 132: 2313-2319).

Reports exist documenting the use of clofazimine to treat a number of very rare diseases whose etiology is poorly understood including pyoderma gangrenosum (Milika R B et al. *Int J. Dermatol.* 2002. 41:65-8; Wollina U. *Am J Clin Dermatol.* 2002.3:149-58), Acne agminata (Seukeran D. et al. *British Journal of Dermatology.* 1999. 141:596-597), Sweet's syndrome (Cohen et al. *Orphanet J Rare Dis.* 2007. 2:34.), Melkersson-Rosenthal Syndrome (Horsteini et al. *Journal of Dermatology.* 1997. 24: 281-296), cheilitis granulomatosa associated with Melkersson-Rosenthal Syndrome (Goncalves et al. *Brazilian Journal of Otorhinolaryngology.* 2007. 73: 138-139; Galley et al. *Annales De Dermatologie Et De Venerlogie.* 1989. 116:241-244, Fdez-Freire et al. *J Drugs Dermatol.* 2005. 4:374-7), Weber-Christian Disease (Abuzahara, F. *British Journal of Dermatology.* 2005. 152: 565-566), Rothmann-Makai (Wollina et al. *Acta Derm Venereol.* 1996. 76:77-79), scleroma and necrobiosis lipoidica (Shehata. *J Laryngol Otol.* 1989 103:856-860), granuloma annulare and necrobiosis lipoidica (Mensing. *Hautarzt.* 1989. 40:99-103), granuloma faciale (La Fuente. *Acta Dermato-Venereologica.* 2000. 80:144), laryngeal sarcoidosis (Ridder et al. *Annals of Otology Rhinology and Laryngology.* 2000. 109:1146-1149), and erythema dyschromicium perstans (Piqueromatrin et al. *International Journal of Dermatology.* 1989. 28: 198-200). Clofazimine has been tried unsuccessfully for the treatment of vitiligo (Shukla et al. *Dermatologica.* 1981. 163: 169-171). In addition to use as a human therapeutic, clofazimine has been tried for treatment of equine fistulous withers (Knottenbelt et al. *Vet Rec.* 1989. 11:509-510). There is no common thread or mechanism that tie together all of the uses of clofazimine for the various rare diseases with poorly understood mechanisms. However, few of the diseases have approved therapies which produce the desired clinical effects. Therefore, as with a number of other agents, clofazimine was used in the hope that it might produce a therapeutic outcome.

Clofazimine has also been tried as a therapy for treatment for various forms of cancer, including multidrug resistant cancer (U.S. Pat. No. 5,763,443). Clofazimine was suggested to be a potential treatment for lung cancer based on results using a cancerous cell line (Sri-Pathmanathan et al. *International Journal of Cancer.* 1994. 56:900-905) and a xenograft model (Van Rensburg. *Cancer Lett.* 1994. 85:59-63). In two clinical studies of liver cancer, clofazimine produced mixed results with no significant remission of the disease, but may have stabilized some patients (Ruff P et al. *Ann Oncol.* 1998. 9:217-219; Falkson, C I et al. *Oncology.* 1999. 57:232-235). Better results were reported in a rat model of liver cancer using a lipiodol formulation (Pourgholami M H et al. 2004.207:37-47). Clofazimine has also been suggested as a treatment for chronic myeloid leukemia (Brandt L. *Scand J Haemotol.* 1972. 9:159-66).

Several case reports exist on the use of clofazimine to treat pustular psoriasis (Nair & Shereef. *Int J. Dermatol.* 1991. 30:151; Rubisz-Brzezńska et al. *Przegl Dermatol.* 1982. 69:75-78; Chuaprapaisilp & Piamphongsant. *Br J Dermatol.* 1978.99:303-5; (Molin. *Acta Derm Venereol.* 1975.55:151-3) and a report exists on treatment of impetigo herpetiformis which may be related to pustular psoriasis (Rubisz-Brzezińska et al. *Przegl Dermatol.* 1981. 68:505-9). Pustular psoriasis is characterized by pustules filled with pus which are not caused by infection. Pustular psoriasis itself is generally thought of as having distinct forms including von Zumbusch pustular psoriasis which is characterized by a sudden outbreak of pustules, dehydration, anemia, weight loss, muscle weakness and other serious complications and can be life threatening in nature ("Specific Forms of Psoriasis" 2006. National Psoriasis Foundation), and palmo-plantar pustulosis which is characterized by pustules on the palms of the hand and soles of the feet ("Specific Forms of Psoriasis" 2006. National Psoriasis Foundation). The disease cycles between fewer to more pustules for reasons that are not clear. A third form of pustular psoriasis is acropustulosis (also known as acrodermattis continua of Hallopeau) which is characterized by pustules on the palms and soles of infants and often self-resolves with time ("Specific Forms of Psoriasis" 2006. National Psoriasis Foundation).

The various forms of pustular psoriasis clearly differ in terms of the timing of the disease manifestations from the sudden onset of von Zumbusch to the chronic nature of palmo-plantar and the self-resolving acropustulosis. The etiology of the various forms of pustular psoriasis remains murky, but various risk factors have been documented which vary between the various forms of pustular psoriasis. For instance, withdrawal of corticosteroids has been associated with von Zumbusch and smoking with outbreaks of acropustulosis ("Specific Forms of Psoriasis" 2006. National Psoriasis Foundation). Certain agents such as methotrexate have been used to successfully treat both von Zumbusch pustular psoriasis and palmo-plantar pustular psoriasis, but treatment protocols differ for the various pustular psoriasis diseases (e.g., for von Zumbusch pustular psoriasis medical care must be given immediately with treatments including rehydration while little treatment may be employed for acropustulosis which tends to completely self-resolve when an infant turns three) ("Specific Forms of Psoriasis" 2006. National Psoriasis Foundation). Therefore, one cannot a priori conclude that a new therapy which is appropriate for one type of pustular psoriasis will be appropriate for another type of pustular psoriasis.

While the differences between the various types of pustular psoriasis are striking, the difference between pustular psoriasis and plaque psoriasis is even greater. In contrast to pustules, plaques psoriasis is characterized by plaque lesions that often have a scale like appearance. Plaque and pustular psoriasis are considered separate diseases for regulatory purposes by the Food & Drug Administration (FDA) and therefore a drug which has successfully passed a pivotal trial using plaque psoriasis patients will only get approval for plaque psoriasis and not pustular psoriasis. For instance, alefacept (brand name Amevive) underwent clinical trials for plaque psoriasis and was approved only for plaque psoriasis by the FDA (Amevive package insert. 2006. Astellas Pharma US, Inc.). While the biological agent infliximab against tumor necrosis factor (TNF) has been successfully used for treatment of plaque psoriasis (Gisondi & Girolomoni et al. *Autoimmun Rev.* 2007.6:515-9) and case reports exist suggesting its efficacy for pustular psoriasis (Weishaupt et al. *J Dtsch Dermatol Ges.* 2007. 5:397-9) infliximab has actually been documented in numerous cases to cause pustular psoriasis (Thurber M et al. *J. Drugs Dermatol.* 2004. 3:439-440; Wollina et al. *Am J Clin Dermatol.* 2008.9:1-14). The paradoxical effects of infliximab and other anti-TNF agents suggests pustular and plaque psoriasis have different underlying mechanisms. The underlying cause of plaque psoriasis is generally thought to involve actions of T-cells which exert a pathological effect, but other immune cells such as dedritic cells, macrophages and keratinocytes may also be involved (Sabat et al. *Experimental Dermatology.* 2007. 16:779-798). In pustular psoriasis, neutrophils are found in the pustular lesions where they may contribute to the pathology of the disease together with a distinct set of T-cells that produce the cytokines CXCL8 and GM-CSF (Keller et al. *The Journal of Immunology.* 2005. 175: 7678-76786). Thus, while both pustular psoriasis and plaque psoriasis are both autoimmune diseases, different subsets of immune cells may be involved in causing the observed disease pathology.

Clofazimine has also been used to treat graft versus host disease in an open label study which resulted in ~25% of patients being able to decrease the amount of other medication the patients were taking (Lee et al. *Blood.* 1997. 7:2298-2302). In addition, clofazimine has been shown to have positive effects on lupus (Bezerra et al. 2005. *Arthritis Rheum.* 2005. 52:3073-8; Krivanek et al. *Australas J Dermatol.* 1976. 17:108-10; Pandhi et al. *Int J Dermatol.* 1978. 17:492-3; Krivanek & Paver. *Australas J Dermatol.* 1980. 21:169; Crovato & Levi. *Arch Dermatol.* 1981. 117:249-50). Although both graft versus host disease and lupus are considered autoimmune diseases, the symptoms of the disease are believed to be the result of dysfunction of different parts of the immune system. For instance, graft versus host disease is thought to result from the pathological actions of T-cells generated by the graft which then attack the host (Sun et al. *Transl Res.* 2007.150:197-214.), whereas lupus is a complex disease with both a B-cell and T-cell components (Rahman and Isenberg. *The New England Journal of Medicine.* 2008. 358: 929-939). Given the significant differences between the two diseases, it is not clear a priori that a drug that would work for one disease would work for the other or for other autoimmune diseases.

The intracellular TCR-mediated signal transduction pathway leading to IL-2 transcription is essential for the activation of quiescent T-cells and as such has served as a reliable model system to discover and evaluate immunosuppressive agents. In addition to the discovery of FK506 using this model system, other immunosuppressive agents have been discovered from different chemical libraries. By screening a library of chemical compounds, clofazimine was identified as a novel inhibitor of this signaling pathway. Further mechanistic deconvolution by systematically examining the known steps in this signaling pathway led to identification of Kv1.3 as a physiologically relevant target for clofazimine. The selective inhibition of Kv1.3 by clofazimine accounts for the perturbation of calcium oscillation patterns by the drug and the different effects of clofazimine on the intrinsic enzymatic activity of calcineurin in vitro and the calcineurin-mediated NFAT dephosphorylation in cell culture.

Although clofazimine does have a number of side effects including GI and skin discoloration, it is well tolerated and relatively safe. In particular, it lacks the nephrotoxicity and neurotoxicity associated with both CsA and FK506. As such, clofazimine has great potential in the treatment of autoimmune diseases such as multiple sclerosis, type 1 diabetes and psoriasis as well as organ transplantation. The fact that clofazimine, unlike other known inhibitors of Kv1.3, has been used in humans for decades may accelerate its clinical evaluation and eventual introduction as new treatments for different autoimmune and other pertinent diseases.

The clinically administered formulation of clofazimine is an orally administered soft gelatin capsule that contains micronized solid drug particles suspended in an oil-wax base (Lamprene®, Novartis). The extent of clofazimine absorption and bioavailability from this formulation is generally recognized to sub-optimal (Narang & Srivastava. *Drug Development and Industrial Pharmacy*. 2002. 28:1001-1013). Multiple alternative strategies have been proposed for the formulation of hydrophobic drugs such as clofazimine. To date, however, none of these other formulations have been adopted for clofazimine in the clinical setting.

One proposed approach entails suspension of clofazimine in a solid emulsifying or emulsion-stabilizing polymer, where optimization of various aspects can be performed, such as polymer molecular weight or drug: carrier weight ratios (WO08030469A2; WO07115381A2; Kailasam et al. *The Journal of Antimicrobial Chemotherapy*. 1994 3:273-279; Krishnan and Abraham. *Biopharmaceuticals and Drug Disposition*. 1994. 15:329-339; Narang and Srivastava. *Drug Development and Industrial Pharmacy*. 2002. 28:1001-1013; Vera et al. *Journal of Microencapsulation*. 2006. 23:686-697). A similar approach entails suspension of clofazimine in lipids or oils (WO07011940A2; Pourgholami et al. *Cancer Letters*. 2004.207:37-47). Parenteral, oral, or topical formulations of clofazimine within micelles or liposomes have also been proposed (WO05107712A1; Adams et al. *Antimicrobial Agents and Chemotherapy*. 1999. 41:1638-1643; Patel et al. *Die Pharmazie*. 1999. 54:448-451; Patel et al. *Journal of Microencapsulation*. 1999. 16:357-367; Salem et al. *Methods in Enzymology*. 2005. 391:261-291). Another approach entails the suspension of clofazimine in hydrophobic microparticles that are suspended within an otherwise hydrophilic tablet (U.S. Pat. No. 6,048,550). Other approaches include a novel lyophilization technique (Peters et al. *The Journal of Antimicrobial Chemotherapy*. 2000. 45:77-83), plasticization (U.S. Pat. No. 7,201,923), optimization of microsphere formulation size for size-dependent release (U.S. Pat. No. 6,264,991), implantable stents designed to elute the drug (WO07065016A2), and ionization of ionizable functional groups of clofazimine to enable complexation with surfactants and triglycerides (U.S. Pat. No. 6,383,471). Other proposed but impractical formulations of clofazimine have also been claimed or described in the literature, such as complexing of drugs such as clofazimine with ionic macromolecules for sustained release (WO07022255A2), among others (US20060018933A1). Thus, a need exists for alternative formulations of clofazimine.

5. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit Kv1.3 in a biological sample or in a patient. In certain embodiments, the amount of compound in compositions of this invention is such that is effective to measurably inhibit Kv1.3 in a biological sample or in a patient. In certain embodiments, a composition of this invention is formulated for administration to a patient in need of such composition. In some embodiments, a composition of this invention is formulated for oral administration to a patient.

The term "patient", as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

As used herein, the term "inhibitory metabolite or residue thereof" means that a metabolite or residue thereof is also an inhibitor of Kv1.3.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and $N^+(C_{1-4} alkyl)_4$ salts. This invention also envisions the quaternization of any basic nitrogen-containing groups of the compounds disclosed herein. Water or oil-soluble or dispersible products may be obtained by such quaternization.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, caplets, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

In certain embodiments, pharmaceutically acceptable compositions of this invention are formulated for oral administration.

Certain compounds of the present invention are hydrophobic, such as, for example, clofazimine. Various methods exist to reformulate hydrophobic drugs which could increase their bioavailability and improve their pharmacokinetics. For instance, clofazimine, or other compounds of the present invention, can be formulated with carbohydrate agents, such as cyclodextrin (Carrier et al. *Journal of Controlled Release.* 2007. 123:78-99), starch (U.S. Pat. No. 4,721,709), cellulose (U.S. Pat. Nos. 4,721,709; 5,741,524; 6,531,158; US20040224017A1), lactose (U.S. Pat. No. 6,531,158), chitosan (Qu et al. *Biomacromolecules.* 2006. 7:3452-3459; US20050226905A1), or a wide variety of carbohydrates (U.S. Pat. Nos. 5,500,227; 6,024,982; 6,294,192; 6,387,404; 6,451,339; US20050043272A1; US20050226905A1; WO08017839A1).

In another embodiment, clofazimine, or other compounds of the present invention, is formulated with biodegradable polymers (Musyanovych et al. *Macromolecular Bioscience.* 2008. 8:127-139; U.S. Pat. Nos. 5,266,332; 5,348,746; 5,500,227; 5,641,745; 5,736,159; 5,955,509; 6,024,982; 6,201,072; 6,207,197; 6,294,192; 6,337,092; 6,387,404; 6,387,409; 6,447,796; 6,451,339; 6,592,899; 6,702,995; 6,730,334; 6,855,331; 7,265,186; US20020036154A1; US20030157170A1; US20040224017A1; US 20050008704A1; US20050152979A1; US20050249799A1; US 20060057204A1; US20070048368A1; US 20080038333A1; US20080075785A1; US20080095856A1; US20080107749A1; WO9924490A1; WO05084639; WO07143290A2; WO08030591A2). As used herein, the term "biodegradable" as applied to polymers means polymers which are degradable in vivo either enzymatically or non-enzymatically to produce biocompatible or non-toxic by-products which can be further metabolized or excreted via normal physiological pathways. In a further embodiment, clofazimine, or other hydrophobic compounds of the present invention, is suspended within micelles formed by polymers (US20040005351A1). In another embodiment, clofazimine, or other hydrophobic compounds of the present invention, can be formulated with polymers in the presence of a reconstitution enhancing agent (US20050152979A1).

In another embodiment, clofazimine, or other compounds of the present invention, is formulated with oil-based compositions (U.S. Pat. Nos. 5,500,227; 5,645,856; 5,744,155; 5,891,845; 5,965,160; 5,980,939; 5,993,858; 6,024,982; 6,028,067; 6,063,762; 6,096,338; 6,187,747; 6,267,985; 6,294,192; 6,387,404; 6,761,903; US20040142040A1;

US20040213837A1; US20060073175A1; US20060292186A1; US20070048368A1; WO9929335A1).

In another embodiment, clofazimine, or other compounds of the present invention, is formulated with lipids (Gasco and Gasco, *Nanomedicine.* 2007. 2:955-960; Sachs-Bumble et al. *Advanced Drug Delivery Reviews.* 2008. 60:692-70; Ratanabanangkoon et al. *European Journal of Pharmaceutical Sciences.* 2008. 33:351-360; Trevaskis et al. *Advanced Drug Delivery Reviews.* 2008. 60:702-716; Charman & Stella. *International Journal of Pharmaceutics.* 1986. 34:175-178; U.S. Pat. Nos. 4,784,845; 4,816,247; 5,188,837; 5,364,632; 5,447,729; 5,478,860; 5,500,227; 5,576,016; 5,656,289; 5,681,585; 5,741,822; 5,993,858; 6,024,982; 6,187,747; 6,248,363; 6,267,985; 6,337,092; 6,383,471; 6,387,404; 6,387,409; 6,569,463; 6,599,527; 6,696,482; 6,761,903; 6,923,988; 6,982,281; 6,984,395; US20040001888A1; US20040126886A1; US20060051406A1; US20060078618A1; US20080124387A1; WO06113505A2; WO08049588A1). In a further embodiment, clofazimine, or other hydrophobic compounds of the present invention, is suspended within micelles formed by lipids (Mahmud et al. *Journal of Drug Targeting.* 2007. 15:553-584; U.S. Pat. Nos. 6,322,805; 6,616,941). In another embodiment, clofazimine, or other compounds of the present invention, is suspended within liposomes formed by lipids (U.S. Pat. No. 5,776,486; US20040126886A1; US20050244488A1; WO03105765A2). In another embodiment, clofazimine, or other compounds of the present invention, is suspended within chylomicrons formed partly by lipids (U.S. Pat. No. 5,656,289).

In another embodiment, clofazimine is formulated in self-emulsifying formulations (Perlman et al. *International Journal of Pharmaceutics.* 2008. 351:15-22; Kommuru et al. *International Journal of Pharmaceutics.* 2001. 212:233-246; Pouton. *European Journal of Pharmaceutical Sciences.* 2000. 11:S93-S98; Gursoy & Benita. *Biomedicine and Pharmacotherapy.* 2004. 58:173-182; U.S. Pat. No. 5,447,729; US 20020119198A1; US20040033257A1; US20040142040A1; US20050232952A1; US20060275358A1). In another embodiment, clofazimine, or other compounds of the present invention, is formulated to undergo fast dissolution in aqueous solution within the gastrointestinal tract (U.S. Pat. Nos. 5,500,227; 6,024,982; 6,387,404; US20070218128A1).

In another embodiment, clofazimine, or other compounds of the present invention, is formulated in an alcohol-based formulation (U.S. Pat. Nos. 5,843,891; 6,294,192; 6,982,281).

In another embodiment, clofazimine, or other compounds of the present invention, is formulated via coating with protein (US20070191473A1).

In another embodiment, clofazimine, or other compounds of the present invention, is formulated with an antioxidant, such as propyl gallate (U.S. Pat. No. 5,962,522).

In another embodiment, clofazimine, or other compounds of the present invention, is formulated or administered with a hydrophobic peptide (US20050288222A1).

In another embodiment, clofazimine, or other compounds of the present invention, is formulated with an organic solvent where clofazimine solubilization within the solvent is enabled by an amphiphilic material (U.S. Pat. No. 5,770,559) or the organic solvent is water-miscible (U.S. Pat. No. 6,682,758).

One solution to improve the pharmacokinetics of clofazimine is to form solid pharmaceutical formulations whereby, upon oral administration, the clofazimine is released with a slow, selectable rate.

Various techniques are known for formulating active ingredients to selectively control the resultant release rate of the drug. In another embodiment, clofazimine, or other compounds of the present invention, is formulated to be released on a sustained or extended basis (U.S. Pat. Nos. 4,869,904; 6,855,331; US20070048368A1).

The formulation of clofazimine, or other compounds of the present invention, include, but are not limited to, fast release, sustained release, continuous, as needed, short-term, rapid-offset, delayed release, and pulsatile release formulations (Landgraf et al. *Drug Delivery Technology.* 2005. 5: 48-55).

In one embodiment, the composition includes clofazimine, or other compounds of the present invention, and at least one controlled release agent. In another embodiment, the controlled release agent is a polymer that releases clofazimine, or other compounds of the present invention, by diffusion, in which clofazimine, or other compounds of the present invention, is encapsulated in a polymeric membrane or suspended within a polymer matrix. In another embodiment, the controlled release agent is a semi-permeable membrane containing an osmotic agent that releases clofazimine, or other compounds of the present invention, by solvent activation or increased pressure. In yet another embodiment, the controlled release agent is a degradable polymeric coat that degrades in a particular environment, for example, in a particular pH, and releases clofazimine, or other hydrophobic compounds of the present invention. In another embodiment, clofazimine, or other hydrophobic compounds of the present invention, is formulated to be released on a sustained or extended basis (U.S. Pat. Nos. 4,869,904; 6,855,331; US20070048368A1).

In a particular embodiment, clofazimine, or other compounds of the present invention, is incorporated in a controlled release matrix. Examples of materials suitable for inclusion in a controlled release matrix include one or more of water soluble polymers, water insoluble polymers, and fatty compounds. The term "water soluble polymer," as used herein, includes polymers which can be dissolved in water. Examples of such water soluble polymers include, but are not limited to, Eudragit RL, polyvinyl alcohol, polyvinylpyrrolidone, methyl cellulose, hydroxypropyl cellulose, hydroxypropylmethyl cellulose, polyethylene glycol and mixtures thereof.

The term "water insoluble polymer," as used herein, includes polymers which do not or only slightly dissolve in water. Examples of such water insoluble polymers include, but are not limited to, Eudragit RS, ethylcellulose, cellulose acetate, cellulose propionate (lower, medium or higher molecular weight), cellulose acetate propionate, cellulose acetate butyrate, cellulose acetate phthalate, cellulose triacetate, poly(methyl methacrylate), poly(ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), poly(ethylene), poly(ethylene) low density, poly(ethylene) high density, poly(propylene), poly(ethylene terephthalate), poly(vinyl isobutyl ether), poly(vinyl acetate), poly(vinyl chloride), polyurethane and a mixture thereof.

In one embodiment, the controlled release matrix includes one or more water soluble polymers. In another embodiment, the controlled release matrix includes one or more water insoluble polymers. In yet another embodiment, the controlled release matrix includes a combination of one or more water soluble and one or more water insoluble polymers. In a particular embodiment, the controlled release matrix includes a minor portion of one or more water insoluble polymers and a major portion of one or more water soluble polymers. In a certain embodiment, the controlled release matrix includes a minor portion of one or more water soluble polymers and a major portion of one or more water insoluble polymers. The ratio of water soluble and water insoluble polymers may be determined by the particular combination of polymers selected.

Clofazimine, or other compounds of the present invention, can be formulated as a controlled or sustained release oral formulation in any suitable tablet, coated tablet, or multiparticulate formulation known to those skilled in the art. The sustained release dosage form may optionally include a sustained released carrier which is incorporated into a matrix along with the clofazimine, or which is applied as a sustained release coating.

In some embodiments, the controlled release matrix includes one or more fatty compounds. Examples of fatty compounds include, but are not limited to, waxes generally (e.g., carnauba wax) and glyceryl tristearate.

An oral dosage form according to the invention may be provided as, for example, granules, spheroids, beads, and pellets or pills. These formulations are hereinafter collectively referred to as "multiparticulates" and/or particles. An amount of the multiparticulates that is effective to provide the desired dose of clofazimine over time may be placed in a capsule or may be incorporated in any other suitable oral solid form.

It is important for pharmaceutical formulation techniques to provide the capability of preselecting a desired release rate which can be tailored to the unique characteristics of clofazimine, or other hydrophobic compounds of the present invention. For example, many formulations permit selection of very slow release rates, i.e., sustained release formulations.

The suggested method of ingesting the current clinically available formulation of clofazimine, or in some embodiments other compounds of the present invention is that the patient takes the drug with food (Lamprene USA Drug Label. 1998. Novartis Pharmaceuticals Corporation). Following food intake, a higher stomach pH of 5-6 is achieved allowing for greater bioavailability of the drug. A delayed release formulation which allowed for release of clofazimine only following the stomach pH reaching 5-6 could improve bioavailability. Alternatively, a delayed release version which bypasses the stomach and starts release at the beginning of the small intestine, to allow for absorption through the intestinal lymphatic system could be particularly valuable for an agent that affects T-cell activity. In one embodiment, clofazimine is formulated to be released in environments other than the gastric environment, such as the pregastric environment (WO9938496A1), or the small intestine (U.S. Pat. No. 5,656, 289; US20040224017A1). To achieve the delayed release, the tablets may be enterically coated with a delayed release membrane/coating which will start to dissolve when the tablet is in a pH environment of approximately pH 4-8.

The current invention provides a pharmaceutical composition comprising clofazimine, or other compounds of the present invention, disintegrant, at least one protector coat layer used to separate and protect the clofazimine, or other compounds of the present invention, from the gastric environment and ensure delivery of clofazimine to the small intestine.

A pH dependent coating serves to release clofazimine, or other compounds of the present invention, in desired areas of the gastro-intestinal tract, e.g., the stomach or small intestine resulting in an absorption profile capable of providing at least about twelve hour and preferably up to twenty four hours of drug to a patient. When a pH independent coating is used the coating is designed to achieve optimal release regardless of pH changes in the environmental fluid (e.g., the GI tract). It is also possible to formulate compositions which release a portion of the dose in one desired area of the GI tract, e.g., the stomach, and release the remainder of the dose in another area of the GI tract, e.g., the small intestine.

Formulations according to the invention that utilize pH dependent coatings may also impart a repeat-action or pulsatile release effect whereby unprotected drug is coated over the enteric coat and is released in the stomach, while the remainder, being protected by the enteric coating, is released further down the gastrointestinal tract. Coatings which are pH dependent that may be used in accordance with the present invention include shellac, cellulose acetate phthalate (CAP), polyvinyl acetate phthalate, hydroxypropylmethylcellulose phthalate, and methacrylic acid ester copolymers, zein, and the like.

Other examples of sustained release formulations and coatings that may be used in accordance with the present invention are disclosed in U.S. Pat. Nos. 5,324,351, 5,356,467, and 5,472,712, hereby incorporated by reference in their entirety.

To protect clofazimine, or other compounds of the present invention, from the gastric environment it is preferred to use enteric coating polymers such as shellac, and/or any of its constituent aliphatic polyhydroxy acids presented as lactones, lactides and inter-esters or their derivatives. Another example of a preferred enteric coating polymer is the acetic and mono succinic acid ester of hydroxypropyl methylcellulose preferably hydroxypropyl methylcellulose acetate succinate, having a free succinic acid content not more than 10% by weight. In another embodiment, the free succinic acid content is not more than 1% by weight. In one embodiment, the weight-average molecular weight is 4.5 to $12 \times 10^4$ daltons measured by gel permeation chromatography. Other suitable members of the enteric cellulose esters are cellulose acetate phthalate, cellulose acetate trimellitate and hydroxypropyl methylcellulose phthalate. Enteric coating of the type methacrylic acid copolymers can also be used. Further examples of suitable enteric coating polymers are those based on methacrylic acid and methacrylic acid esters consisting of methacrylic acid polymer type A or type B or type C, or any combination thereof. These enteric coating polymers optionally contain one or more pharmaceutical excipients such as plasticizer(s), pigment(s) and colorants. Both protector and enteric coats can be applied from aqueous, organic or mixed solvent systems. The amount of enteric coating present is not less than 0.1% by weight. In another embodiment, the amount of enteric coating is 1 to 50% by weight. In another embodiment, the amount of enteric coating is 1 to 25% by weight. The enteric coat ensures delivery of over 80% the acid labile substance to the small intestine.

The process for the compounding of the compositions described herein forms another aspect of the embodiment of this invention. The acid sequestering compound is used to granulate the chosen pharmaceutical fillers using a fluidized bed technique, high shear granulator, blender or planetary mixer. The granulating liquid can be either aqueous, organic or mixed solvent systems and preferably containing the acid sequestering compound(s). The granules are dried in a fluid bed or tray dryer to a loss on drying (LOD) index of not more than 5%, after which they are blended with the acid labile compound(s), other excipients and disintegrant(s) in that order. The disintegrant can be incorporated intragranular and/or extragranular although the extragranular route is preferred.

The granules are formed into pellets or tablets using conventional pharmaceutical techniques. After forming they are first coated with the protector coat(s) and then with the enteric coat as previously described.

The finished product is presented as tablets or pellets or both in a hard gelatin capsule. It is preferable that the tablets or hard gelatin capsules are stored together with a desiccant in order to maintain low moisture content during long term storage. The final composition of the present invention provides that not more than 10% of the acid labile substance is released in acid media in about 2 hours and more than about 80% of the acid labile substance is released in 24 hours in alkaline media using USP dissolution apparatus I, II, III and IV.

In another embodiment, clofazimine, or other compounds of the present invention, can be formulated with polymers which can deliver the drug in a pH dependent manner (U.S. Pat. No. 5,955,509; US20040162263A1)

In order to enhance the solubility of clofazimine, or other compounds of the present invention, it is desirable to create particles with favorable surface area to volume ratios (U.S. Pat. Nos. 6,746,635; 6,824,791) as such particles will have faster dissolution kinetics. A typical process is provided for making dry, micronized particles of an agent, such as clofazimine, or other compounds of the present invention. The method includes milling clofazimine in a ball mill either with or without surfactant. The surfactant will allow further micronization of the clofazimine to particle sizes below 10 μm. Another approach involves (a) dissolving a macromolecular material, preferably a polymer, in an effective amount of a solvent, to form a solution; (b) dissolving or dispersing the agent in the solution to form a mixture; (c) freezing the mixture; and (d) drying by vacuum the mixture to form solid particles of the agent dispersed in solid macromolecular material. The micronization in this process occurs directly in a macromolecular matrix and hardening of the particles of agent by solvent removal takes place by lyophilization of the bulk matrix, which stabilizes the drug particles during hardening and prevents coalesence, thereby resulting in smaller final drug particles.

The process can be used in conjunction with a standard microencapsulation technique, typically following separation of the agent from the macromolecular matrix. In one embodiment, the process yields microparticles having a homogenous size distribution less than 2 μm in size. In certain embodiments, such microparticles have well defined, predictable properties.

In another embodiment, clofazimine or other compounds of the present invention, are formulated within a preparation that has a bioadhesive surface that enables the adherence of the preparation to specific human body organs or tissues such as the wall of the small intestine or the mucous membrane, wherein the bioadhesive agent is a polymer (Szucs et al. *European Journal of Pharmaceutical Sciences.* 2008; U.S. Pat. Nos. 5,744,155; 6,207,197; US20050249799A 1; US20060078618A1; WO05084639).

In another embodiment, clofazimine or other compounds of the present invention, are formulated in nanocrystalline form or nanoparticles to increase the surface area-to-volume ratio of the particles to improve drug dissolution (de Waard et al. *Journal of Controlled Release.* 2008. 128:179-183; Deng et al. *International Journal of Pharmaceutics.* 2008. 351:236-243; US20070134340A1).

In another embodiment, clofazimine or other compounds of the present invention are prepared in a liquid formulation (Cole et al. *Advanced Drug Delivery Reviews.* 2008. 60:747-756; Golenser et al. *Minireviews in Medicinal Chemistry.* 2006. 6:153-162; U.S. Pat. No. 7,205,413).

In another embodiment, clofazimine or other compounds of the present invention are formulated in alternative solid-state crystal forms with, for example, novel hydration states of clofazimine, novel solvation states of clofaziminie, crystallization with salts, or co-crystallization with other drugs or excipients (U.S. Pat. Nos. 6,919,370; 6,977,723; 7,061,605; 7,078,526; 7,108,970; 7,205,413).

In another embodiment, clofazimine or other compounds of the present invention are prepared in microreservoir systems that release clofazimine into physiological tissue at a controlled or extended rate (Santini et al. *Nature.* 1999. 397: 335-338; Sharma et al. *Expert Opinion on Drug Delivery.* 2006. 3:379-394; U.S. Pat. Nos. 5,385,709; 6,849,463; 6,976, 982; 7,070,590; 7,070,592; 7,226,442; US20070299385A1; US20080047926A1; US20080051766A1).

The quantities of the compounds of the present invention that are combined with the carrier materials to produce a composition in a single dosage form will vary depending upon the patient and the particular mode of administration. Preferably, provided compositions should be formulated so that a dosage of between 0.01-100 mg/kg body weight/day of the inhibitor (ie, clofazimine or other provided compound) can be administered to a patient receiving these compositions. Examples of compositions include compositions formulated to administer dosages of between 0.1-1 mg, 1-10 mg, 10-25 mg, 25-50 mg, 50-100 mg, 100-200 mg, 200-400 mg, or 400-800 mg per day of the inhibitor to the patient receiving these compositions. In other embodiments of the invention, compositions include compositions formulated to administer dosages of between 30-40 mg, 60-90 mg, 110-140 mg, 160-190 mg, 210-240 mg, or 260-290 mg per day of the inhibitor to the patient receiving these compositions. In still further embodiments of the invention, compositions include compositions formulated to administer dosages of between 33-37 mg, 65-85 mg, 120-130 mg, 170-180 mg, 220-230 mg, or 270-280 mg per day of the inhibitor to the patient receiving these compositions. In some embodiments, the composition is formulated into doses containing 1 mg, 5 mg, 10 mg, 20 mg, 25 mg, 50 mg, 75 mg, 100 mg, 200 mg, 300 mg, 400 mg, 600 mg, or 800 mg of the active composition. In yet other embodiments, the composition is formulated into doses containing 7.5 mg, 13 mg, 17.5 mg, 35 mg, 70 mg, 133 mg, 166 mg, 233 mg, 266 mg, or 333 mg of the active composition. Dosing regimens for these formulations may include but are not limited to single administration dosing, continuous infusions, once, twice, or three times daily dosing, weekly dosing, and monthly dosing.

In some treatment regimens, patients will be initially treated with larger doses of the compounds of the present invention ("loading dose") for a certain period of time ("loading period") in order to achieve a high tissue concentration of the drug, before being treated with lower doses of active composition ("maintenence dose") for a longer period of time ("maintenence period") in order to maintain the serum or tissue concentration of the active composition. For some chronic conditions, it is anticipated that the maintenance period may be for the life of the patient. In one example, a loading dose of 266 mg per day of inhibitor is used for a one month loading period, followed by administration of 133 mg per day inhibitor as the maintenance dose for as long as necessary to treat the condition. In another example, a 300 mg loading dose is used once per month, with 50 mg per day maintenance dose in the intervening days. In another example, a 600 mg daily loading dose is used for a one week loading period, with a 75 mg maintenance dose applied daily thereafter.

In some treatment regimens, administration of the inhibitor to a patient is temporarily halted (a "drug holiday"). In some examples, a patient may have cycles of daily doses of inhibitor for a month followed by a one month holiday. In another example, a patient might have daily dosing of an inhibitor for six months, followed by a one month holiday. In another example, a patient might have daily doses of an inhibitor for three weeks followed by a one week holiday. In yet another example, a patient might have daily doses of a drug for one week, followed by a three week holiday. In another example, a patient might have cycles of weekly doses of a drug for 6 weeks, followed by a three week holiday.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Administration

Compounds and compositions described herein are generally useful for inhibition of Kv1.3, $Ca^{2+}$ influx, T-cell signaling, T-cell proliferation, or IL-2 transcription or secretion. The Kv1.3 potassium channel plays an essential role in T-cells and has been implicated in a number of important autoimmune diseases including multiple sclerosis, psoriasis, rheumatoid arthritis, and type 1 diabetes, among others described herein.

Compounds and compositions, according to the method of the present invention, may be administered using any amount and any route of administration effective for treating or lessening the severity of a disorder associated with Kv1.3 activation. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, caplets, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, caplets, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting Kv1.3 activity in a biological sample comprising the step of contacting said biological sample with a compound of this invention, or a composition comprising said compound.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of Kv1.3 activity in a biological sample is useful for a variety of purposes that are known to one of skill in the art. Examples of such purposes include, but are not limited to, blood transfusion, organ-transplantation, biological specimen storage, and biological assays.

Another embodiment of the present invention relates to a method of inhibiting T-cell activation in a patient comprising the step of administering to said patient a compound of the present invention, or a composition comprising said compound. In certain emobidiments, the T-cells are effector memory T-cells. In certain embodiments, the present invention provides a method of inhibiting T-cell activation in a patient comprising the step of administering to said patient a compound of the present invention and in another embodiments, those T-cells are effector memory T-cells. In another embodiment, the present invention provides a method of inhibiting effector memory cells in a patient by administration to a patient a compound of the present invention, characterized in that such inhibition does not affect central naïve T-cells.

In other embodiments, the present invention provides a method for treating a disorder wherein pathological T-cell activation may be involved ("T-cell Disorders") in a patient in need thereof, comprising the step of administering to said patient a compound according to the present invention or pharmaceutically acceptable composition thereof. In certain embodiments, the present invention provides a method for treating a disorder where T-cell activity is involved. As used herein, the term "T-cell activity" includes, but is not limited to one or more of proliferation, migration, differentiation, co-stimulation, or secretion of molecules, wherein such molecules include cytokines, chemokines, cytotoxics and other signaling compounds. Such disorders are described in detail herein and include autoimmune disorders. Exemplary disorders include Acute disseminated encephalomyelitis (ADEM), Addison's disease, Allopecia areata, Alzheimers disease, Ankylosing spondylitis, Antiphospholipid antibody syndrome, Autoimmune hemolytic anemia, Autoimmune hepatitis, Autoimmune inner ear disease, Autoimmune Lymphoproliferative Syndrome (ALPS), Autoimmune polyendocrine/polyglandular syndrome, Autoimmune thrombocytoipenia purpura, Balo disease, Behçet disease, Bullous pemphigoid, Cardiomyopathy, Celiac sprue-dermatitis herpetiformis, Chronic fatigue immune dysfunction syndrome (CFIDS), Chronic inflammatory demyelinating neuropathy, Cicatrical pemphigoid, Coeliac disease, Cold agglutinin disease, CREST syndrome, Crohn's disease, Cystic fibrosis, Degos disease, Dermatomyositis, Diabetes (Type I or Juvenile onset), Early onset dementia, Eczema, Endotoxin shock, Essential mixed cryoglobulinemia, Familial Mediterranean fever, Fibromyalgia, Fibromyositis, Graft vs. Host disease, Goodpasture's syndrome, Graves' disease, Guillain-Barré syndrome (GBS), Hashimoto's thyroidosis, Hidradenitis suppurativa, Idiopathic pulmonary fibrosis, Idiopathic thrombocytopenic purpura, IgA nephropathy, Lambert-Eaton Myasthenic Syndrome, Leukemia, Lichen planus, Ménière disease, Mixed connective tissue disease, Multiple sclerosis, Multiphasic disseminated encephalomyelitis, Myasthenia gravis, Neuromyelitis Optica, Paraneoplastic Syndromes, Pemphigus, Pemphigus vulgaris, Pernicious anaemia, Polyarteritis nodosum, Polychondritis, Polymyalgia rhematica, Polymyositis, Primary agammaglobulinemia, Primary biliary cirrhosis, Plaque Psoriasis, Psoriatic arthritis, Pustular psoriasis, Raynaud phenomenon, Reiter syndrome, Restenosis following angioplasty, Rheumatic fever, Rheumatoid arthritis, Rheumatoid psoriasis, Sarcoidosis, Scleroderma, Sepsis, Sezary's disease, Sjögren's syndrome, Stiff-person syndrome, Lupus including Systemic Lupus Erythematosis (SLE), Takayasu arteritis, Temporal arteritis (also known as "giant cell arteritis"), Transplant or Allograft rejection, Ulcerative colitis, Uveitis, Vasculitis, Vitiligo, and Wegener's granulomatosis.

In other embodiments, the present invention provides a method for treating a disorder mediated by T-cell activation in a patient in need thereof, comprising the step of administering to said patient a compound according to the present invention or pharmaceutically acceptable composition thereof. Such disorders are described in detail herein and include autoimmune disorders. Exemplary disorders associated with T-cell activation include Acute disseminated encephalomyelitis (ADEM), Addison's disease, Allopecia areata, Ankylosing spondylitis, Autoimmune hepatitis, Bullous pemphigoid, Chronic inflammatory demyelinating neuropathy, Crohn's disease, Coeliac disease, Diabetes (Type I or Juvenile onset), Eczema, Hashimoto's thyroidosis, Lupus, Multiphasic disseminated encephalomyelitis, Multiple sclerosis, Myasthenia gravis, Pemphigus, Pemphigus vulgaris, Polymyositis, Primary biliary cirrhosis, Plaque Psoriasis, Psoriatic arthritis, Rheumatoid arthritis, Rheumatoid psoriasis, Scleroderma, Sjögren's syndrome, Transplant or Allograft rejection, Uveitis.

In other embodiments, the present invention provides a method for treating a disorder mediated by effector memory T-cell activation in a patient in need thereof, comprising the step of administering to said patient a compound according to the present invention or pharmaceutically acceptable composition thereof. Such disorders are described in detail herein and include autoimmune disorders. Exemplary disorders associated with effector memory T-cell activation include multiple sclerosis, plaque psoriasis, rheumatoid psoriasis, psoriatic arthritis, Chrohn's disease, irritable bowel disorder, lupus, rheumatoid arthritis, graft rejection, graft versus host disease, and type 1 diabetes.

In other embodiments, the present invention relates to a method of inhibiting the influx of calcium into T-cells. In another embodiment, the T-cells are effector memory cells. Another embodiment of the present invention relates to a method of inhibiting the influx of calcium into T-cells in a patient comprising the step of administering to said patient a compound of the present invention, or a composition comprising said compound. In another embodiment of the invention relates to a method of inhibiting the influx of calcium into T-cells wherein the T-cells are effector memory cells in a patient comprising the step of administering to said patient a compound of the present invention, or a composition comprising said compound. In another embodiment, the present invention relates to a method of inhibiting the influx of calcium into T-cells to treat T-cell Disorders by administering to a patient a compound of the present invention, or a composition comprising said compound.

In other embodiments, the present invention relates to a method of inhibiting one or more of the dephosphorylation, transcription or translocation of the Nuclear Factor of Activated T-cells (NFAT) in T-cells. In another embodiment, the T-cells are effector memory cells. In another emobidment, the present invention relates to a method of inhibiting inhibiting one or more of the dephosphorylation, transcription or translocation of NFAT in a patient comprising the step of administering to said patient a compound of the present invention, or a composition comprising said compound. In another embodiment, the present invention relates to a method of inhibiting one or more of the dephosphorylation, transcription or translocation of NFAT in a patient wherein the T-cells are effector memory cells comprising the step of administering to said patient a compound of the present invention, or a composition comprising said compound. In another embodiment, the present invention relates to a method of inhibiting one or more of the dephosphorylation, transcription or translocation of NFAT to treat T-cell Disorders by administering to a patient a compound of the present invention, or a composition comprising said compound.

In other embodiments, the present invention relates to a method of inhibiting the proliferation of activated T-cells. In another embodiment, the activated T-cells are effector memory cells. Another embodiment of the present invention relates to a method of inhibiting the proliferation of activated T-cells in a patient comprising the step of administering to said patient a compound of the present invention, or a composition comprising said compound. In another embodiment of the invention relates to a method of inhibiting the proliferation of activated T-cells wherein the T-cells are effector memory cells in a patient comprising the step of administering to said patient a compound of the present invention, or a composition comprising said compound. In another embodiment, the present invention relates to a method of inhibiting the proliferation of activated T-cells to treat T-cell Disorders by administering to a patient a compound of the present invention, or a composition comprising said compound.

In other embodiments, the present invention relates to a method of inhibiting the transcription or secretion of interleukin-2 (IL-2) from T-cells. In another embodiment, the T-cells are effector memory cells. Another embodiment of the present invention relates to a method of inhibiting transcription or secretion of IL-2 from T-cells in a patient comprising the step of administering to said patient a compound of the present invention, or a composition comprising said compound. Another embodiment of the invention relates to a method of inhibiting the transcription or secretion of IL-2 from T-cells wherein the T-cells are effector memory cells in a patient comprising the step of administering to said patient a compound of the present invention, or a composition comprising said compound. In another embodiment, the present invention relates to a method of inhibiting transcription or secretion of IL-2 to treat T-cell Disorders by administering to a patient a compound of the present invention, or a composition comprising said compound.

In another embodiment, the present invention relates to a method of causing the translocation of GLUT4 to the plasma membrane of cells. In another embodiment, the cells are adipocytes and in another embodiment the cells are muscle cells.

Another embodiment of the invention realtes to a method of treating type 2 diabeties or obesity by administering to said patient a compound of the present invention, or a composition comprising said compound. Another embodiment of the present invention relates to a method of causing GLUT4 translocation to the plasma membrane of cells. In another embodiment, the cells are adipocytes and in another embodiment the cells are muscle cells. Another emobodiment of the invention realates to a method of treating type 2 diabeties or obesity by administering to said patient a compound of the present invention which causes GLUT4 translocation to the plasma member of cells. In another embodiment, the cells are adipocytes and in another embodiment the cells are muscle cells. Another emobodiment of the invention realates to a method of treating type 2 diabeties or obesity by administering to said patient a compound of the present invention which increases insulin sensitivity.

Depending upon the particular condition, or disease, to be treated, additional therapeutic agents, which are normally administered to treat that condition, may also be present in the compositions of this invention. As used herein, additional therapeutic agents that are normally administered to treat a particular disease, or condition, are known as "appropriate for the disease, or condition, being treated." Such therapeutic agents include, but are not limited to analgesics, anti-inflammatory agents, anti-helminthics, anti-arrhythmic agents, anti-bacterial agents, anti-viral agents, anti-hypertensive agents, anti-coagulants, anti-depressants, anti-diabetics, anti-epileptics, anti-fungal agents, anti-gout agents, anti-malarials, anti-migraine agents, anti-muscarinic agents, anti-neoplastic agents, erectile dysfunction improvement agents, immunosupressants, anti-protozoal agents, anti-thyroid agents, anxiolytic agents, sedatives, hypnotics, neuroleptics, beta-blockers, cardiac inotropic agents, corticosteroids, diuretics, anti-parkinsonian agents, gastro-intestinal agents, histamine $H_1$ and $H_2$ receptor antagonists, keratolytics, lipid regulating agents, anti-anginal agents, nutritional agents, opioid analgesics, sex hormones, stimulants, muscle relaxants, anti-osteoporosis agents, anti-obesity agents, cognition enhancers, anti-urinary incontinence agents, nutritional oils, anti-benign prostate hypertrophy agents, essential fatty acids, non essential fatty acids, vitamins, minerals, appetite suppressants and mixtures thereof.

For example, compounds of the present invention, or a pharmaceutically acceptable composition thereof, are administered in combination with anti-inflammatory or other agents used to treat autoimmune diseases such as 2-Methoxyestradiol—EntreMed, 802-2, Abatacept, ABT 874, Aceclofenac, Acitretin, Actarit, Adalimumab, Adapalene, AEB 071, AEG 35156, AG 18, AGN 194310, AIN 457, Alefacept, Alemtuzumab, Alemtuzumab, Alicaforsen, Alitretinoin oral—Ligand Pharmaceuticals, Alprostadil lyophilized liposomal, AME 527, AMG 108, AMG 714—Autoimmune disease, AMG 827, Amifampridine, Aminolevulinic acid—DUSA, Ammonium lactate—Foamix, Amotosalen, AN 0128, AN 2728, Anakinra and other interleukin-1 blockers, Anapsos, Anthralin, Anti-CD4 monoclonal antibody 16H5, Anti-CD44 monoclonal antibody IM7, Anti-CD6 monoclonal antibody h-T1, Anti-Fas monoclonal antibody—Centocor/Santen, antifolates—Chelsea Therapeutics, Anti-ICAM-1 monoclonal antibody 1A-29, Anti-interferon-gamma polyclonal antibody—Advanced Biotherapy, Anti-interleukin-8 monoclonal antibody, anti-LINGO-1 antibody—Biogen Idec, Anti-L-selectin monoclonal antibodies—PDL BioPharma, anti-MIF antibody—Baxter Healthcare/Dyax, Antithymocyte globulin, anti-TNF-alpha therapeutics—Pharmexa, Anti-tumour necrosis factor alpha antibody oral, Anti-tumour necrosis factor monoclonal antibody—3SBio/Epitomics, Apilimod, apolipoprotein E-mimetic peptide therapeutics—Cognosci Inc., Apratastat, Apremilast, Apremilast, ARRY 162, ART 621, ASF 1075, Atacicept, Atizoram, ATL 1101, ATL 1102, ATX MS1467, Autologous T-cell vaccine—Opexa Therapeutics, AV 1142742, AVR 118, AVT 02, Azathioprene, Azathioprine, AZD 5672, AZD 5904, AZD 9056, Baminercept, BCI-202, BCX 4208, Beclometasone oral—DOR BioPharma, Becocalcidiol, Belimumab, Betamethasone butyrate propionate, Betamethasone valerate foam—Foamix, Betamethasone valerate foam—Stiefel Laboratories, Bexarotene oral, Bexarotene topical, BG 00012 (Panaclar), BG 12, BGC 200134, BHT 3009, Bimosiamose, Binetrakin, BIO 023, BIO 5192, BMS 582949, Briobacept, BT 061, Bucillamine—Santen Pharmaceutical, BX 471, C 1311, C 201, C 6448, C 9709, C1 inhibitors—Johnson & Johnson Pharmaceutical Research and Development, Calcipotriol or other vitamin D3 analogues, Calcipotriol/betamethasone dipropionate, Calcithiazol, Calcitriol—Galderma, CAM 3001, Canakinumab, Cannabidiol—GW Pharmaceuticals, cannabinoid CB2 receptor agonists—BTG, cannabinoid-2 receptor agonists—Pharmos, Cannabinoids, Carbenoxolone topical—York Pharma, Carbohydrate-based anti-inflammatories—Praxis/Fairchild, CBP 2011, CCR1 receptor antagonists—Pharmacopeia, CCR2 receptor antagonists—EPIX, CCR8 antagonists—Millennium Pharmaceuticals, CCX 140, CCX 354, CD8 antagonists—MediGene, CDP 323, CDP323, Celecoxib, cell adhesion antagonists—ICOS, cell-cell fusion inhibiting peptides—Aplagen, Certolizumab pegol, CF 101, CH 1504, chemokine inhibitor therapy—Merck Serono, Ciclosporin—Novartis, Cladribine, Cladribine, Clobetasol propionate foam—Stiefel Laboratories, Clobetasol propionate topical—Galderma, Clodronic acid, Clofarabine, CNTO 136, Combretastatin A4 phosphate, Controlled-release prednisone—Nitec/SkyePharma, CP 195543, CP 481715, CP 690550, CPH 82, CRA 028129, CRB 15, CRx 102, CT 112-Curative Health Services, CT 327, CT 737, CT 747, CT 757, CT 767, CTA 018, CXCR3 antagonists—Millennium/Sanofi-Aventis, Cyclopamine, Cyclophosphamide, Cyclosporin A, CYT 007 TNFQb, DA 7911, Daclizumab, DE 096, Delmitide, Denileukin diftitox, Denosumab, deuterated therapeutics—CoNCERT Pharmaceuticals, Dexamethasone liposomal, Dexanabinol, Didox, Diethylnorspermine, dihydroorotate dehydrogenase inhibitors—Laboratorios Almirall, Dithranol, Doramapimod, Doramapimod, D-penicillamine, Eculizumab, Efalizumab, Efipladib, Efomycines—Bayer, ELND 001, ELND 002, Epinastine, Epratuzumab, Esomeprazole/naproxen, Estradiol and estrogen receptors, Estriol, ET 002, Etalocib, Etanercept, Etoricoxib, F 991, Falecalcitriol, Fampridine, Fingolimod (FTY720), Firategrast, FK 779, Fluasterone, Fumaric acid esters, Galiximab, GBL 100, GBR 500, GEM SP—GEMACBIO, gene-activated interferon beta—Shire Pharmaceuticals, genetically modified interferon-beta molecules—GBF, Genz 29155, Giripladib, Glatiramer acetate, GMDP, Goat serum-derived polyclonal antibodies, Gold salts, Golimumab, GPX 150, GRC 4039, GSK 1827771, GSK 315234, GSK 681323, GSK 856553, Gusperimus, GW 274150, HE 3286, HENO 3, heparanase inhibitors—Progen/Griffith, HF 0220, histone deacetylase inhibitors—TopoTarget, HSP 10, HSV thymidine kinase gene therapy, Human mesenchymal stem cell therapy—Osiris, Hydroxychloroquine, Hydroxyurea, Ibudilast, Ibuprofen, ICN 16064, IdeS—Hansa Medical, Igurati-mod, 1-kappa B kinase inhibitors—Millennium Pharmaceuticals/sanofi-aventis, Ilodecakin, ILV 094, Immune globulin—Talecris Biotherapeutics, ImmunoKine, INCB 18424, INCB 3284, INCB 8696, Inecalcitol, Infliximab, Inolimomab, Inosine, interferon beta gene therapy—Bayer HealthCare Pharmaceuticals, Interferon beta variant—Nautilus, Interferon beta-intranasal—Nastech Pharmaceutical Company, Interferon-alpha—Amarillo/Hayashibara, Interferon-alpha-2a, Interferon-alpha-n3, Interferons including interferon beta-1a and interferon beta-1b, Interferon-tau, interleukin 23 antagonists—Archemix/Elan, Interleukin 6 inhibitor—Y's Therapeutics, Interleukin-1 beta antibody—Eli Lilly, Interleukin-1 receptor type II—Amgen, interleukin-31—ZymoGenetics/Merck Serono, Intravenous immunoglobulin, ion channel modulators—Lectus Therapeutics, IPL 423323, IR 208, J 113863, JAK3 inhibitors, JB 991, JNK inhibitor—Merck Serono, K 252a derivatives—Bio3 Research/Creabilis Therapeutics, K 832, Kahalalide F, KB 002, KC 706, Kv1.3 inhibitors—4SC, Kv1.3 potassium channel inhibitors—Bionomics/Merck Serono, L 869298, Lactobacilli based inflammatory therapy—Symbigene, Lanreotide, Laquinimod, Leflunomide, LEO 80190, Lestaurtinib, Lexipafant, LFA-1 antagonists—ICOS, LIF 313, LL 4218, LLL 3348, LMP 160, LMP 420, long-acting interferon beta—Bolder Biotechnology, long-lasting interferon beta—Genexine, LR 103, Lumiracoxib, LX 2931, LY 2127399, Lymphocyte function-associated antigen-1 antagonist—Bristol-Myers Squibb, Mahonia aquifolium extract, Maraviroc, Maxacalcitol, MAXY 10, MBP 8298, MDI 101, MDI 301, MDX 018, MDX 1100, MDX 1342, MEDI 545, Meloxicam, Merimepodib, metalloenzyme inhibitors—Merck SeronoNernalis, Methotrexate, MIF inhibitors—Cytokine PharmaSciences, Minactivin, Minocycline, Mitoxantrone or other anti-neoplastic agents, MIV 701, Mizoribine, MK 0812, MLN 1202, MLN 3701, MLN 3897, MM 093, MNX 160, Mometasone/nortriptyline, Mometasone/salicylic acid, MOR 103, Moxilubant maleate, MP 4, MP 435, Multiple sclerosis vaccine—Opexa Therapeutics, Muscular dystrophy gene therapy—Transgene, MV 9411, Mycophenolate mofetil, Naltrexone, nanobodies—Ablynx, Naproxen, Natalizumab, Natalizumab or other anti-alpha-4-integrin inhibitors, NBI 107, NBI 108, NCX 1022, Nerispirdine, Neurovax, NF-kappa-B decoy oligonucleotide—AnGes MG, NPC 16570, NPI 1302a-3, NTx 488 regimen—Stem Cell Therapeutics, Ocrelizumab, Odulimomab, Ofatumumab, OM 8980, oncostatin M therapeutics—Genodyssee, Onercept, ONO 4641, Opebacan, Oprelvekin, Oral human gammaglobulin, Ostabolin topical—Zelos Therapeutics, Otelixizumab, P 16—Transition Therapeutics, p38 kinase inhibitor—Bristol-Myers Squibb, p38 MAP kinase inhibitor—Amgen, p38 MAP kinase inhibitors—Kemia, PA 1093, Paclitaxel—Angiotech, Paquinimod, PARP inhibitors—Inotek, Pazopanib, PD 170262, PD 360324, Peginterferon alfa-2b, PEG-interferon beta-1a—Biogen Idec, PEG-interferon beta-1a—Merck Serono, PEG-interleukin-29—ZymoGenetics, Pentostatin, Perampanel, PF 755616, PH 797804, phosphodiesterase IV inhibitors—BTG, photosensitisers—Molteni Therapeutics, PI 2301, PIC 060, Pimecrolimus, Pimecrolimus topical, Pioglitazone, Pirfenidone, Piroxicam beta-cyclodextrin, Pixantrone, Pixantrone (BBR 2778), PMI 001, PMX 53, potassium channel blockers—Scion, Pralnacasan, Prednisolone farnesil, Priliximab, Prolactin, protein therapeutics—Scil Proteins GmbH, PRTX 100, Psoriasis vaccine—Astralis/Pacira, PUVA, PXD 118490, R 115866, R 1295, R 788, R 85355, Rabeximod, recombinant immunoglobulin P technology—MultiCell Technologies, REGN 88, remyelinating monoclonal antibodies—Acorda Therapeutics/Mayo Clinic, Resveratrol—Sirtris Pharmaceuticals, Retinoids, Riluzole, Rimacalib, Rituximab, Roflumilast, Rose bengal sodium, Rosiglitazone, Rostaporfin, RPI 78M, RTL 1000, RWJ 445380, RWJ 68354, S 7-Transition Therapeutics, SA 9499, Salicylic acid, Samarium 153 SM lexidronam, Sargramostim, SBI 087, SBP 002, SC 12267, SC 53228, SCIO 323, SCIO 469, selectin antagonists—Revotar, SF 1019, Simvastatin, Sirolimus, small glycanic drugs—Endotis, small molecule Cathepsin S inhibitors—Medivir, SSR 150106, Statins, stem cell therapeutics—Histostem, stem cell therapies—BrainStorm Cell Therapeutics, stem cell-based therapeutics—Pluristem Therapeutics, Steroids such as methylprednisolone, Sulfasalazine, suppressor of cytokine signalling molecules—Zenylh Therapeutics, SYI 2074, Synthetic triterpenoids—Reata Pharmaceuticals, T 487, T 5224, TA 5493, Tacalcitol, Tacrolimus, Tadekinig alfa, TAK 783, Talactoferrin alfa, Talampanel, Tamibarotene, Tazarotene, Tazarotene topical, TBC 4746, Temsirolimus, Teplizumab, Terameprocol, Teriflunomide, Teriparatide topical—Manhattan Pharmaceuticals, tetracycline derivatives—Paratek Pharmaceuticals, TH 9402, Thalidomide, therapeutics—Altor BioScience, Tigderimus, Tioguanine, Tisocalcitate, TJ 114, TJ 41, TK 54, TK gene therapy—MolMed, TNF receptor antagonists—Fulcrum Pharmaceuticals, Tocilizumab, toll-like receptor antagonists—Idera, topical anti-TNF-alpha therapeutics—York Pharma, Topical ciclosporin, topical methotrexate—NanoCyte, topical NSAID—Milestone Pharmaceuticals, Tovaxin, TP 10, Tranilast, tricyclic bis-enones: Reata Pharmaceuticals, Trimerised apolipoprotein A1, Trimetrexate, TrkA receptor inhibitors—VM Discovery, TRU 015, TV 3606, TV 5010, type-I interferons—Alios BioPharma, UR 1505, Urocanic acid—BioC is Pharma, Ustekinumab, Valategrast, Valdecoxib, vascular adhesion protein 1 inhibitors—La Jolla Pharmaceutical, VEL 0230, Verteporfin, VGX 1027, Visilizumab, VIT 100, Vitamin D, vitamin D receptor modulators—Eli Lilly, vitamin D signal amplifiers—Cytochroma, VLA-4 antagonists, Voclosporin, VT 111, VTP 201227, VX 702, VX 765, WAY 195725, WBI 1001, XA 547, Xaliproden, XOMA 052, Z 92, Zanolimumab, ZCL 8, ZD 158252, ZK 158252, ZRx 101, and combination therapies thereof.

In other embodiments, the analgesic agents which are administered in combination with the compounds of the present invention, or a pharmaceutically acceptable composition thereof include, but are not limited to chlorobutanol, clove, eugenol, alfentanil, allylprodine, alphaprodine, anileridine, benzylmorphine, bezitramide, buprenorphine, butorphanol, clonitazene, codeine, codeine methyl bromide, codeine phosphate, codeine sulfate, desomorphine, dextromoramide, dezocine, diampromide, dihydrocodeine, dihydrocodeinone enol acetate, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, hydrocodone, hydromorphone, hydroxypethidine, isomethadone, ketobemidone, levorphanol, lofentanil, meperidine, meptazinol, metazocine, methadone hydrochloride, metopon, morphine, morphine hydrochloride, morphine sulfate, myrophine, nalbuphine, narceine, nicomorphine, norlevorphanol, normethadone, normorphine, norpipanone, opium, oxycodone, oxymorphone, papavereturn, pentazocine, phenadoxone, phenazocine, phenoperidine, piminodine, piritramide, proheptazine, promedol, propiram, propoxyphene, remifentanil, sufentanil, tilidine, aceclofenac, acetaminophen, acetaminosalol, acetanilide, acetylsalicylsalicylic acid, alclofenac, alminoprofen, aloxiprin, aluminum bis(acetylsalicylate), aminochlorthenoxazin, 2-amino-4-picoline, aminopropylon, aminopyrine, ammonium salicylate, amtolmetin guacil, antipyrine, antipyrine salicylate, antrafenine, apazone, aspirin, benorylate, benoxaprofen, benzpiperylon, benzydamine, bermoprofen, bromfenac, p-bromoacetanilide, 5-bromosalicylic acid acetate, bucetin, bufexamac, bumadizon, butacetin, calcium acetylsalicylate, carbamazepine, carbiphene, carsalam, chlorthenoxazin(e), choline salicylate, cinchophen, ciramadol, clometacin, clonixin, cropropamide, crotethanude, dexoxadrol, dilcnanuzole, ditlunisal, dihydroxyaluminum acetylsalicylate, dipyrocetyl, dipyrorre, fanurfazone, entcnanuc acid, epirizole, etersalatc, elhcnzamide, ethoxazcne, etodolac, felbinac, fenoprofen, floctafenine, flufenamic acid, fluoresone, flupirtine, fluproyuazone, flurbiprofen, fosfosal, gentisic acid, glafenine, ibufenac, imidazole salicylate, indomethacin, indoprofen, isofezolac, isoladol, isonixin, ketoprofen, ketorolac, p-lactophenetide, lefetamine, lornoxicam, loxoprofen, lysine acetylsalicylate, magnesium cetylsalicylate, methotrimeprazine, metofoline, mofezolac, morazone, morpholine salicylate, naproxen, nefopam, nifenazone, 5'-nitro-2'-propoxyacetanilide, parsalmide, perisoxal, phenacetin, phenazopyridine hydrochloride, phenocoll, phenopyrazone, phenyl acetylsalicylate, phenyl salicylate, phenyramidol, pipebuzone, piperylone, propacetamol, propyphenazone, ramifenazone, rimazolium metilsulfate, salacetamide, salicin, salicylamide, salicylamide O-acetic acid, salicylsulfuric acid, salsalate, salverine, simetride, sodium salicylate, suprofen, talniflumate, tenoxicam, terofenamate, tetrandrine, tinoridine, tolfenamic acid, tramadol, tropesin, viminol, xenbucin, zomepirac, pregabalin, gabapentin, carbamazepine, NGX-4010, NP-1, amitriptyline, nortriptyline, ruboxistaurin, duloxetine, memantine, lamotrigine, REN-1654, Neurodex, Prosaptide, harkoseride, Liprostin, pirfenidone, AS-3201, TAK-428, QR-333, capsaicin, amitriptyline, amoxapine, chlomipramine, desipramine, doxepin, imipramine, nortriptyline, protriptyline, trimipramine, and combinations thereof.

In other embodiments, compounds of the present invention, or a pharmaceutically acceptable composition thereof, are administered in combination with other agents to increase efficacy such as ethaverine, lomerizine, bifonazole, ticonazole, and harmine.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of formula I, an additional therapeutic agent, and a pharmaceutically acceptable carrier, adjuvant, or vehicle.

The amount of both, an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of a provided compound can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-100 µg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

EXEMPLIFICATION

Compounds of the present invention are prepared according to methods known to one of ordinary skill in the art. Such methods include those described in, e.g., U.S. Pat. Nos. 2,946,792, 2,943,089, 2,948,726, 3,592,814, 5,763,443, and 3,499,899, the entirety of each of which is hereby incorporated herein by reference. Provided compounds are also prepared by methods substantially similar to those described by O'Sullivan, et al. 1988 *J. Med. Chem.* 31: 567-572 and O'Sullivan. 1984 *J. Chem. Res. S:* 52-53, the entirety of each of which is hereby incorporated herein by reference.

A library of compounds was assembled of mostly FDA-approved drugs as well as drugs approved abroad and drug candidates that have reached Phase II clinical trials. The vast majority of drugs in the library, including clofazimine, were included even though it would be unexpected for them to have the ability to inhibit T-cell activity. Clofazimine was identified as a promising hit from another cell-based screen for novel inhibitors of the intracellular TCR signaling pathway leading to the transcriptional activation of IL-2. Through a systematic examination of different steps in intracellular TCR signaling, it was unexpectedly discovered that clofazimine blocked calcium signaling in T-cells by directly interfering with the function of the Kv1.3 channel. Importantly, it was demonstrated that clofazimine was effective in preventing human T-cell-mediated skin graft rejection in a reconstituted mouse model of skin transplantation. The distinct structure of clofazimine also offers a novel scaffold for the development of future generations of immunosuppressive and immunomodulatory agents.

Example 1

Assay Methods and Results

Cell Culture and IL2-Luciferase Reporter Cell Line

Jurkat E6.1 (ATCC TIB152) T-cells were maintained in RPMI medium 1640 (Invitrogen) supplemented with 10% FBS, 2 mM-L-glutamine, penicillin (50 µg/ml) and streptomycin (50 µg/ml). HFF-1 (ATCC SCRC 1041) fibroblasts were maintained in low glucose DMEM (Invitrogen) supplemented with 10% FBS, 2 mM-L-glutamine, penicillin (50 µg/ml) and streptomycin (50 µg/ml). Jurkat E6.1 cells were transfected with linearized pIL2-Luc-Neo and linearized pMEP4 by electroporation, followed by selection for resistance to 400 µg/ml hygromycin. The stably transfected IL-2 reporter cell line, Jurkat/IL-2Luc, was maintained in hygromycin, which was omitted from medium for the screening and other assays.

Screening Assay

Jurkat/IL-2Luc cells were seeded in 96 well plates (Nunc 136102) at $2 \times 10^5$ (180 µL) per well. Cells were incubated with 10 µM (final concentration) drugs from the library for 1 h before they were stimulated with 1 µM ionomycin and 40 nM phorbol myristate acetate (PMA) for an additional 16 h.

Cells were pelleted by centrifugation. Upon removal of the culture medium, lysis/assay buffer was added into each well. The luciferase activity was determined as per the manufacturer's instructions.

Calcein Incorporation Assay

HFF-1 (human forebrain fibroblast) cells ($2\times10^3$ in 190 µl) were seeded into 96-well plates and were incubated with drugs from the library for 4 days. Cells were washed with PBS twice before they were treated with 1 µM (final concentration) Calcein-AM (invitrogen C1430) for 4 h. Plates were directly counted by a fluorescent plate reader.

Detection of Il-2 Secreted from T-Cells

Jurkat E6.1 T-cells ($1\times10^5$ in 180 µl) were seeded into 96-well plates. Cells in each well were treated with different concentrations of clofazimine for 1 h before 1 µM ionomycin and 40 nM PMA were added. The incubation was continued for 2 days. The plates were centrifuged at 1,200×g for 5 min, and the supernatant from each well was collected followed by ELISA detection of IL-2. The primary antibody, biotinylated secondary antibody and HRP conjugated avidin were purchase from BD/Pharmingen.

Dephosphorylation of Endogenous NFATc2

Jurkat T-cells were pretreated with indicated compounds for 1 h before 3 µM (final concentration) ionomycin was added. Cells were harvested after 30 min and lysed in a lysis buffer [40 mM Tris (pH 7.8), 1% NP-40, 10 mM EDTA, 60 mM $Na_3P_4O_7$ and common protease inhibitors] by sonication. NFATc2 was resolved by 8% SDS-PAGE followed by Western blot analysis using anti-NFAT antibodies (Santacruz Sc-7296, 1:100 dilution).

Calcium Imaging Assay

JurkaT-cells were attached to L-lysine-coated glass dishes (MatTek). Cells were loaded with fura-2-AM (Invitrogen_F-1201) for 45 min before they were washed sequentially with growth medium and $Ca^{2+}$-free HBSS. Fluorescence excitation wavelengths were set at 350 and 380 nm, respectively, on a Zeiss Axiovert 200M microscope while emission wavelength was set at 510 nm. Changes in intracellular calcium concentrations were determined by fluorescence intensity ratio ($F_{350}/F_{380}$).

Patch-Clamp Experiments

Patch pipettes, pulled from glass capillaries (inner diameter 1.5 mm, Kimble products) with a horizontal puller (Sutter instruments, Modell P-97), were fire-polished, and had resistances between 2 and 4 MOhm. Patch-clamp experiments were performed in the tight-seal whole-cell configuration at room temperature (22-24° C.). High-resolution current recordings were acquired by a computer-based patch-clamp amplifier system (EPC-9, HEKA). Immediately following establishment of the whole-cell configuration, every two seconds voltage ramps of 50 ms duration spanning the voltage range of −100 to +100 mV for Jurkat T-cells and −150 to +150 mV for HEK293 were delivered from a holding potential ($V_h$) of −70 mV for Jurkats and 0 mV for HEK293 cells over a period of 300-600 s. Heterologously expressed potassium currents (Kv 1.1, Kv 1.2, Kv 1.3, Kv 1.5 and Kv3.1) were acquired using a voltage ramp from −100 mV to +100 mV over 500 ms and at 2 s (Kv3.1 & Kv1.2) or 5 s intervals from a $V_h$ of −80 mV. All voltages were corrected for a liquid junction potential of 10 mV. Currents were filtered at 2.9 kHz and digitized at 100 ms intervals. Capacitive currents and series resistance were determined and corrected before each voltage ramp using the automatic capacitance compensation of the EPC-9. Kv 1.3 currents were normalized to the point of application of 5 µM clofazimine. Kv1.3 currents in Jurkat T-cells were measured at +80 mV. Heterologously expressed Kv1.1, Kv1.2, Kv1.3, Kv1.5 and Kv3.1 were assessed at +80 mV except in Figure S7, where currents were additionally measured at the more physiological voltage of 0 mV. CRAC currents in HEK293 cells were assessed at −80 mV. Standard external solution contained (in mM): 140 NaCl, 1 $CaCl_2$, 2 $MgCl_2$, 2.8 KCl, 10 HEPES-NaOH, with pH at 7.2 and osmolarity 300-320 mosm. The solution contained 10 mM $CaCl_2$ in the case of CRAC measurements. Internal standard solution contained (in mM): 120 K-glutamate, 1 $MgCl_2$, 8 NaCl, 10 HEPES-KOH, 10 K-BAPTA, with pH 7.2 and osmolarity 290-310 mosm. The internal solution was supplemented with 20 µM $IP_3$ for CRAC measurements. Substance application was performed on individual cells using a wide-mouth glass pipette connected to a pneumatic pressure device.

Immunofluorescence

Jurkat T-cells treated with clofazimine were centrifuged onto L-lysine-coated coverslips. Cells were fixed with 4% p-formaldehyde for 15 min. The cells were washed in PBS, permeabilized by −20° C. methanol and blocked with 10% donkey serum in PBS. The fixed cells were then incubated with Kv1.3 primary antibody (sc-17239 at 1:100 dilution) for 1 h. Cells were washed in PBS (3×5 min) and incubated with donkey anti-goat Cy5 antibodies for an additional 1 h. Cells were then washed three times in PBS, mounted, and photographed. Mounting was performed using Vectashield mounting medium (Vector Laboratories) and images were captured using either a Zeiss LSM510 confocal microscope. Merged images were compiled using LSM5 Image Examiner or Adobe Photoshop CS.

Results

The signaling pathway emanating from TCR and leading to the transcriptional activation of the IL-2 promoter is dependent on the second messenger calcium and calcineurin that has been shown to be a proven target for both cyclosporine A and FK506. We thus engineered a reporter cell line by stably integrating a luciferase reporter gene under the control of the human minimal IL-2 proximal promoter into the genome of Jurkat T-cells. Upon stimulation with PMA and ionomycin, the pharmacologic mimics of TCR, a 20-fold increase in luciferase activity was observed (data not shown). Using the reporter cell line, we screened a library of mostly FDA-approved drugs at a final concentration of 10 µM using the IL-2 reporter assay in 96-well format. The known immunosuppressive drugs CsA and FK506 were both positive hits, validating the screen. Although it was not the most potent hit, we decided to further investigate clofazimine (FIG. 1).

Figure 1B:
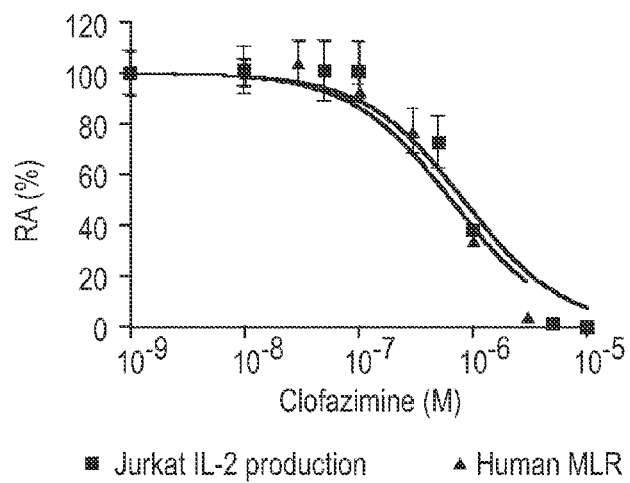

The ability of clofazimine to inhibit TCR-mediated IL-2 production was confirmed using transiently transfected IL-2 luciferase reporter gene in Jurkat T-cells and a freshly prepared clofazimine stock solution. Clofazimine inhibited PMA/ionomycin-stimulated IL-2 luciferase reporter gene activation with an $IC_{50}$ of 22 nM (FIG. 1A). It also inhibited the activation of endogenous IL-2 promoter in response to PMA and thapsigargin with an $IC_{50}$ of 1.1 µM (FIG. 1B). Importantly, clofazimine inhibited human mixed lymphocyte reaction with an $IC_{50}$ of 0.9 µM (FIG. 1B), similar to its effect on endogenous IL-2 production in Jurkat T-cells.

Figure 1C:
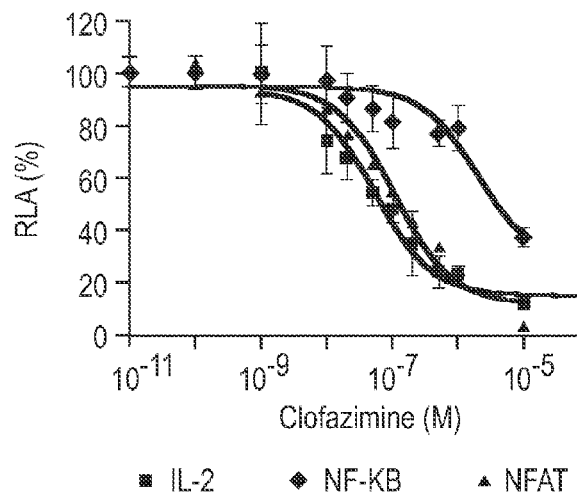
Figure 1D:
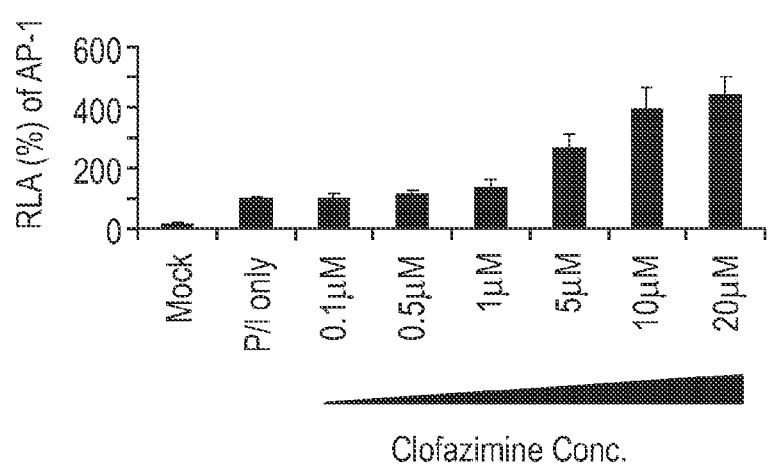
Figure 6A:
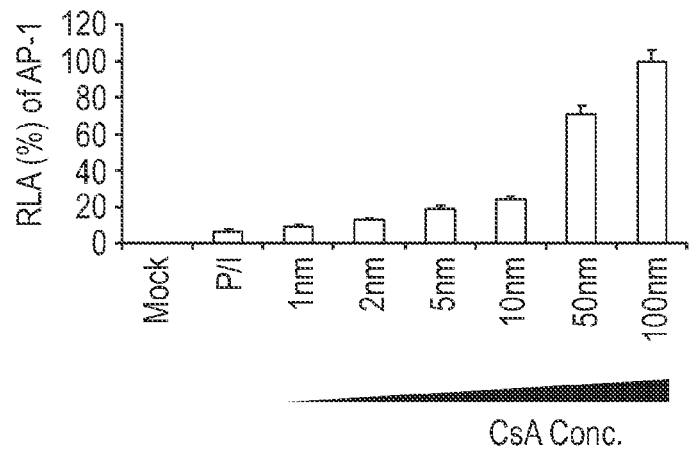
FIG. 6. Effects of clofazimine on AP-1 luciferase reporter gene and the nuclear translocation of NFAT in response to ionomycin treatment. (A) Dose-dependent enhancement of the AP-1 luciferase reporter gene by CsA (n=6). (B) Clofazimine inhibits EGFP-NFATc3 nuclear translocation in Jurkat T-cells stimulated by 1 μM ionomycin. Images were taken 30 minutes after addition of ionomycin. (C) Dose-dependent inhibition of ionomycin-stimulated NFAT nuclear translocation by clofazimine (n=3).
Figure 6B:
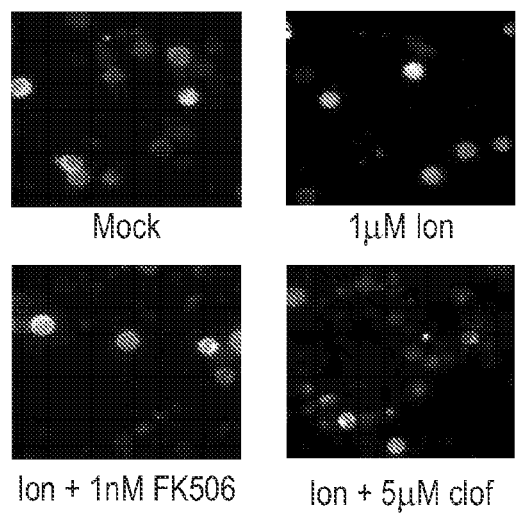
Figure 6C:
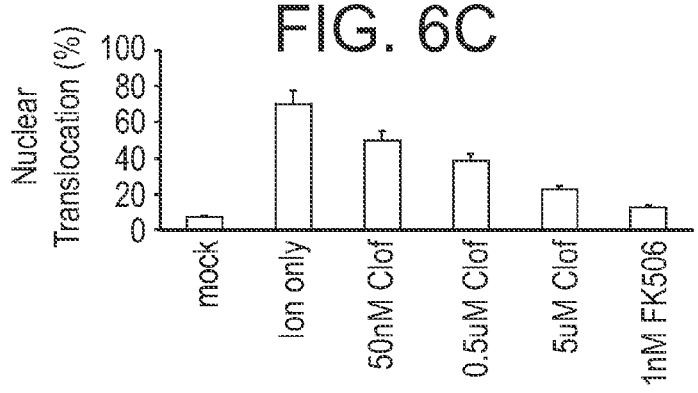

The transcription activation of the IL-2 promoter is dependent on three key transcription factors, NF-AT, NF-κB and AP-1. We thus determined whether clofazimine affected the activation of each of those transcription factors using their respective luciferase reporters. As shown in FIG. 1C, while the NFAT luciferase reporter was as sensitive to clofazimine as the IL-2 promoter-driven luciferase reporter gene, the NF-κB luciferase reporter is about 40-fold less sensitive to clofazimine. In contrast, the AP-1 luciferase reporter gene activity was enhanced, rather than inhibited, by higher concentrations of clofazimine (FIG. 1D). A similar stimulation of the AP-1 reporter was also observed at higher concentrations of CsA (FIG. 6A), suggesting that clofazimine may affect the same signaling pathway as CsA.

Figure 1E:
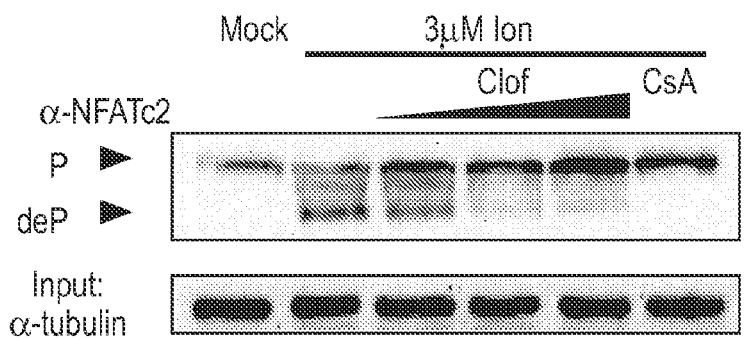
Figure 7A:
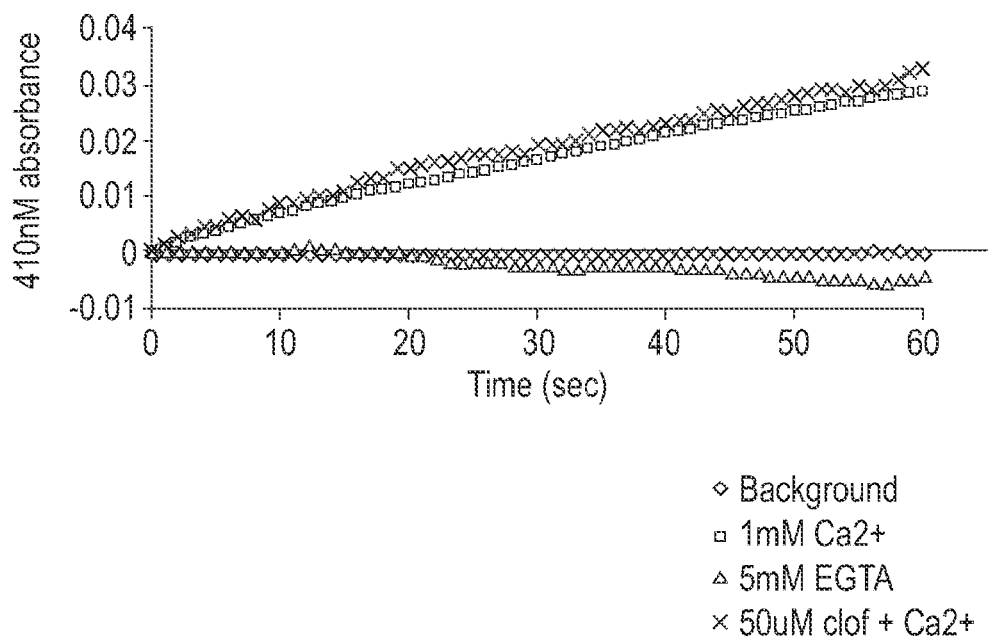
FIG. 7. Clofazimine does not affect the enzymatic activity of calcineurin in vitro. (A) Clofazimine does not inhibit the protein phosphatase activity of calcineurin in vitro. 20 mM p-nitrophenylphosphate was incubated with purified recombinant calcineurin A/B and calmodulin in the presence of 1 mM calcium or 5 mM EGTA at 30° C. The progress of the reaction was followed by absorbance at 410 nm every 0.5 second. Representative curves of three different experiments. (B) Clofazimine does not inhibit NFATc2 dephosphorylation by calcineurin in vitro. NFATc2 was immuno-precipitated from Jurkat lysate and incubated with recombinant calcineurin A/B and calmodulin for 30 min at room temperature in the presence of 1 mM $Ca^{2+}$ or 5 mM EGTA. The reaction mixtures were subjected to SDS-PAGE, followed by Western blot using anti-NFAT antibodies. (C) Clofazimine does not interfere with calcineurin-NFATc2 interaction. GST-NFATc2 (1-415) was purified by glutathione-sepharose beads and incubated with Jurkat cell lysate. The pull-down products were resolved by SDS-PAGE and detected by α-calcineurin antibody. (D) Clofazimine does not affect binding calcineurinA (1-400, H160N) and NFATc2 (1-415) in Jurkat T-cells in a mammalian two-hybrid assay. But it inhibits the calcium-dependent enhancement of the calcineurin-NFATc2 interaction. (n=6)
Figure 7B:
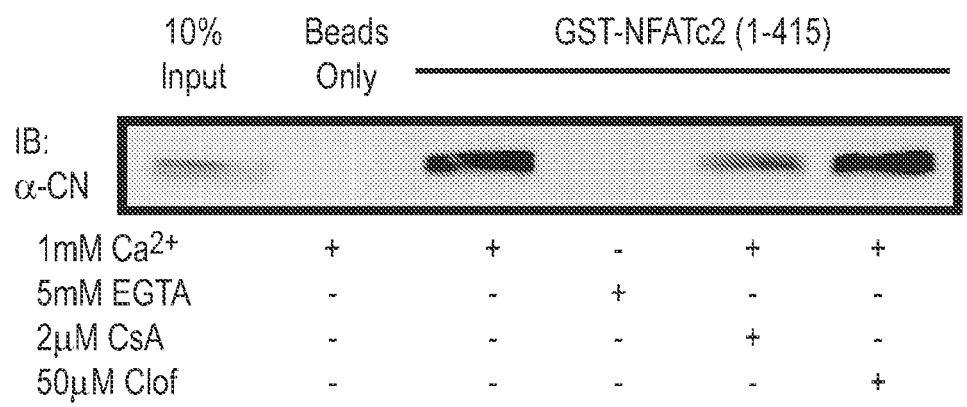

The selective inhibitory effects of clofazimine on both NFAT and NF-κB over AP-1 suggested that it is likely to affect the activation of their common upstream regulator, the protein phosphatase calcineurin. To assess this possibility, we determined whether clofazimine, like CsA and FK506, affected the dephosphorylation of endogenous NFAT in response to ionomycin treatment. Similar to CsA, clofazimine inhibited ionomycin-induced dephosphorylation of NFATc2 in a dose-dependent manner (FIG. 1E). In addition, clofazimine also blocked the ionomycin-induced nuclear translocation of NFAT in Jurkat T-cells (Figure S1 B-C). Together, these results indicated that clofazimine inhibited the activation of the protein phosphatase calcineurin in vivo. We then examined the effects of clofazimine on calcineurin in vitro. Clofazimine had no effect on the enzymatic activity of calcineurin with either para-nitrophenylphosphate or immunoprecipitated endogenous NFATc2 as substrates (FIGS. 7A and 7B). Nor did it affect the binding of GST-NFATc2 to recombinant calcineurin (FIG. 7C). Interestingly, when the association between the N-terminal fragment of NFAT and the constitutively active form of calcineurin (CnΔC) was examined in a mammalian two-hybrid assay, clofazimine inhibited the calcium-dependent NFAT-calcineurin interaction in a dose-dependent manner (FIG. 7D). Thus, clofazimine appeared to act at a step upstream of calcineurin activation in vivo, raising the possibility that it affected either the release of intracellular calcium or calcium influx through the plasma membrane calcium channels.

Figure 2A:
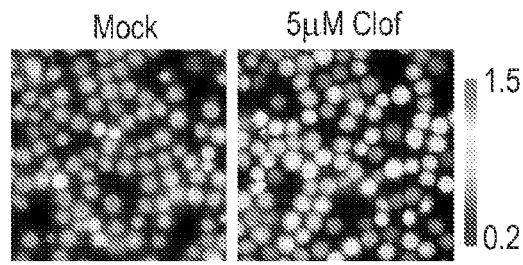
FIG. 2. Clofazimine interferes with calcium influx in Jurkat T-cells. (A) Calcium influx was inhibited by clofazimine in a heterogeneous fashion. Clofazimine was added 5 minutes before stimulation with 1 µM TG. Representative images were taken 30 minutes after 2 mM calcium was added. The color gradient represents fura-2 350 nm/380 nm excitation ratio. (B) Effects of clofazimine on store-depletion induced calcium influx. Typically the cells can be divided into 2 groups, the responsive (red) and none-responsive (pink) populations. Each curve represents average signal of 20 cells from the same field in (A) (The results were reproduced 10 times under the same condition). (C) Effect of clofazimine on calcium oscillation in Jurkat T-cells (representative of 56 cells). The oscillation was stimulated by 10 nM TG. (D) Clofazimine elongated oscillation period in more than 80% of Jurkat T-cells (Results represented 3 experiments, at least 80 cells were counted for each experiment).
Figure 2B:
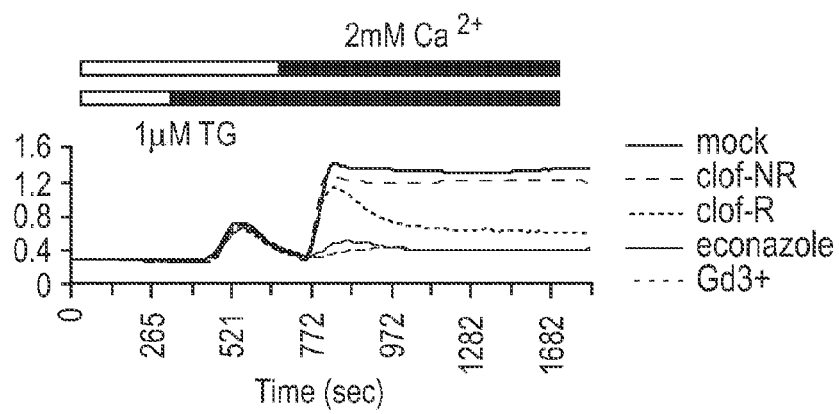
Figure 8A:
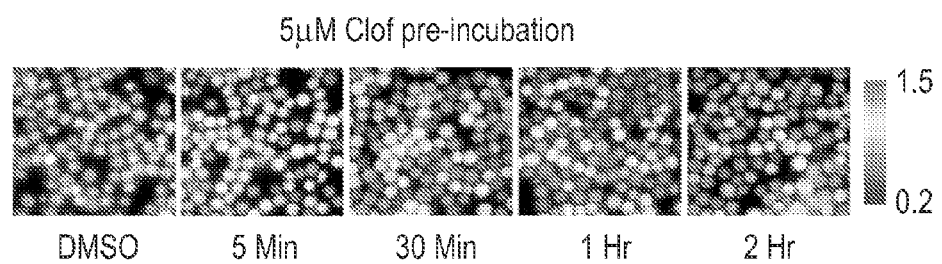
FIG. 8. Clofazimine alters calcium oscillation patterns in Jurkat T-cells without affecting reconstituted $I_{CRAC}$ in HEK293 cells. (A, B) Time-dependent increase in the population of cells that are sensitive to clofazimine. Jurkat T-cells were incubated with clofazimine for varied lengths of time before 1 μM TG was added. Images were taken 30 min after 2 mM calcium was added. (C) Average CRAC current densities at −80 mV induced by $IP_3$ (20 μM) in stable STIM1 expressing HEK293 cells transiently overexpressing CRACM1, CRACM2 and CRACM3. Holding potential was at 0 mV. The bar indicates the time for clofazimine application.
Figure 8B:
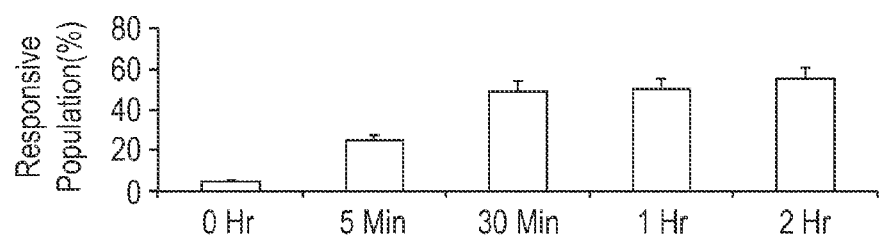
Figure 8C:
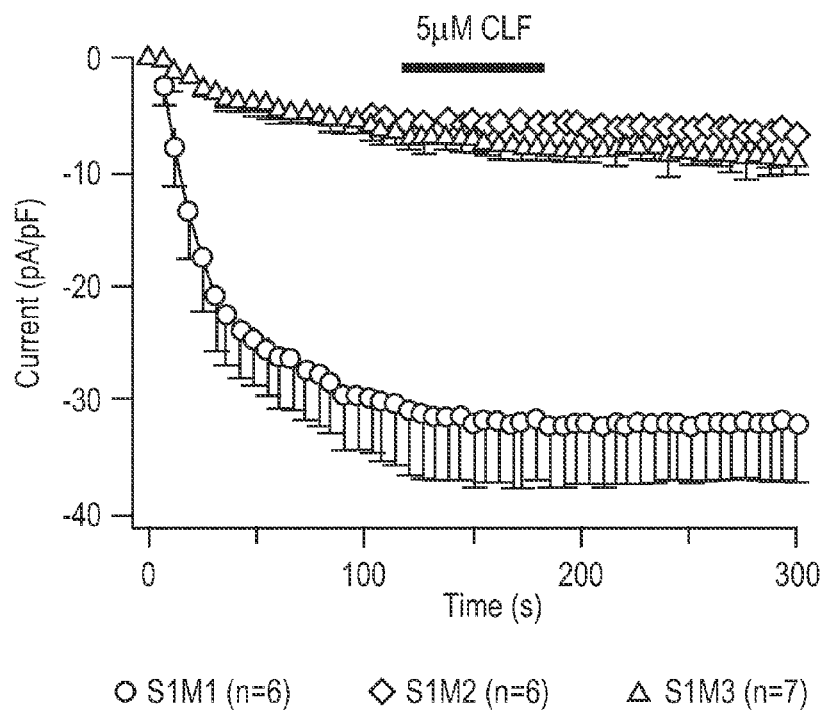

We employed live cell imaging to determine the effect of clofazimine on changes in intracellular calcium concentrations in response to thapsigargin treatment. Using the calcium indicator dye Fura-2AM, we were able to observe entry of calcium into Jurkat T-cells upon treatment of cells with thapsigargin followed by addition of 2 mM $Ca^{2+}$ into the extracellular medium (FIG. 2A). Pretreatment of Jurkat T-cells with known CRAC channel inhibitors econazole or gadolinium abrogated calcium entry as expected (FIG. 2B). However, when cells were preincubated with clofazimine for 5 min, the calcium entry of only about a quarter of cells are responsive to inhibition by the drug (FIG. 2B). When the preincubation time was increased to up to 2 h, there was a time-dependent increase in the proportion of cells that becomes sensitive to clofazimine (FIGS. 8A and 8B). That only a quarter of Jurkat T-cells are responsive to inhibition by clofazimine at 5 min may reflect the heterogeneity of this cell line. The precise underlying cause of the time-dependent increase in clofazimine-responsive cell population, however, remains unknown. The effect of clofazimine on the extracellular calcium influx suggested that it might affect the CRAC channel. We thus examined the effects of clofazimine in reconstituted CRAC channels using ectopically expressed CRACM 1 (Orai 1), CRACM2 or CRACM3 subunits co-expressed with STIM1 in HEK 293T-cells. But we observed no effects of clofazimine on the reconstituted CRAC current (FIG. 8C), ruling out the possibility that clofazimine directly interacts and interferes with the known components of the CRAC channel.

Figure 2C:
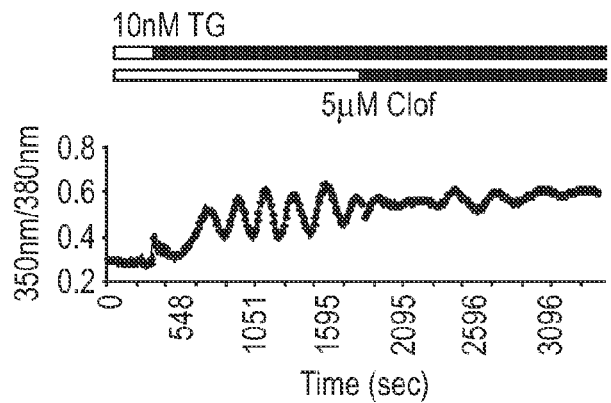
Figure 2D:
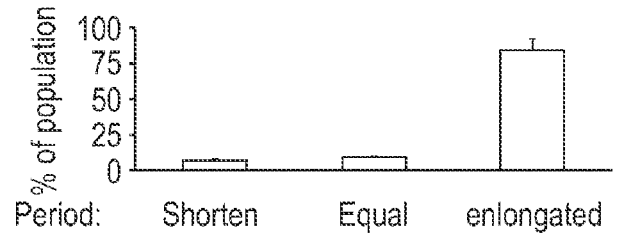

Given that clofazimine inhibited calcineurin activation in T-cells, we next determined whether clofazimine affected the oscillation frequency of the CRAC current in Jurkat T-cells, which has been shown to be critical and selective for sustained activation of calcineurin and NFAT to drive cytokine gene expression. Indeed, addition of clofazimine significantly disrupted the oscillation patterns of the CRAC current induced by a low concentration of thapsigargin. It both decreased the amplitude and increased the period of the calcium oscillation (FIG. 2C). Over 80% of cells exhibited elongation of the oscillation period upon treatment with clofazimine, indicating that this effect is statistically significant (FIG. 2D).

The pronounced effects of clofazimine on the oscillation patterns of calcium current, together with the lack of effect of clofazimine on reconstituted CRAC current, raised the possibility that it may affect other channels, particularly potassium channels, which are known to regulate the CRAC current. We thus determined the effects of clofazimine on the activity of various known CRAC-regulating-channels expressed in activated T-cells. As shown in FIGS. 3A and 3B, clofazimine had a dramatic effect on Kv1.3 current in a time- and dose-dependent manner. It inhibited the Kv1.3 potassium current with an $IC_{50}$ of 300 nM and a Hill's coefficient of 0.75 (FIG. 3C), consistent with its potency for the inhibition of both endogenous IL-2 production in Jurkat T-cells and the human mixed lymphocyte reaction (FIG. 1B). In contrast, the activity of several other channels known to modulate CRAC current in T-cells, including the calcium-activated IKCa1 potassium channel and the TRPM4 channel, remained unaffected by clofazimine at up to 10 μM concentration (data not shown).

Figure 12:
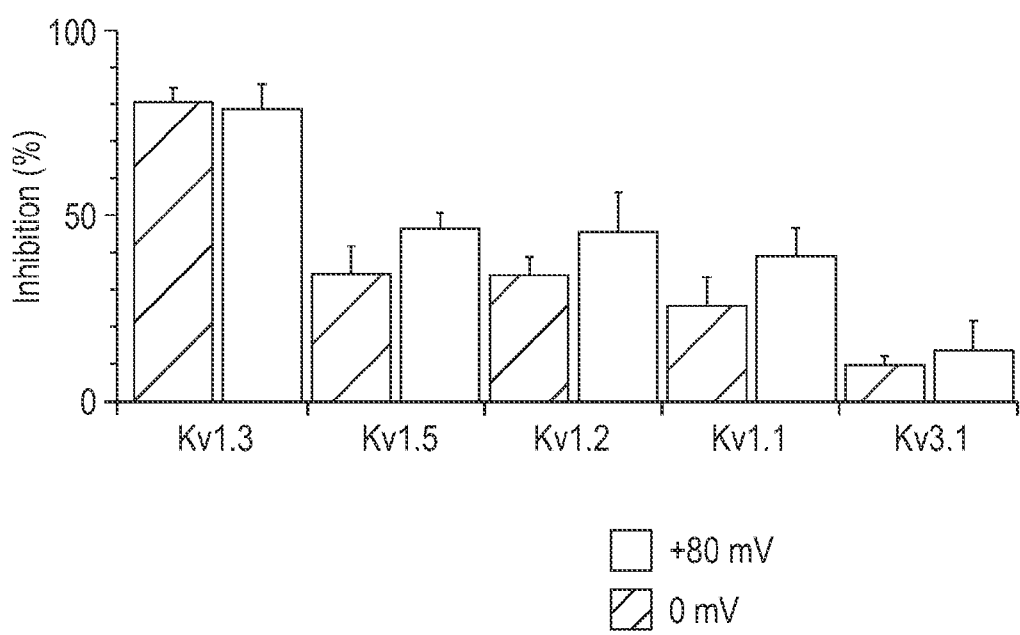
FIG. 12. Inhibition of Kv channels by 10 μM clofazimine assessed at 0 mV (red bars) or +80 mV (black bars). Same cells as in FIG. 3D and FIG. 11. Note the increased inhibitory effect at 0 mV for all Kv channels displayed except Kv1.3.

To further investigate the specificity of clofazimine, we conducted a series of experiments testing the drug against several heterologously expressed potassium channels, including mouse Kv1.3. As shown in FIGS. 3D and 3E, clofazimine strongly suppressed mouse Kv1.3 stably expressed in L929 cells with an $IC_{50}$ of 470 nM and a Hill coefficient of 0.5 (FIG. 3F). All other Kv channel species tested (Mouse Kv1.1, rat Kv1.2, human Kv1.5 and mouse Kv3.1 proved considerably less sensitive to clofazimine, blocking less than 50% of current at a 10 μM concentration (FIG. 11). This indicates that their $IC_{50}$ values for clofazimine are above 10 μM. Interestingly, there seems to be some voltage dependence to the effect on Kv channels other than Kv1.3, since the clofazimine block is smaller at 0 mV compared to +80 mV (FIG. 12). Since most cells do not depolarize beyond 0 mV, at least not for appreciable amounts of time, this represents the more physiologically relevant parameter in regards to the inhibitory effect of clofazimine. Taken together, these data suggest that clofazimine is highly selective for the Kv1.3 channel.

Figure 4A:
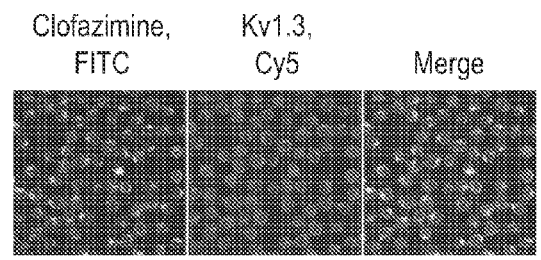
FIG. 4. (A) Clofazimine colocalizes with Kv1.3 on the plasma membrane of Jurkat T-cells. Clofazimine was visualized in FITC channel while Kv1.3 was stained by Cy5 secondary antibody. (B) Over-expression of Kv1.3 in Jurkat T-cells resulted in resistance of the IL-2 luciferase reporter to CLF. The $IC_{50}$s for different curves (Kv1.3 overexpression from low to high) are 41.6±8.4 nM, 41.0±14.5 nM, 386±214 nM, 1.37±0.52 µM and 1.46±0.63 µM (n=6). (C) Kv1.3 knockdown resulted in an increase in sensitivity of the IL-2 luciferase reporter to CLF. The $IC_{50}$s for control EGFP-siRNA lentiviral transduced Jurkat T-cells (control) was 49.9±13.0 nM, while that for shKv1.3-4 transduced cells was 10.5±2.4 nM (n=6). (D) Lentivirus-mediated knockdown of Kv1.3 assessed by Western blot. Normalized with control virus, lentivirus 4 reduced Kv1.3 expression level by 65%.

Kv1.3 is known to exhibit a polarized cell surface expression pattern, which can be visualized using polyclonal antibodies in conjunction with Cy5-labeled secondary antibodies (FIG. 4A). We took advantage of the intrinsic fluorescence of clofazimine, which can be detected using the same filter for FITC and compared the distribution patterns of clofazimine and Kv1.3. Indeed, clofazimine displayed the same subcellular localization pattern as that of Kv1.3 (FIG. 4A), suggesting that clofazimine is likely to be associated with Kv1.3 in vivo.

Figure 4B:
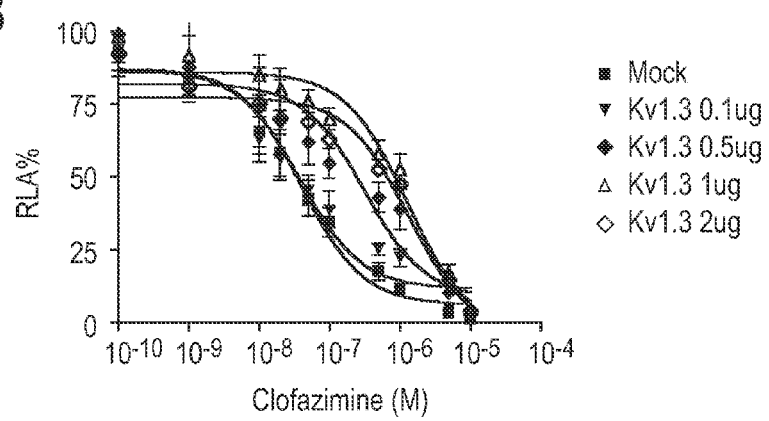
Figure 4C:
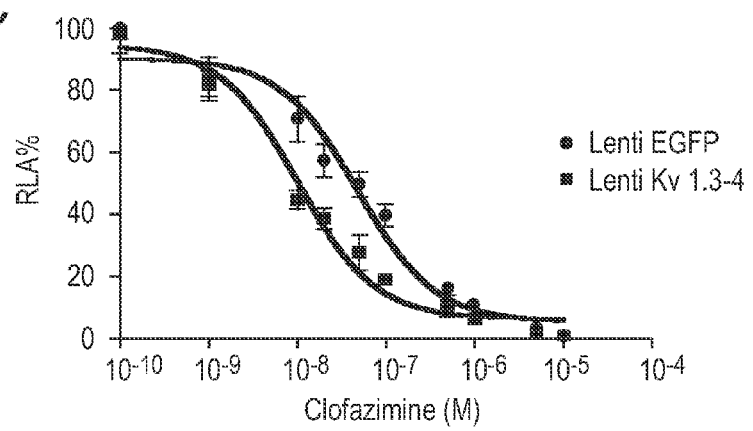
Figure 4D:
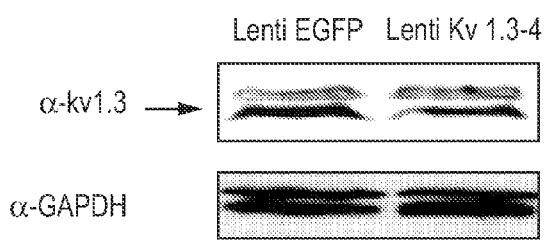
Figure 9:
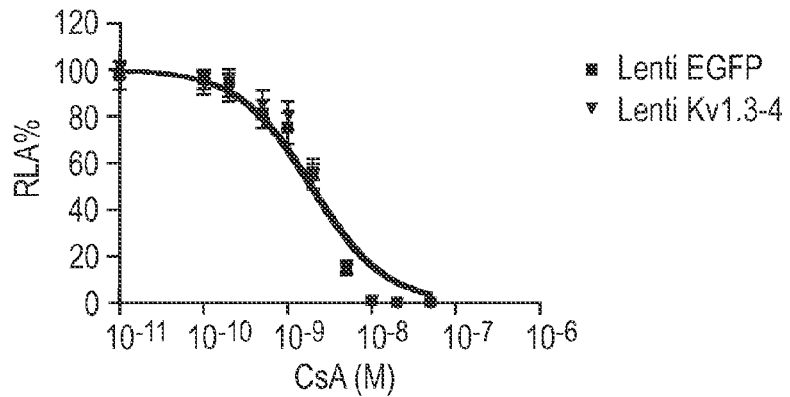
FIG. 9. Knockdown of Kv1.3 did not affect the sensitivity of the IL-2 luciferase reporter to CsA. The $IC_{50}$ for control EGFP-siRNA lentiviral transduced Jurkat T-cells was 2.5±0.6 nM, and that for Kv1.3 lentiviral 4 transduced T-cells was 2.6±0.7 nM (n=6).

To further assess the physiological relevance of Kv1.3 as a molecular target for clofazimine, we first determined the effects of ectopic overexpression of Kv1.3 on the sensitivity of the IL-2 reporter gene to clofazimine. As shown in FIG. 4B, overexpression of Kv1.3 led to a gain in resistance of the IL-2 reporter to clofazimine in a dose-dependent manner. At the highest concentration of Kv1.3 expression plasmid used (2 μg), there was a 35-fold increase in the $IC_{50}$ value of clofazimine. Next, we downregulated the expression of endogenous Kv1.3 using lentivirus-mediated RNA interference. Of a total of nine constructs tested, the most effective construct, shKv1.3-4, partially downregulated the protein level of Kv1.3 by ca. 65% (FIG. 4D). A comparison of the dose-response curves of Jurkat cells transduced with shKv1.3-4 lentiviruses and those transduced with viruses carrying shRNA against EGFP revealed that knockdown of Kv1.3 increased the sensitivity of the IL-2 luciferase reporter to clofazimine with a nearly 5-fold decrease in the $IC_{50}$ values for clofazimine (FIG. 4C). In contrast, knockdown of Kv1.3 had no effect on the sensitivity of the IL-2 luciferase reporter to CsA (FIG. 9). The changes in the sensitivity of the IL-2 reporter gene to clofazimine upon overexpression or knockdown of Kv1.3 provide strong support for the notion that Kv1.3 is a specific molecular target of clofazimine.

Figure 5A:
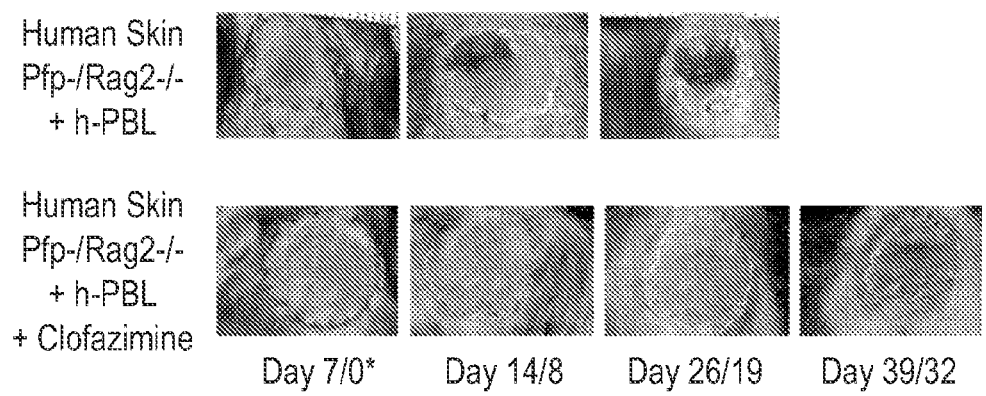
FIG. 5. Clofazimine inhibits human T-cell-mediated skin graft rejection in immunodeficient mice. (A) Representative skin grafts at different days post-transplantation. Human foreskin was transplanted onto Pfp/Rag2−/− mice. $1.0 \times 10^8$ human peripheral blood lymphocytes (PBL) were adoptively transferred into each animal at Day 7 post-transplantation. Administration of clofazimine or carrier control (olive oil) was also initiated at Day 7. * Days after skin transplantation/cell transfer. (B) Effect of clofazimine on the mean survival time of transplanted human (n=5) and mouse (n=4) skin grafts. The mouse skin transplantation was performed using Balb/c mice as skin donors, B6 Rag1−/− mice as recipients and PBL from B6 for adoptive transfer.
Figure 5B:
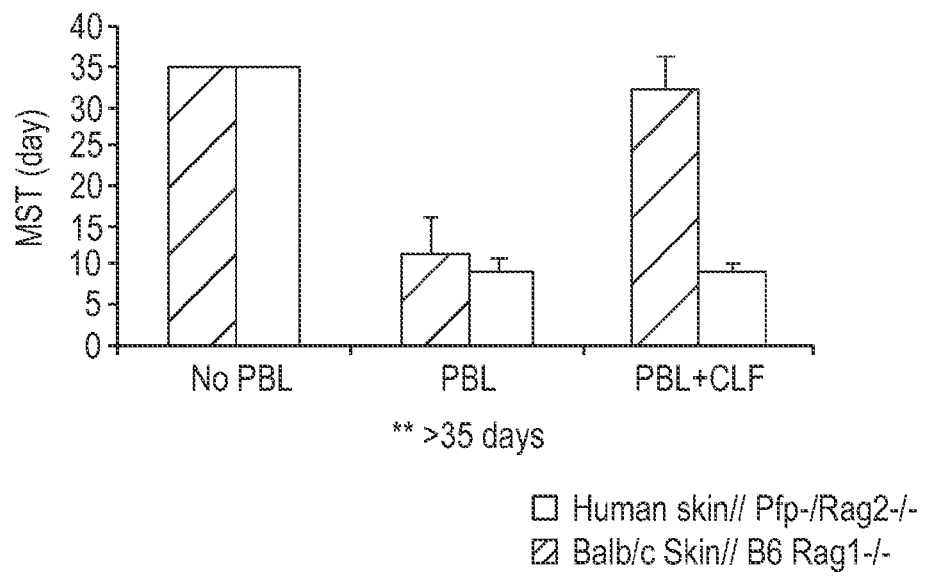
Figure 10A:
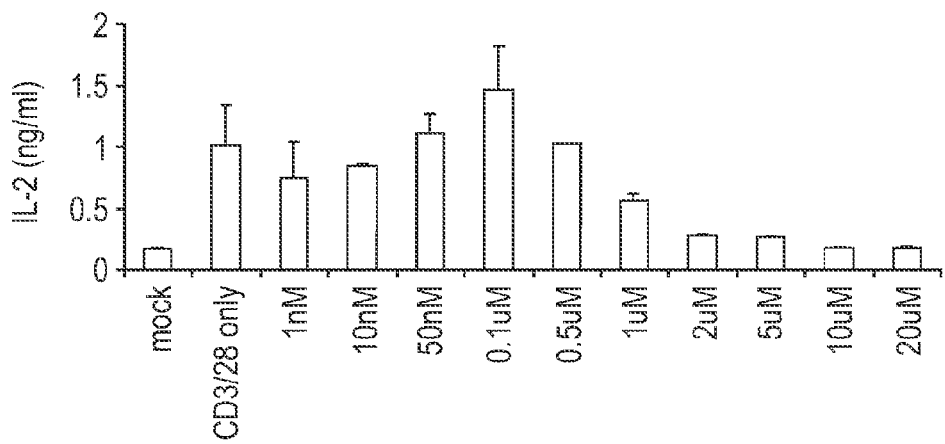
FIG. 10. Effects of clofazimine on mouse TCR-mediated IL-2 production and mixed lymphocyte reaction in murine T-cells. (A) Dose response of IL-2 production from anti-CD3/anti-CD28-stimulated mouse primary T-cells to different concentrations of clofazimine (n=3). (B) Biphasic effects of clofazimine on mouse mixed lymphocyte reaction (n=3).
Figure 10B:
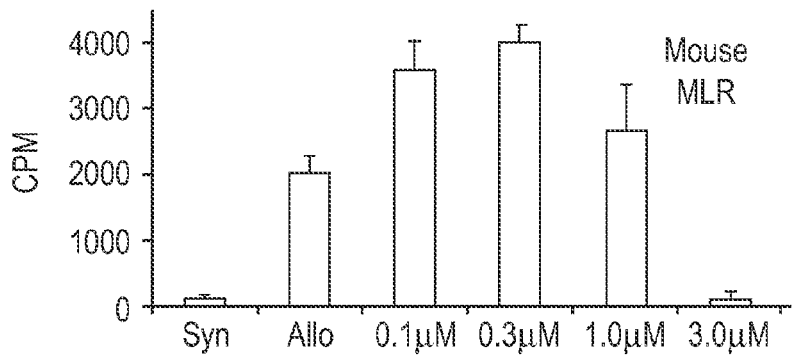
Figure 11A:
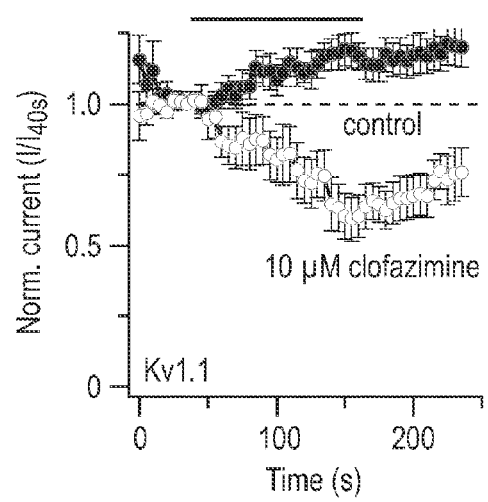
FIG. 11. Effect of 10 μM clofazimine on heterologous Kv1.1, Kv1.2 Kv1.5 and Kv3.1. (A) Average time course of mouse Kv1.1 currents stably expressed in L929 cells. Control cells (closed circles, n=5, no application) and cells superfused with 10 μM clofazimine added to the standard extracellular solution (open circles, n=6) as indicated by the black bar. Voltage protocol, solutions and analysis as outlined in FIG. 3D. (B) Current-voltage relationship (IN) of a representative cell expressing mouse Kv1.1 with control IN (black) extracted at 40 s after whole-cell establishment and the IN for clofazimine extracted at the end of application (red, 160 s). (C) Average time course of heterologous rat Kv1.2 expressed in B82 cells. Control cells (closed circles, n=5, no application) and cells superfused with 10 μM clofazimine (open circles, n=5, black bar indicates application time) are shown. Acquisition and analysis as in (A). (D) IN of a representative cell expressing rat Kv1.2 with control IN (black) extracted at 40 s after whole-cell establishment and the IN for clofazimine extracted at the end of application (red, 160 s). (E) Average time course of heterologous human Kv1.5 expressed in MEL cells. Control cells (closed circles, n=5, no application) and cells superfused with 10 μM clofazimine. (open circles, n=5, black bar indicates application time) are shown. Acquisition and analysis as in (A). (F) IN of a representative cell expressing human Kv1.5 with control IN (black) extracted at 40 s after whole-cell establishment and the IN for clofazimine extracted at the end of application (red, 160 s). (G) Average time course of heterologous mouse Kv3.1 expressed in L929 cells. Control cells (closed circles, n=5, no application) and cells superfused with 10 μM clofazimine (open circles, n=5, black bar indicates application time) are shown. Acquisition and analysis as in (A). (H) IN of a representative cell expressing mouse Kv3.1 with control IN (black) extracted at 40 s after whole-cell establishment and the IN for clofazimine extracted at the end of application (red, 160 s).
Figure 11C:
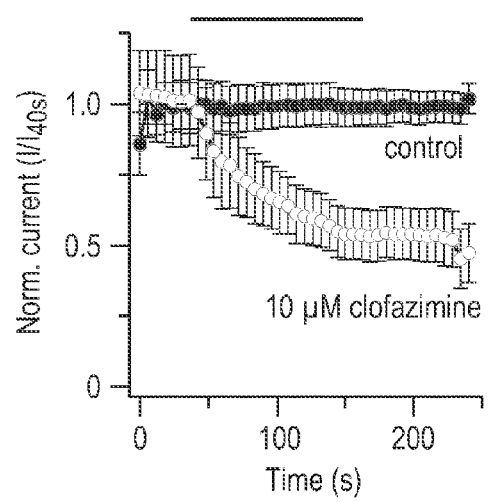
Figure 11B:
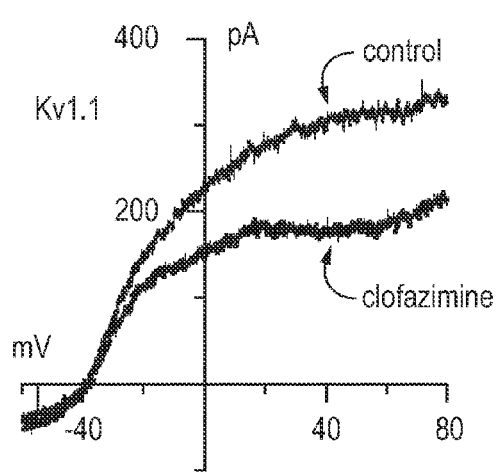
Figure 11D:
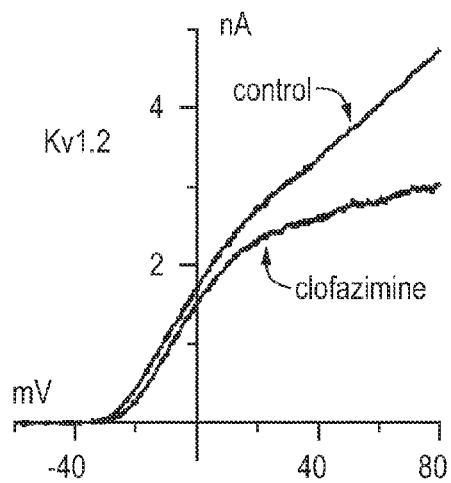
Figure 11E:
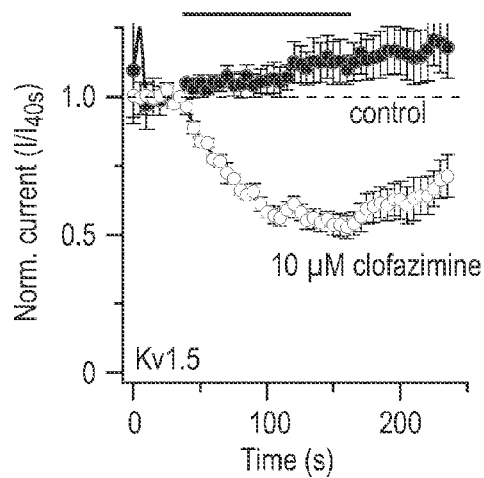
Figure 11G:
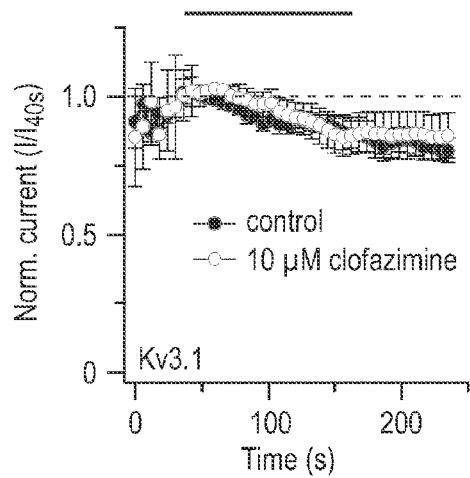
Figure 11F:
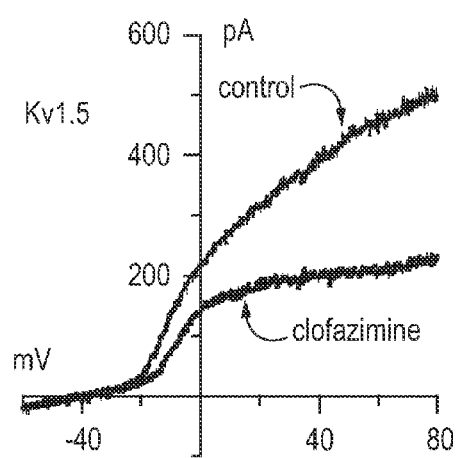
Figure 11H:
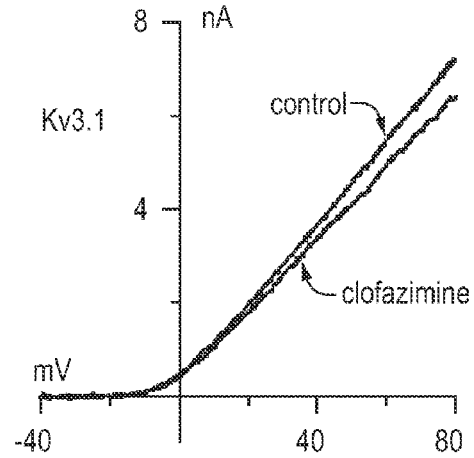

Kv1.3 has been implicated in T-cell activation and has served as a molecular target for developing novel immunosuppressive agents. Given that clofazimine is already used in the clinic, albeit for a completely different indication, we wondered whether it is efficacious in animal models of organ transplantation. Initial experiments using mouse skin or heart transplant models failed to show any beneficial effects of clofazimine in those models. These negative results are not surprising given that Kv1.3 plays distinct roles in humans and rodents, as it has been shown that Kv1.3 is dispensable in mice due to the up-regulation of other chloride channels. Consistent with this notion, we also failed to observe a dose-dependent inhibition of IL-2 production in primary mouse T-cells (FIG. 10A) and murine mixed lymphocyte reaction (FIG. 10B). Moreover, similar results were obtained for mixed lymphocyte reaction using cells derived from rats, making it difficult to evaluate the in vivo effects of clofazimine using well-established animal models. To overcome this problem, we turned to a model of reconstituted human T-cell-mediated human skin rejection in immunodeficient mice. We thus transplanted human foreskin into Pfb-Rag2–/– mice that lack T, B and NK cells. Upon healing of the skin graft for about 7 days, a total of 100 million human peripheral blood lymphocytes from an unrelated donor were adoptively transferred into the same animals. The animals were treated orally with either DMSO (control) or clofazimine at 50 mg/kg/day for a total of 10 days (FIG. 5A). For the control group, the transplanted foreskin was rejected with a median survival time of 11 days (FIG. 5B). For the group treated with clofazimine, the skin survived even beyond the cessation of the drug treatment with a mean survival time of 35 days (FIG. 5B), which is comparable to the efficacy for FK506 treatment (data not shown). It is noteworthy that in a parallel experiment using murine skin and total murine T-cells, clofazimine had no effect on the survival of murine skin transplant (FIG. 5B). Together, these results demonstrated that clofazimine is uniquely effective in inhibiting human T-cell-mediated graft rejection with no significant effect on murine T-cells.

Example 2 shRNA Lentivirus Production

The targeting sequence of sh Kv1.3-4 is 5'-GCCACCT-TCTCGCGAAACAT-3' (SEQ ID NO: 1). Recombinant lentiviruses were generated using a three-plasmid system described (Pan et al. 2004. *J. Biol. Chem.* 279:14477). Virus was harvested and concentrated (1:50) 2 days after transfection. Jurkat T-cells were transduced by concentrated virus at a ratio of $5\times10^6$ cells/150 µl virus. Cells were cultured for two days before they were harvested for Western blot analysis and other experiments.

Example 3

Human Mixed Lymphocyte Reaction (MLR)

The human MLR was established by coculturing normal human PBMN responder lymphocytes ($0.5\times10^6$) with an equal number of miomycin C-treated stimulator cells in RPMI1640 complete medium. The cells were incubated with varying doses of clofazimine at 37° C. in a humidified atmosphere of 5% $CO_2$ for 4 days. Then 1 µCi of [$^3$H]-thymidine was added into culture and incubation was continued for 6 h. The cells were harvested and [$^3$H]-thymidine incorporated into cells was measured in a liquid scintillation counter.

Example 4

Mouse Model of Human Skin Transplantation

The experimental procedure is similar to that described previously. Clofazimine suspension in olive oil was administered p.o. at 50 mg/kg/day in a total volume of 0.2 ml per administration.

Example 5

Oral Formulation that Forms an Emulsion Upon Introduction to Aqueous Environment of Gastro-Intestinal Tract (US 20040142040A1)

A first self-emulsifying nanosuspension containing clofazimine can be prepared by dispersing clofazimine nanoparticles in capric acid and Cremophor EL. The nanoparticles can be prepared by wet milling (using, for example, Dyno milling equipment) followed by freeze-drying. Pluronic F108 can be used as a coating agent in the wet milling process. The mean particle size of the nanoparticles can be measured by Horiba LA-910 laser scattering particle size analyzer or similar equipment. Clofazimine can be dispersed within the capric acid and Cremophor EL using a sonicator, with an example resulting self-emulsifying nanosuspension including 3.8 wt % clofazimine nanoparticle, 1.4 wt % Pluronic F108, 47.4 wt % capric acid, and 47.4 wt % Cremophor EL.

A batch of hard-cap controlled release dosage forms according to the present invention can then be manufactured using the first self-emulsifying formulation. The first dosage forms can be prepared using clear hard-caps which may be of size-0 or other sizes. The first dosage forms can incorporate a bi-layer osmotic composition and can be coated with a rate controlling semipermeable membrane. An exit orifice can be provided in the first dosage forms using a mechanical drill with drilling depth control.

To prepare the bi-layer osmotic composition used in the dosage forms, an osmotic granulation can be prepared using a Glatt fluid bed granulator (FBG) or similar equipment. The osmotic granulation can include NaCl, sodium carboxymethylcellulose (NaCMC), hydroxypropylmethylcellulose (HPMC), hydroxypropyl cellulose (HPC), Mg stearate and red ferric oxide. The NaCl can be sized/screened using a Quardo mill having a 21-mesh screen and the speed set on maximum (or similar equipment). The sized NaCl, NaCMC, HPMC, and red ferric oxide can be blended in a granulator bowl in the following weight percentages: 58.75% NaCMC, 30% sized/screened NaCl, 5.0% HPMC E-5 and 1.0% red ferric oxide. In a separate container, a granulating solution can be prepared by dissolving 5.0 wt % HPC EF in purified water. The osmotic granulation can then be prepared by spraying the granulation solution onto the fluidized powders until all of the solution is applied and the powders are granular. A final osmotic granulation can be completed by blending 0.25 wt % Mg stearate with the prepared granules.

The barrier layer to be included in the bi-layer osmotic composition to be included in the first hard-cap controlled release dosage forms can be formed using Kollidon SR. The final osmotic granulation can be used to prepare a bi-layer osmotic composition by compressing an amount of the final osmotic granulation and an amount of Kollidone SR into a bi-layer tablet using Carver tableting press (or similar equipment). Two hundred and seventy mg of the final osmotic granulation can be added to a 0.70 cm punch (lower punch: modified ball, upper punch: modified) and then can be tamped. 80 mg of Kollidone SR can then be added to the punch and the osmotic granulation and Kollidone SR can be compressed under a force of about 1 metric ton to form a tableted bi-layer osmotic composition.

To load the self-emulsifying nanosuspension into the capsules to be used to prepare the first hard-caps, the capsules can be separated into two segments (a body and a cap). The self-emulsifying nanosuspension can then be loaded into the body of each capsule using standard filling techniques. Each capsule can be provided with 526 mg of the self-emulsifying nanosuspension. The clofazimine dose of the resulting hard-cap controlled release dosage form can be, therefore, about 20 mg. After the capsule bodies are filled, pre-coating assemblies can be formed by positioning a bi-layer osmotic composition in each filled capsule body.

The pre-coating assemblies can then be coated with a semipermeable membrane. The semipermeable membrane can be provided over the pre-coating assemblies included, by weight, 70% cellulose acetate 398-10 and 30% Pluronic F-68. To form the semipermeable membrane, a coating composition can first be formed by dissolving appropriate amounts of cellulose acetate 398-10 and Pluronic F-68 in acetone to form a coating solution having a solid content of 4% by weight. The pre-coating assemblies can then be sprayed with the coating solution in a 12" Freud Hi-coater (or similar equipment) until each is provided with a semipermeable membrane weighing about 131 mg.

After membrane coating, the first hard-cap controlled release dosage forms can be completed by drying the coated sub-assemblies and providing each of the dried and coated sub-assemblies with an exit orifice. The coated sub-assemblies can be dried in a Blue oven at 30° C. overnight, and each of the dried sub-assemblies can then be provided with an exit orifice measuring about 0.5 mm in diameter. The exit orifices can be provided in each dosage form by drilling the drug-layer side using a mechanical drill with drilling depth control.

The release rate profile of the first hard-cap controlled release dosage forms can be measured using a USP II paddle method in 2%, by weight, aqueous solution of Pluronic F108 (pH 6.8).

Example 6

Controlled Release Oral Formulation that Targets Drug to Small Intestine (U.S. Pat. No. 5,641,745)

Biodegradable micro- and nanospheres containing 25 to 80% w/w clofazimine can be suitably prepared herein by a solvent evaporation/extraction procedure from an emulsion-system (Ramtoola et al. *The Journal of Microencapsulation.* 1992 9:415-23). The polymers used can be poly-D,L-lactide having a MW of 16,000 and intrinsic viscosity (i.v.) of 0.2 dl/g (R-203; Boehringer Ingelheim) or poly-D,L-lactide-co-glycolide 50:50 of i.v. 0.5 dl/g (RG-504; Boehringer Ingelheim).

Clofazimine and the encapsulating polymer can be dissolved in methylene chloride. Suitable methylene chloride to polymer ratios are 1-2 ml methylene chloride/g of R-203 and 3 ml of methylene chloride/g of RG-504. This drug/polymer solution can then be suitably emulsified in an aqueous PVA solution (suitably 0.27%) in a ratio of about 10 ml of the drug/polymer solution to 100 ml of the PVA solution and mixed at high speed (suitably 20,000-24,000 rpm) for 2 min followed by stirring at 1000 rpm for 2 hr. The particles can be recovered by centrifugation and dried overnight in a vacuum oven.

The particles produced can be characterized by scanning electron microscopy (such as S360, Leica, Cambridge) and sized using a Malvern 2600 Laser Sizer or similar equipment. The particles can also be characterized by X-ray diffraction (such as Daco-MP 500, Siemens). The drug content of the microparticles can be assayed by HPLC using a Novapak C8 column at 70° C. using a mobile phase of acetronitrile:water:methanol:phosphoric acid (900:525:75:0.075) at a flow rate of 2 ml/min with UV detection at 210 nm. The solubility of clofazimine can be measured at 37° C. in increasing concentrations of sodium lauryl sulfate (SLS) solutions to determine sink conditions for dissolution studies.

Example 7

Formulation of Insoluble Small Molecule Therapeutics in Lipid-Based Carriers (US20060051406A1)

Clofazimine (between 1 and 100 mg) and phosphocoline derivative DOPC (between 100 and 1000 mg) can be mixed in dichloromethane (1.5 mL). After the lipid and drug are completely dissolved, the solvent can be removed by nitrogen gas transfer and the residue can be subsequently dried overnight under vacuum to yield a homogeneous film of clofazimine. The film can be hydrated with PBS at pH 7.4 (3.15 mL) and vortexed to give a lipid formulation of clofazimine (compound:lipid mole-to-mole ratio between 0.01 and 1). The lipid formulation can be characterized by polarizing light microscopy (Olympus BX51) or similar equipment, and differential scanning calorimetry (TA Instruments, Model Q 100, New Castle, Del., at heating rate of 10° C./minute with N2 gas flow rate of 50 mL/minute). If no crystals are visible in the polarizing light microscopy image, this observation indicates complete solubilization of clofazimine in the lipid formulation.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

All documents mentioned herein are fully incorporated by reference herein in their entirety.

We claim:

1. A method for treating or lessening the severity of a disorder in a patient, wherein the disorder is selected from the group consisting of multiple sclerosis, plaque psoriasis, rheumatoid psoriasis, and vitiligo, wherein said method comprises administering to said patient a pharmaceutical composition consisting essentially of an effective amount of a compound of formula I:

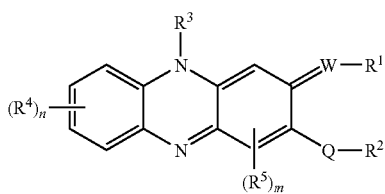

or a pharmaceutically acceptable salt thereof, wherein:

W is =O, =N—, or =C(R)—;

$R^1$ is absent if W is =O; or if W is =N—, then $R^1$ is an optionally substituted group selected from $C_{1-6}$ aliphatic, $C_{3-7}$ cycloaliphatic, a 6-10 membered monocyclic or bicyclic aromatic carbocyclic ring, or a 5-10 membered monocyclic or bicyclic saturated, partially unsaturated, or aromatic ring having 1-4 heteroatoms independently selected from nitrogen, oxygen, or sulfur; or if W is =C(R)—, then $R^1$ is hydrogen or an optionally substituted group selected from $C_{1-6}$ aliphatic, $C_{3-7}$ cycloaliphatic, a 6-10 membered monocyclic or bicyclic aromatic carbocyclic ring, or a 5-10 membered monocyclic or bicyclic saturated, partially unsaturated, or aromatic ring having 1-4 heteroatoms independently selected from nitrogen, oxygen, or sulfur;

Q is —O—, —S—, —C(R)$_2$—, or —N(R)—;

each R is independently hydrogen or an optionally substituted $C_{1-6}$ aliphatic group, or:

two R groups on the same nitrogen are taken together with the nitrogen atom to form a 4-7 membered saturated, partially unsaturated, or aromatic ring having 1-4 heteroatoms independently selected from nitrogen, oxygen, or sulfur;

$R^2$ is an optionally substituted group selected from $C_{3-7}$ cycloaliphatic, a 6-10 membered monocyclic or bicyclic aromatic carbocyclic ring, or a 5-10 membered monocyclic or bicyclic saturated, partially unsaturated, or aromatic ring having 1-4 heteroatoms independently selected from nitrogen, oxygen, or sulfur;

$R^3$ is an optionally substituted group selected from $C_{3-7}$ cycloaliphatic, a 6-10 membered monocyclic or bicyclic aromatic carbocyclic ring, or a 5-10 membered monocyclic or bicyclic saturated, partially unsaturated, or aromatic ring having 1-4 heteroatoms independently selected from nitrogen, oxygen, or sulfur;

n is 0, 1, 2, 3, or 4;

each $R^4$ is independently selected from halogen, CN, R, OR, SR, N(R)$_2$, C(O)R, C(O)OR, C(O)N(R)$_2$, N(R)C(O)R, OC(O)R, SO$_2$R, SO$_2$N(R)$_2$, N(R)SO$_2$R, or N(R)C(O)N(R)$_2$;

m is 0, 1 or 2; and each $R^5$ is independently selected from halogen, CN, R, OR, SR, or N(R)$_2$;

wherein each optionally substituted group is independently optionally substituted with halogen; —(CH$_2$)$_{0-4}$R°; —(CH$_2$)$_{0-4}$OR°; —O(CH$_2$)$_{0-4}$R°, —O—(CH$_2$)$_{0-4}$C(O)OR°; —(CH$_2$)$_{0-4}$ CH(OR°)$_2$; —(CH$_2$)$_{0-4}$SR°; —(CH$_2$)$_{0-4}$Ph, which may be substituted with R°; —(CH$_2$)$_{0-4}$ O(CH$_2$)$_{0-1}$Ph which may be substituted with R°; —CH=CHPh, which may be substituted with R°; (CH$_2$)$_{0-4}$O(CH$_2$)$_{0-1}$-pyridyl which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$ C(O)SR°; —(CH$_2$)$_{0-4}$C(O)OSiR°$_3$; —(CH$_2$)$_{0-4}$OC(O)R°; —OC(O)(CH$_2$)$_{0-4}$SR—, SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$ OC(O)NR°$_2$; —C(O)N(OR°) R°; —C(O)C(O)R°; —C(O)CH$_2$C(O)R°; —C(NOR°) R°; —(CH$_2$)$_{0-4}$ SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$ R°; —N(OR°)R°; —C(NH)NR°$_2$;—P(O)$_2$R°; —P(O)R°$_2$; —OP(O)R°$_2$; —OP(O)(OR°)$_2$; SiR°$_3$; —(C$_{1-4}$ straight or branched alkylene)O—N(R°$_2$; or —(C$_{1-4}$ straight or branched alkylene)C(O)O—N(R°$_2$, wherein each R° may be substituted as defined below and is independently hydrogen, $C_{1-6}$ aliphatic, —CH$_2$Ph, —O(CH$_2$)$_{0-1}$Ph, —CH$_2$—(5-6membered heteroaryl ring), or a 5-6-membered saturated, partially unsaturated, or aryl ring having 0-4 heteroatoms independently selected from nitrogen, oxygen, or sulfur; or two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below; or each saturated carbon atom of an optionally substituted group is independently optionally substituted with =O, =S, =NNR*$_2$, =NNHC(O)R*, =NNHC(O)OR*, =NNHS(O)$_2$R*, =NR*, =NOR*, —O(C(R*$_2$))$_{2-3}$O, or S(C(R*$_2$))$_{2-3}$S—, wherein each independent occurrence of R* is selected from hydrogen, C$_{1-6}$ aliphatic which may be substituted as defined below, or an unsubstituted 5-6 -membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6 -membered saturated, partially unsaturated, or aryl ring having 0-4 heteroatoms independently selected from nitrogen, oxygen, or sulfur;

R° (or the ring formed by taking two independent occurrences of R° together with their intervening atoms), is independently optionally substituted with halogen, —(CH$^2$)$_{0-2}$R$^\bullet$, (haloR$^\bullet$), —(CH$_2$)$_{0-2}$OH, —(CH$_2$)$_{0-2}$ OR$^\bullet$, —(CH$_2$)$_{0-2}$CH(OR$^\bullet$)$_2$; —O(halo R$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$ C(O)OR$^\bullet$, —(CH$_2$)$_{0-2}$SR$^\bullet$, —(CH$_2$)$_{0-2}$ SH, —(CH$_2$)$_{0-2}$NH$_2$, —(CH$_2$)$_{0-2}$NHR$^\bullet$, —(CH$_2$)$_{0-2}$NR$^\bullet$$_2$, —NO$_2$, -SiR$^\bullet$$_3$, -OSiR$^\bullet$$_3$, —C(O)SR$^\bullet$, —(C$_{1-4}$ straight or branched alkylene) C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur; or a saturated carbon atom of R° is optionally substituted with =O or =S;

each R* is independently optionally substituted with halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur;

each substitutable nitrogen of an optionally substituted group is independently optionally substituted with —R$^\dagger$, —NR$^\dagger$$_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger$$_2$, —C(S)NR$^\dagger$$_2$, —C(NH)NR$^\dagger$$_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono or bicyclic ring having 0-4 heteroatoms independently selected from nitrogen, oxygen, or sulfur; and each R$^\dagger$ is independently optionally substituted with halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6 -membered saturated, partially unsaturated, or aryl ring having 0-4 heteroatoms independently selected from nitrogen, oxygen, or sulfur; and a pharmaceutically acceptable carrier.

2. The method according to claim 1, wherein said compound is selected from the group consisting of formula I-a, formula I-b, formula I-c and formula I-d:

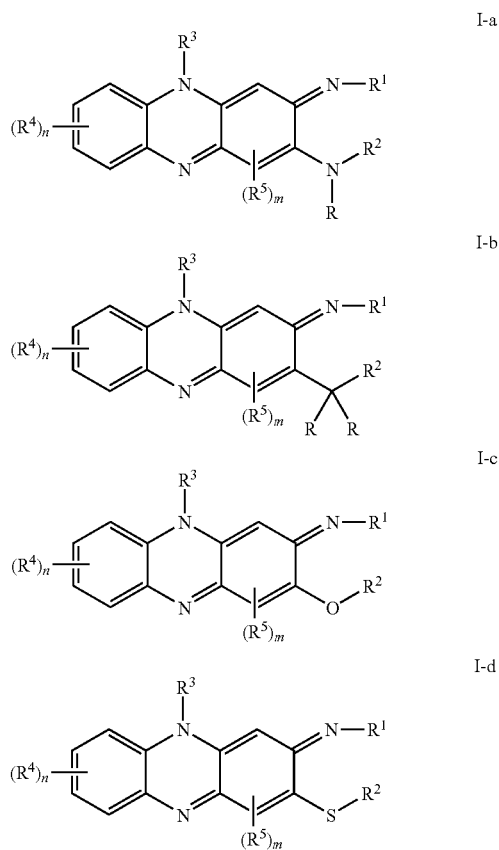

or a pharmaceutically acceptable salt thereof.

3. The method according to claim 1, wherein said compound is administered in one or more loading doses followed by one or more maintenance doses, wherein said one or more maintenance doses comprise less compound than said one or more loading doses.

4. The method of claim 1, wherein the disorder is multiple sclerosis.

5. The method of claim 1, wherein the disorder is plaque psoriasis, rheumatoid psoriasis, or vitiligo.

6. The method of claim 1, wherein the compound is clofazimine.

7. The method according to claim 1, wherein said compound is selected from the group consisting of:
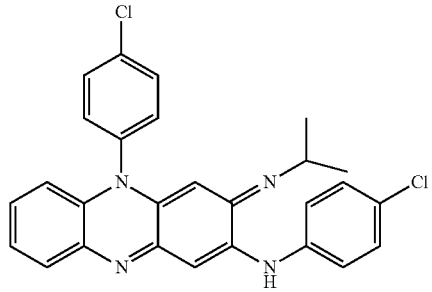
I-1
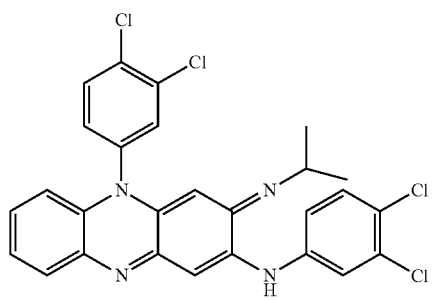
I-2
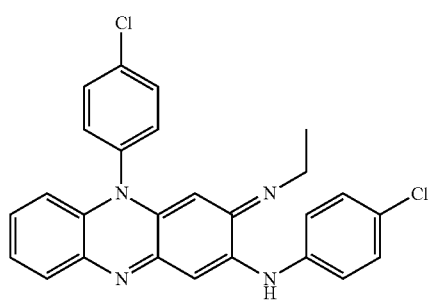
I-3
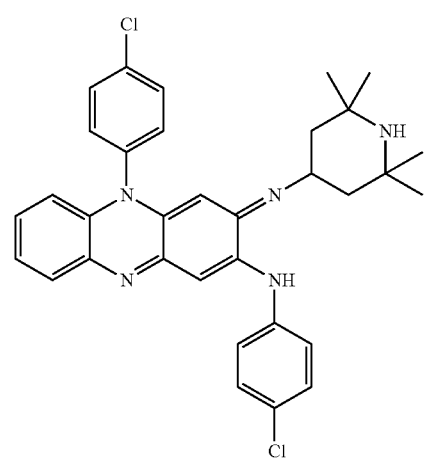
I-4
-continued
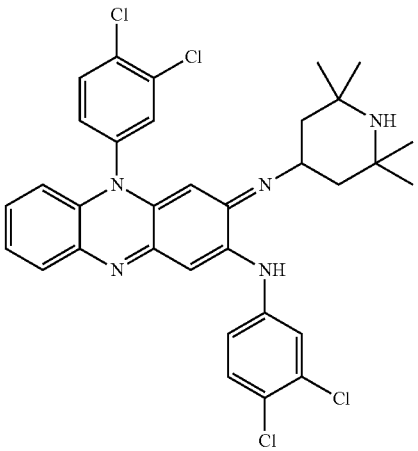
I-5
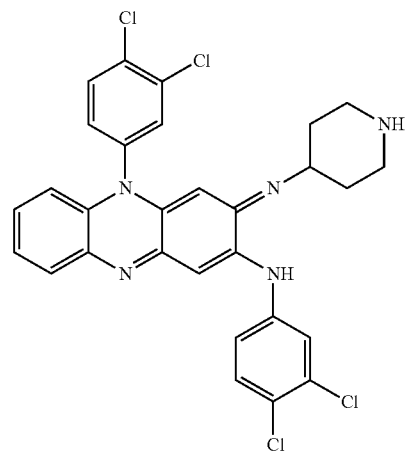
I-6
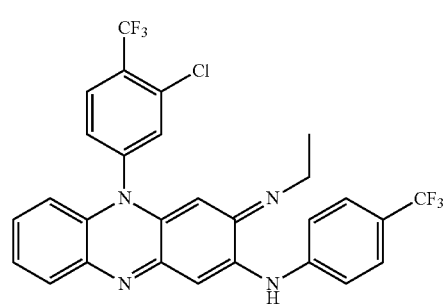
I-7
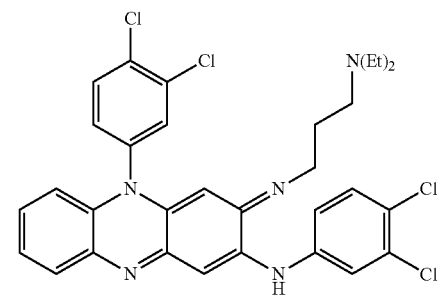
I-8

-continued

I-9

I-10

I-11

I-12

I-13

I-14

I-15

I-16

I-17

I-18

-continued
I-19
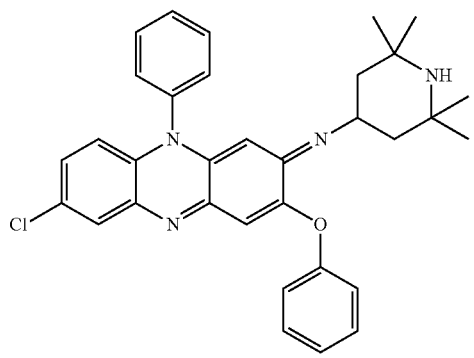
I-20
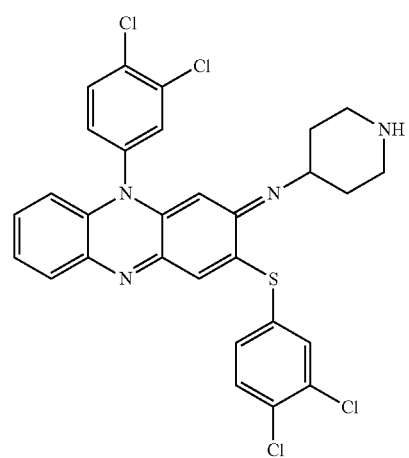
I-21
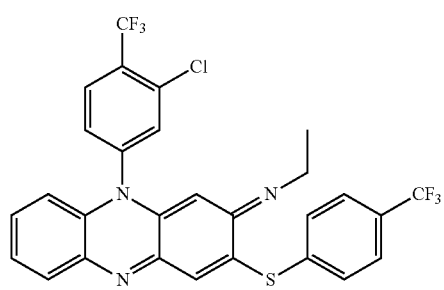
I-22
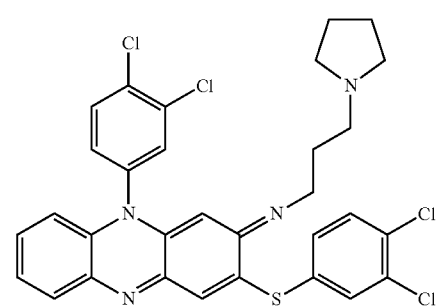
-continued
I-23
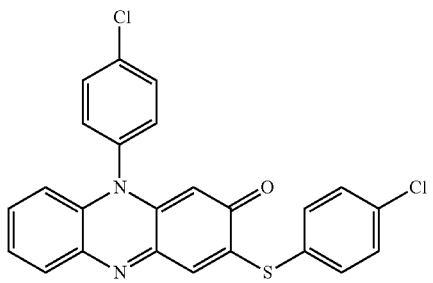
I-24
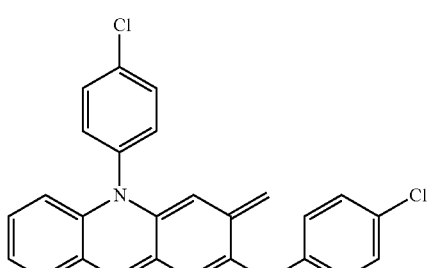
I-25
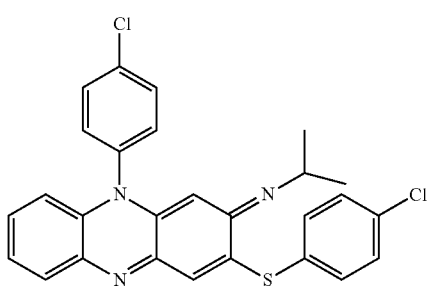
I-26
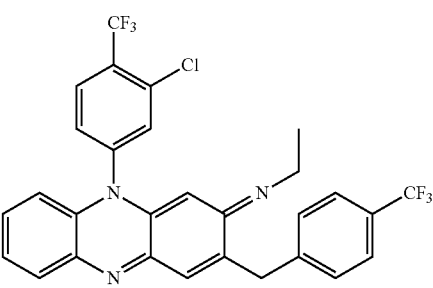
I-27
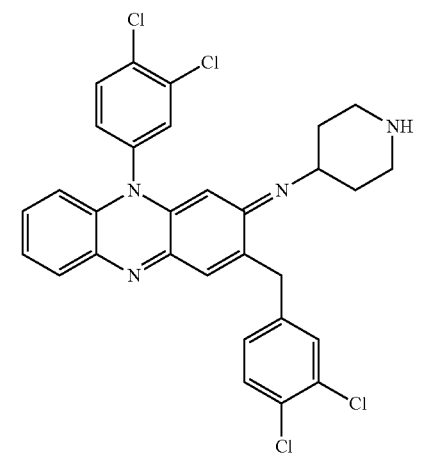

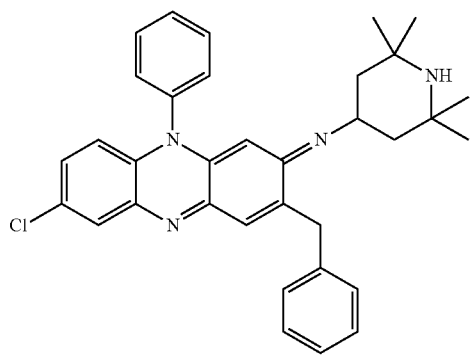
I-28
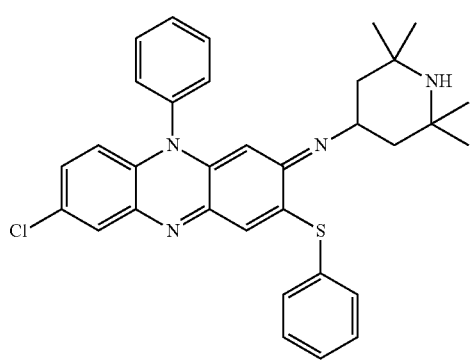
I-29
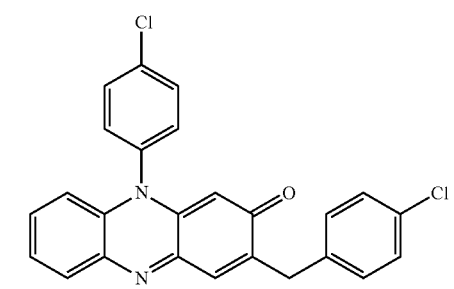
I-30
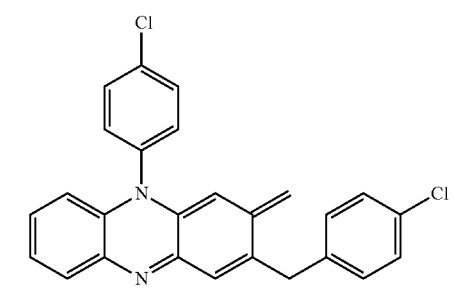 [SMILES: C=c1cc2c(cc1Cc1ccc(Cl)cc1)=Nc1ccccc1N2c1ccc(Cl)cc1]
I-31
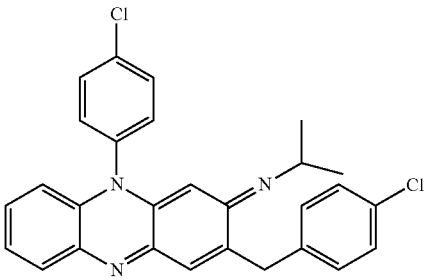 [SMILES: CC(C)N=c1cc2n(-c3ccc(Cl)cc3)c3ccccc3nc-2cc1Cc1ccc(Cl)cc1]
I-32
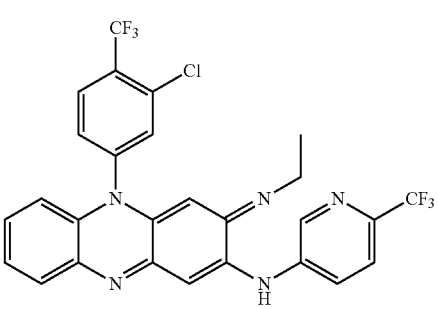 [SMILES: CCN=c1cc2n(-c3ccc(C(F)(F)F)c(Cl)c3)c3ccccc3nc-2cc1Nc1ccc(C(F)(F)F)nc1]
I-33
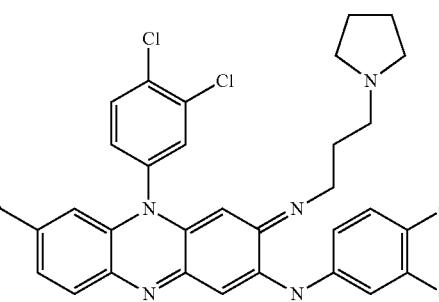
I-34
and
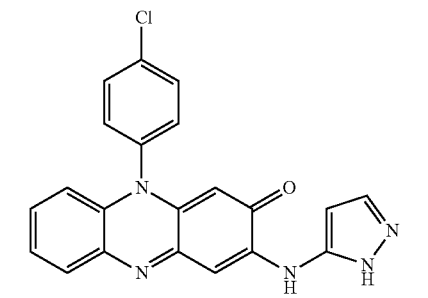
I-35
or a pharmaceutically acceptable salt thereof.
8. The method according to claim 7, wherein said compound is compound I-1, or a pharmaceutically acceptable salt thereof.
* * * * *

SEQUENCE LISTING

<160> NUMBER OF SEQ ID NOS: 1

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gccaccttct cgcgaaacat                                                   20